US011672794B2

(12) United States Patent
Wang et al.

(10) Patent No.: US 11,672,794 B2
(45) Date of Patent: Jun. 13, 2023

(54) THERAPEUTIC TARGETING OF THE BAP1 COMPLEX IN CANCER

(71) Applicant: NORTHWESTERN UNIVERSITY, Evanston, IL (US)

(72) Inventors: Lu Wang, Chicago, IL (US); Ali Shilatifard, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 42 days.

(21) Appl. No.: 16/931,942

(22) Filed: Jul. 17, 2020

(65) Prior Publication Data

US 2021/0060001 A1  Mar. 4, 2021

Related U.S. Application Data

(60) Provisional application No. 62/875,434, filed on Jul. 17, 2019.

(51) Int. Cl.
*A61K 31/473* (2006.01)
*A61P 35/02* (2006.01)
*A61K 31/423* (2006.01)

(52) U.S. Cl.
CPC .......... *A61K 31/473* (2013.01); *A61K 31/423* (2013.01); *A61P 35/02* (2018.01)

(58) Field of Classification Search
None
See application file for complete search history.

(56) References Cited

U.S. PATENT DOCUMENTS

| 8,110,583 | B2 * | 2/2012 | Staehle | A61P 27/02 |
| | | | | 546/79 |
| 8,450,334 | B2 * | 5/2013 | Vasioukhin | A61K 51/00 |
| | | | | 514/290 |
| 8,664,266 | B2 * | 3/2014 | Vasioukhin | A61K 31/433 |
| | | | | 514/468 |
| 9,182,402 | B2 * | 11/2015 | Vasioukhin | A61K 31/433 |
| 10,059,708 | B2 | 8/2018 | Shilatifard | |
| 10,308,698 | B2 | 6/2019 | Shilatifard | |
| 10,640,502 | B2 | 5/2020 | Shilatifard | |
| 2015/0018326 | A1 | 1/2015 | Jiang | |
| 2017/0305901 | A1 | 10/2017 | Shilatifard | |
| 2018/0009870 | A1 | 1/2018 | Shilatifard | |
| 2018/0319795 | A1 | 11/2018 | Shilatifard | |
| 2019/0231759 | A1 | 8/2019 | Shilatifard | |
| 2020/0223895 | A1 | 7/2020 | Shilatifard | |

FOREIGN PATENT DOCUMENTS

WO  2004072046 A2  8/2004

OTHER PUBLICATIONS

Wang et al., "Epigenetic targeted therapy of stabilized BAP1 in ASXL1 gain-of-function mutated leukemia", 2021, Nature Cancer, 2(5), pp. 515-526. (doi.org/10.1038/s43018-021-00199-4) (Year: 2021).*
M Katoh, "Functional and cancer genomics of ASXL family members", 2013, British Journal of Cancer, 109(2), pp. 299-306. (DOI: 10.1038/bjc.2013.281) (Year: 2013).*
Abdel-Wahab, O. et al., ASXL1 Mutations Promote Myeloid Transformation through Loss of PRC2-Mediated Gene Repression. Cancer Cell 22, 180-193 (2012).
Anniyappan, M. et al. "Urea nitrate catalyzed imino Diels-Alder reactions: synthesis of cyclopentaquinolines, pyranoquinolines, and furoquinoline derivatives." Synthetic communications 32.1 (2002): 99-103.
Babu, G. et al. "Imino Diels-Alder reactions catalyzed by indium trichloride (InCl3). Facile synthesis of quinoline and phenanthridinone derivatives." Tetrahedron letters 38.28 (1997): 5025-5026.
Babu, G. et al. "Indium trichloride (InCl3) catalyzed imino Diels-Alder reactions: an efficient synthesis of cyclopentaquinolines, azabicyclooctanones and azabicyclononanones." Tetrahedron 54.8 (1998): 1627-1638.
Balasubramani et al., Cancer-associated ASXL1 mutations may act as gain-of-function mutations of the ASXL1-BAP1 complex. Nat. Commun. 6, 7307 (2015).
Bejar R. et al., Clinical Effect of Point Mutations in Myelodysplastic Syndromes. New Engl J Med 364, 2496-2506 (2011).
Bononi A. et al., BAP1 regulates IP3R3-mediated Ca2+ flux to mitochondria suppressing cell transformation. Nature 546, 549-553 (2017).
Bosco, E. E., et al. "Rational design of small molecule inhibitors targeting the Rac GTPase-p67phox signaling axis in inflammation." Chemistry & biology 19.2 (2012): 228-242.
Bott et al., "The nuclear deubiquitinase BAP1 is commonly inactivated by somatic mutations and 3p21.1 losses in malignant pleural mesothelioma," Nat. Genet. 43, 668-672 (2011).
Campagne A. et al., BAP1 complex promotes transcription by opposing PRC1-mediated H2A ubiquitylation. Nat Commun 10, (Jan. 2019).
Carbone et al., "BAP1 and cancer," Nat. Rev. Cancer, 153-159 (2013).
Carlino, L., et al. "Structure-Activity Relationships of Hexahydrocyclopenta [c] quinoline Derivatives as Allosteric Inhibitors of CDK2 and EGFR." ChemMedChem 13.24 (2018): 2627-2634.

(Continued)

*Primary Examiner* — My-Chau T. Tran
(74) *Attorney, Agent, or Firm* — Quarles & Brady LLP

(57) ABSTRACT

Disclosed are methods for methods, compounds, and compositions for treating cancers characterized by therapeutic targeting of the BAP1 histone H2A deubiquitinase (DUB) complex, otherwise referred to herein as the BAP1 complex. In particular, the methods, compounds, and compositions disclosed herein relate to the use of therapeutic agents that inhibit the biological activity of the BAP1 complex for treating cancers such as myeloid neoplasms.

16 Claims, 51 Drawing Sheets

Specification includes a Sequence Listing.

(56) References Cited

OTHER PUBLICATIONS

Connelly, C. M., et al. "Discovery of inhibitors of microRNA-21 processing using small molecule microarrays." ACS chemical biology 12.2 (2017): 435-443.

Daou S. et al., The BAP1/ASXL2 Histone H2A Deubiquitinase Complex Regulates Cell Proliferation and Is Disrupted in Cancer. J Biol Chem 290, 28643-28663 (2015).

D'Arcy P. et al., Inhibition of proteasome deubiquitinating activity as a new cancer therapy. Nat Med 17, 1636-U1150 (2011).

Dey A. et al., Loss of the Tumor Suppressor BAP1 Causes Myeloid Transformation. Science 337, 1541-1546 (2012).

Fang, Y. et al. The potential role of ubiquitin c-terminal hydrolases in oncogenesis. Bba-Rev Cancer 1806, 1-6 (2010).

Gelsi-Boyer V. et al., Mutations of polycomb-associated gene ASXL1 in myelodysplastic syndromes and chronic myelomonocytic leukaemia. Brit J Haematol 145, 788-800 (2009).

Grieco, P. A., et al. "Role reversal in the cyclocondensation of cyclopentadiene with heterodienophiles derived from aryl amines and aldehydes: Synthesis of novel tetrahydroquinolines." Tetrahedron letters 29.46 (1988): 5855-5858.

Guo Y. et al., Reduced BAP1 activity prevents ASXL1 truncation-driven myeloid malignancy in vivo. Leukemia 32, 1834-1837(2018).

He M. et al., Intrinsic apoptosis shapes the tumor spectrum linked to inactivation of the deubiquitinase BAP1. Science 364, 283. (Apr. 2019).

Katoh, Functional and cancer genomics of ASXL family members. Br. J. Cancer 109, 299-306 (2013).

Lawrence M.S. et al., Mutational heterogeneity in cancer and the search for new cancer-associated genes. Nature 499, 214-218 (2013).

Mashtalir N. et al., Autodeubiquitination Protects the Tumor Suppressor BAP1 from Cytoplasmic Sequestration Mediated by the Atypical Ubiquitin Ligase UBE2O. Mol Cell 54, 392-406 (2014).

Misaghi S. et al., Association of C-Terminal Ubiquitin Hydrolase BRCA1-Associated Protein 1 with Cell Cycle Regulator Host Cell Factor 1. Mol Cell Biol 29, 2181-2192 (2009).

Morris, M.R. et al. The epigenetic landscape of renal cancer. Nat Rev Nephrol 13, 47-60 (2017).

Murali, R. et al. Tumours associated with BAP1 mutations. Pathology 45, 116-126 (2013).

Ortega-Molina A. et al., The histone lysine methyltransferase KMT2D sustains a gene expression program that represses B cell lymphoma development. Nat Med 21, 1199. (2015).

Pan et al., "BAP1 regulates cell cycle progression through E2F1 target genes and mediates transcriptional silencing via H2A monoubiquitination in uveal melanoma cells. Int. J. Biochem," Cell Biol 60, 176-184 (2015).

Patel J.P. et al., Prognostic Relevance of Integrated Genetic Profiling in Acute Myeloid Leukemia. New Engl J Med 366, 1079-1089 (2012).

Qin J.Y. et al., BAP1 promotes breast cancer cell proliferation and metastasis by deubiquitinating KLF5. Nat Commun 6, (2015).

Rasmussen, K. D. et al. Role of TET enzymes in DNA methylation, development, and cancer. Gene Dev 30, 733-750 (2016).

Sahtoe, D.D. et al BAP1/ASXL1 recruitment and activation for H2A deubiquitination. Nat Commun 7, (2016).

Sartori, G., et al. "Clay/Water Mixtures—A Heterogeneous and Ecologically Efficient Catalyst for the Three-Component Stereoselective Synthesis of Tetrahydroquinolines." European Journal of Organic Chemistry 2001.13 (2001): 2513-2518.

Scheuermann et al., "Histone H2A deubiquitinase activity of the Polycomb repressive complex PR-DUB," Nature 465, 243-247 (2010).

Verdijk R. et al., Clinical significance of immunohistochemistry for detection of BAP1 mutations in uveal melanoma. Virchows Archive 465, S44-S44 (2014).

Wang L. et al. UTX Mutations in Human Cancer. Cancer Cell 35, 168-176 (Feb. 2019).

Wang L. et al., Resetting the epigenetic balance of Polycomb and COMPASS function at enhancers for cancer therapy. Nat Med 24, 758. (2018).

Yang H. et al., Gain of function of ASXL1 truncating protein in the pathogenesis of myeloid malignancies. Blood 131, 328-341 (2018).

Yu, H. et al., The Ubiquitin Carboxyl Hydrolase BAP1 Forms a Ternary Complex with YY1 and HCF-1 and Is a Critical Regulator of Gene Expression. Mol Cell Biol 30, 5071-5085 (2010).

Zhang J.Y. et al., Disruption of KMT2D perturbs germinal center B cell development and promotes lymphomagenesis. Nat Med 21, 1190. (2015).

Zhang, X.-F., et al. "Inhibition of histo-blood group antigen binding as a novel strategy to block norovirus infections." PloS one 8.7 (2013): e69379.

Koopmans, A. E., et al. "Clinical significance of immunohistochemistry for detection of BAP1 mutations in uveal melanoma." Modern pathology 27.10 (2014): 1321-1330.

\* cited by examiner

F

| Protein | ASXL1 purification | |
|---|---|---|
| | GFP Peptide No. | ASXL1 (aa1-591) Peptide No. |
| ASXL1 | 0 | 75 |
| BAP1 | 0 | 139 |
| HCFC1 | 0 | 120 |
| OGT | 0 | 50 |
| FOXK2 | 0 | 14 |
| FOXK1 | 0 | 13 |

```
                              SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
tcagcccact taccagatat gccc                                              24

<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2
tcagcccact taacacatat gccc                                              24

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
ttctagagtc cgtccggagt                                                   20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
aggctcagca ggtcttacga                                                   20

<210> SEQ ID NO 5
<211> LENGTH: 12
<212> TYPE: PRT
<213> ORGANISM: Artificial Sequence
<220> FEATURE:
<223> OTHER INFORMATION: synthetic

<400> SEQUENCE: 5

Thr Tyr Gln Ile Cys Pro Arg Ile Ile Pro Thr Thr
1               5                   10
```

```
<210> SEQ ID NO 6
<211> LENGTH: 36
<212> TYPE: DNA
<213> ORGANISM: Artificial Sequence
<220> FEATURE:
<223> OTHER INFORMATION: synthetic

<400> SEQUENCE: 6
acttaccaga tatgccccg gatcatcccc accacg                                  36

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
acttaccaga tatgccccg gatcatcccc accacg                                  36

<210> SEQ ID NO 8
<211> LENGTH: 35
<212> TYPE: DNA
<213> ORGANISM: Artificial Sequence
<220> FEATURE:
<223> OTHER INFORMATION: synthetic

<400> SEQUENCE: 8
acttaccaga ttgccccgg atcatcccca ccacg                                   35

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
acttaccaga tcatccccac cacg                                              24
```

THERAPEUTIC TARGETING OF THE BAP1 COMPLEX IN CANCER

CROSS-REFERENCE TO RELATED PATENT APPLICATIONS

This application claims the benefit of priority under 35 U.S.C. § 119(e) to U.S. Provisional Application 62/875,434, filed on Jul. 17, 2019, the content of which is incorporated herein by reference in its entirety.

STATEMENT REGARDING FEDERALLY SPONSORED RESEARCH OR DEVELOPMENT

This invention was made with government support under CA197569 awarded by the National Institutes of Health. The government has certain rights in the invention.

REFERENCE TO A SEQUENCE LISTING SUBMITTED VIA EFS-WEB

The content of the ASCII text file of the sequence listing named "702581_01800_ST25.txt" which is 1.94 kb in size was created on Nov. 10, 2020 and electronically submitted via EFS-Web herewith the application is incorporated herein by reference in its entirety.

BACKGROUND

The field of the invention relates to methods for treating cancers. In particular, the field of the invention relates to methods, compounds, and compositions for treating cancers characterized by therapeutic targeting of the BAP1 histone H2A deubiquitinase complex, otherwise referred to as the BAP1 complex. The methods, compounds, and compositions disclosed herein relate to the use of therapeutic agents that inhibit the biological activity of the BAP1 complex for treating cancers such as myeloid neoplasms.

The ASXL1 gene is the human homolog of the *Drosophila* Asx gene, a core subunit in the BAP1 histone H2A deubiquitinase complex (i.e., the BAP1 complex). Mutations of ASXL1 occur in myeloid neoplasms, including acute myeloid leukemia (AML), myelodysplastic syndrome (MDS), myeloproliferative neoplasm (MPN), chronic myelomonocytic leukemia (CMML), and chronic myeloid leukemia (CML) and are uniformly associated with poor prognosis. However, the molecular basis of the role of ASXL1 mutations in regulating the BAP1 complex during leukemogenesis remains unclear. Here, the inventors demonstrate that cancer-associated frame-shift ASXL1 truncations, originally proposed to act as destabilizing loss-of-function mutations, in fact encode stable gain-of-function proteins. Truncated ASXL1 stabilizes BAP1 and enhances BAP1 complex recruitment to chromatin and promotes the expression of numerous leukemia associated genes such as HMGN5, STAT5A, HOXA11, BCAR1, TWIST1 and MBD2. Chemical inhibition of BAP1 fully rescues these changes in the gene expression pattern in leukemic cells inhibiting tumor progression. The inventors' work represents a breakthrough advance in the understanding of the molecular mechanisms of ASXL1 mutations in leukemic pathogenesis and identifies small molecular inhibitors of BAP1 function as a potential targeted therapy for leukemia.

SUMMARY

Disclosed are methods for methods, compounds, and compositions for treating cancers characterized by therapeutic targeting of the BAP1 histone H2A deubiquitinase (DUB) complex, otherwise referred to as the BAP1 complex. In particular, the methods, compounds, and compositions disclosed herein relate to the use of therapeutic agents that inhibit the biological activity of the BAP1 complex for treating cancers such as myeloid neoplasms.

The therapeutic agents may include, but are not limited to, compounds which are small molecule inhibitors. The compounds may be formulated as pharmaceutical compositions, for example for treating cancers associated with BAP1 complex, including myeloid cancers characterized by mutations in the ASXL1 gene.

WT and ASXL1-fs THP1 cells. All rows are centered ASXL1-fs peaks, and further divided into TSS and non-TSS regions. TSS and non-TSS regions were further divided into three clusters each by k-means. n=2. D) Log2 fold-change heat map shows the comparison of ASXL1, BAP1 and H2AK119Ub occupancy between ASXL1-WT and ASXL1-fs cells (left panel). The right panel shows the log2 (fold change) of nearby gene expression in ASXL1-WT and ASXL1-fs cells, n=2. E) Representative genome browser tracks of ASXL1 and BAP1 occupancy between ASXL1-WT and ASXL1-fs THP1 cells. F) Average plot showing gain of ASXL1 and BAP1 occupancy at TSS regions of all 608 up-regulated genes in ASXL1-fs THP1 cells.

Figure 4:
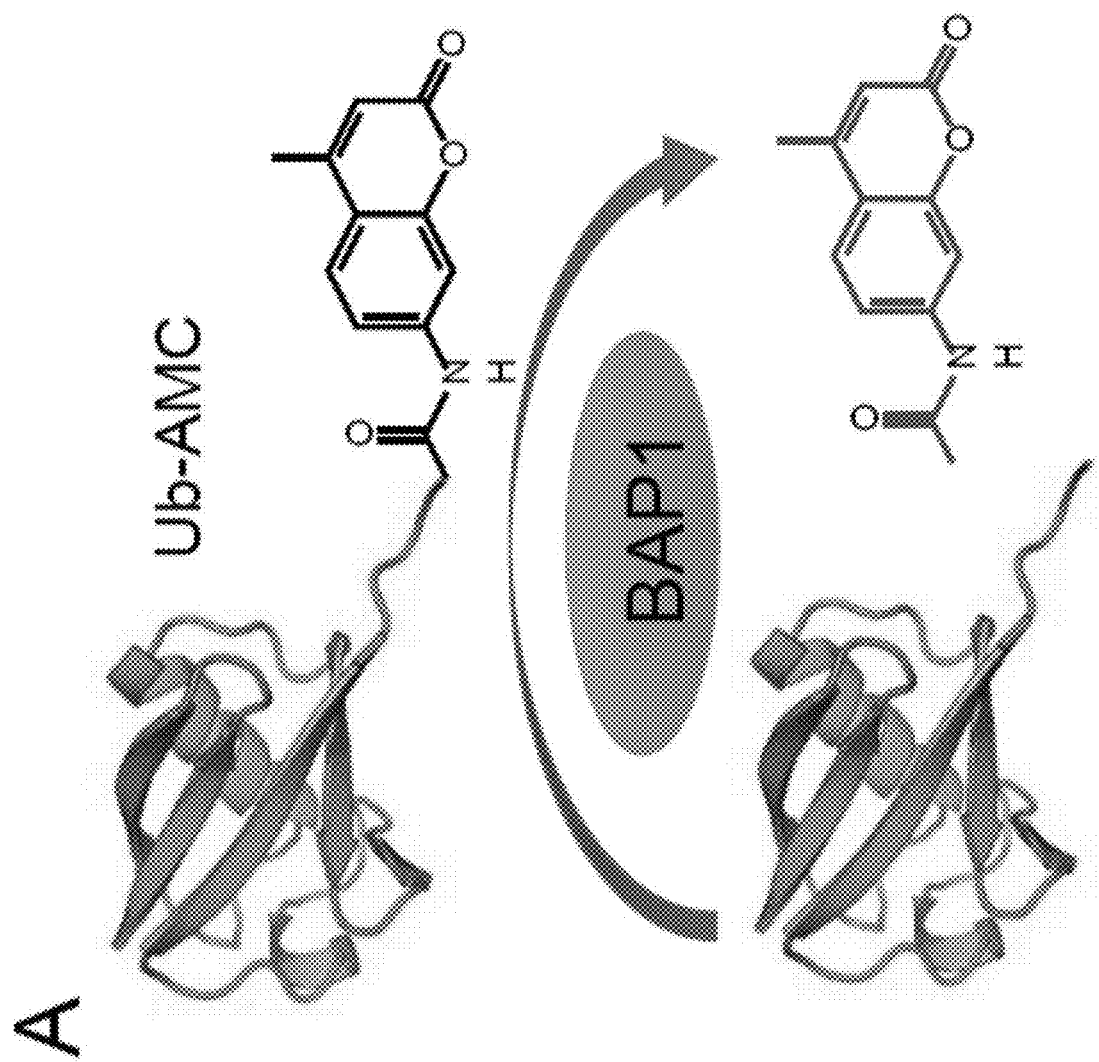
Figure 4:
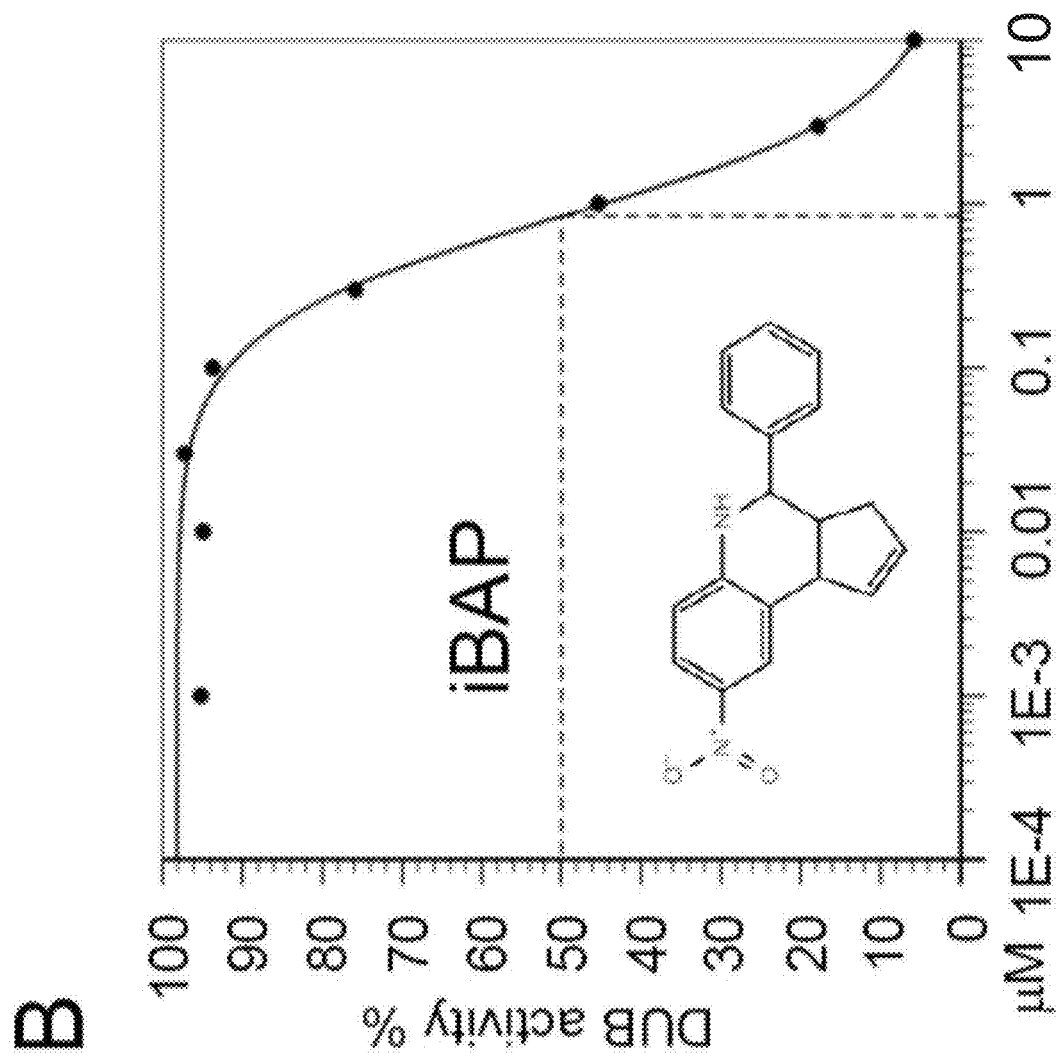
Figure 4:
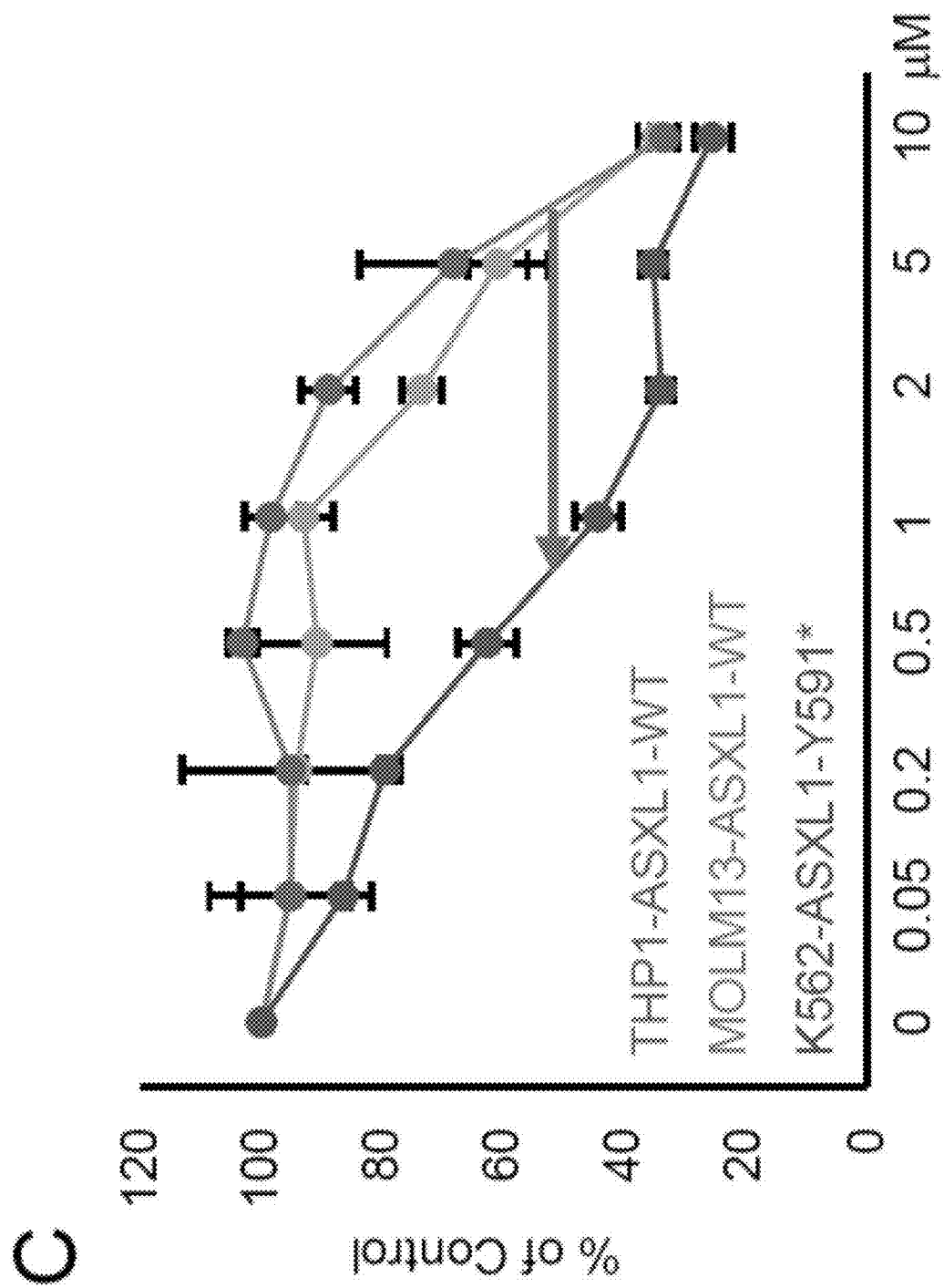
Figure 4:
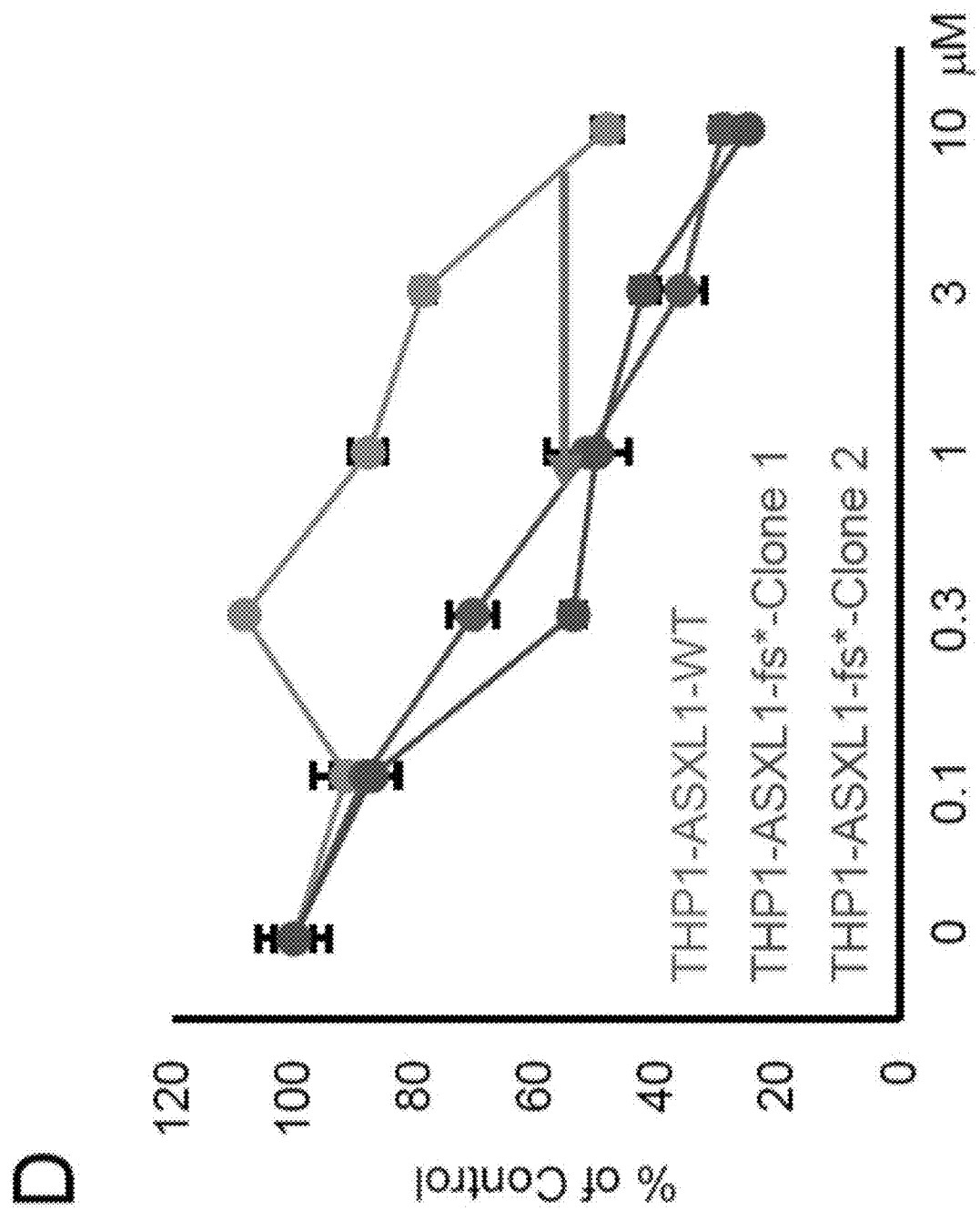
Figure 4:
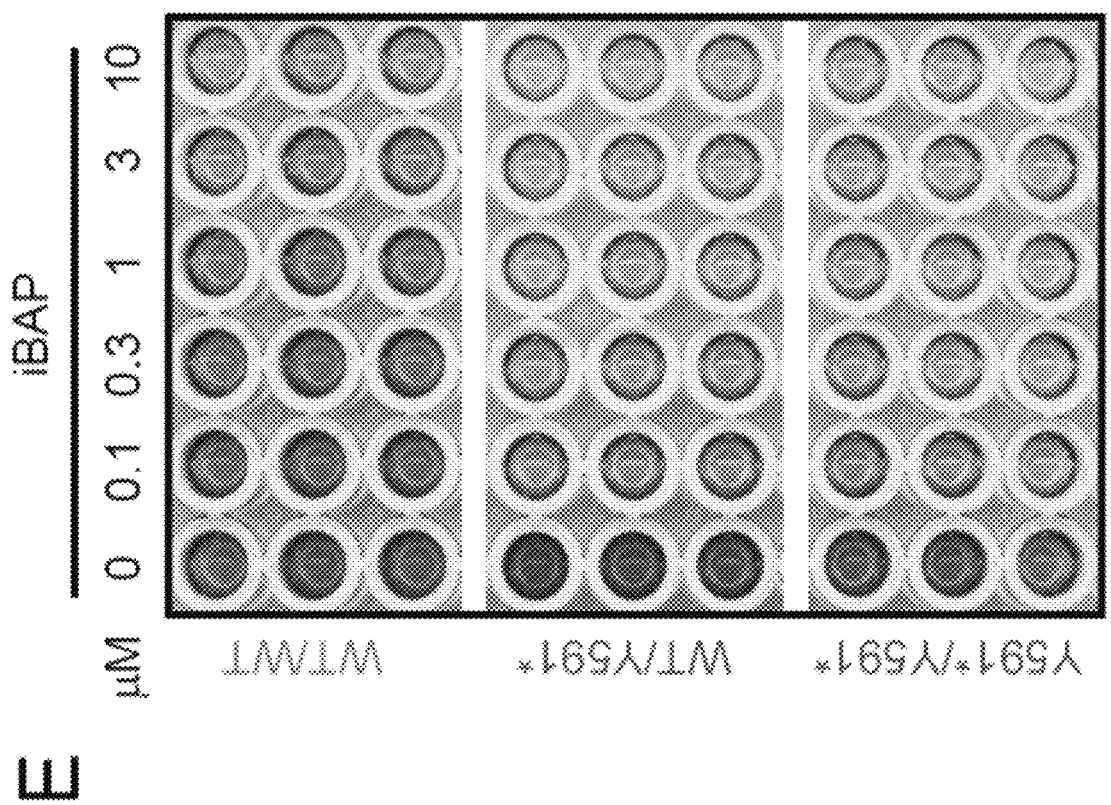
Figure 4:
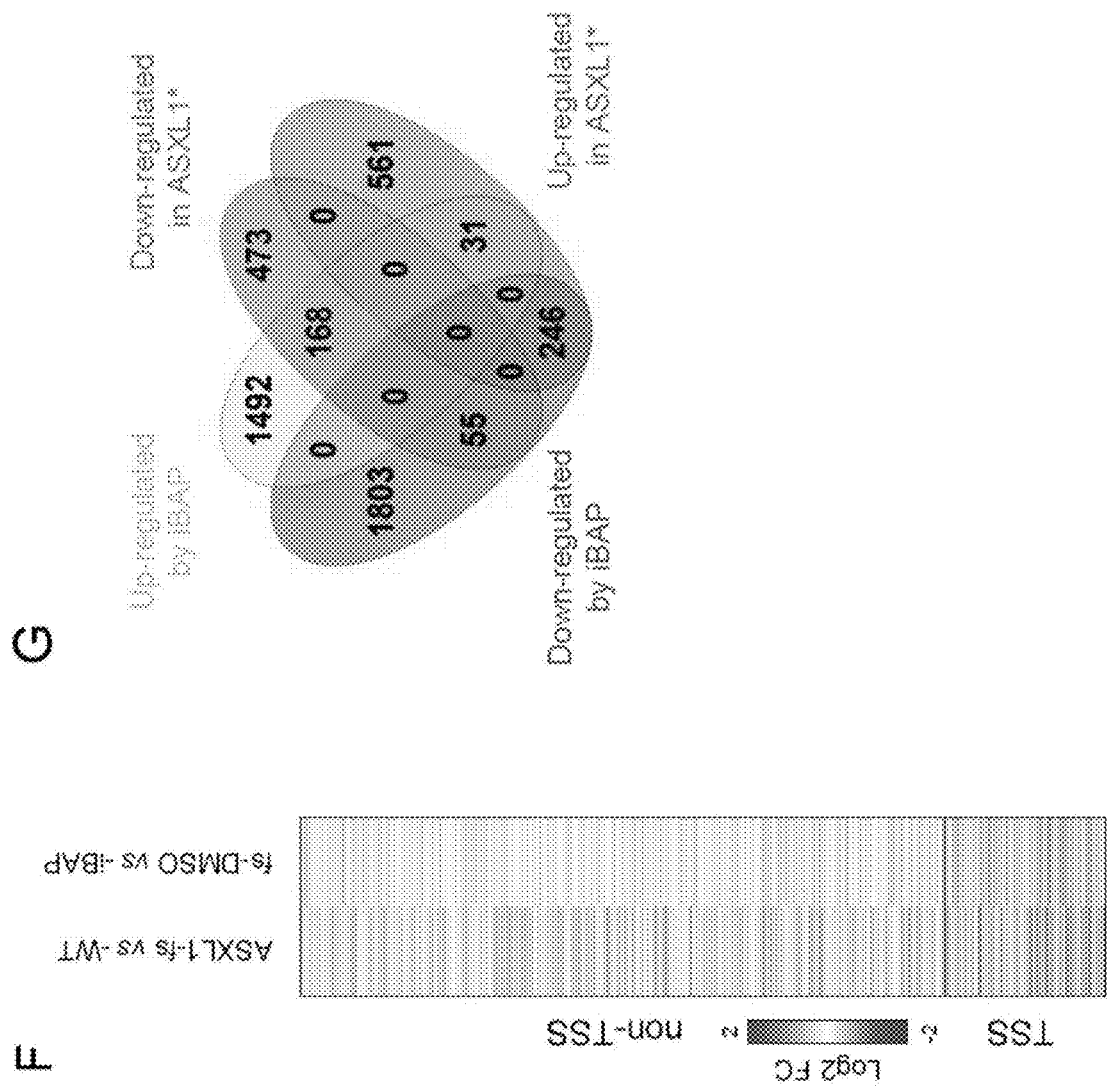
Figure 4:
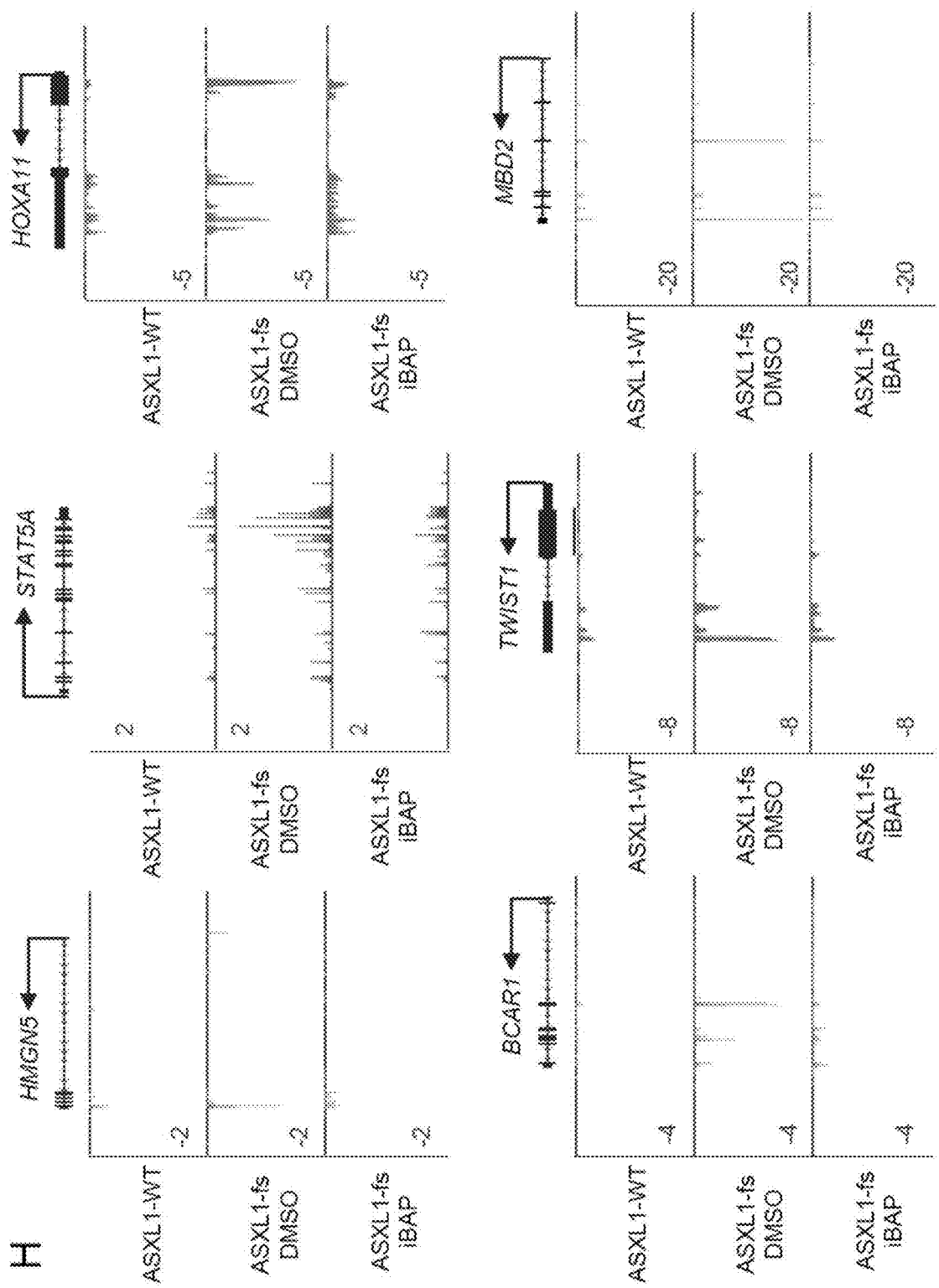

FIG. 4. iBAP selectively inhibit cells harboring ASXL1 GOF mutations. A) Cartoon of Ub-AMC screening platform. B) Structure of iBAP and the IC50 of iBAP in vitro with Ub-AMC as the substrate. C) THP1, MOML13 and K562 cells were treated with different concentrations of iBAP for 72 hours, the cell viability was determined by cell counting assay, n=3. THP1-ASXL1-WT, THP-ASXL1-fs-Clone 1 and THP 1-ASXL1-fs-Clone 2 cells were treated with different concentrations of iBAP for 72 hours, the cell viability was determined by cell counting assay, n=3 (D) and MTT assay, n=3 (E). F) The venn-diagram shows the overlap genes regulated by ASXL1 mutation and iBAP treatment. G) The log2 (fold change) of nearby gene expression in ASXL1-WT and ASXL1-fs cells, n=2. RNA-seq was performed for ASXL1-WT, and ASXL1-fs THP1 cells, and for ASXL1-fs cells treated with DMSO or iBAP. The heat maps shows the log2 fold change in expression for the nearest gene of the indicated peaks comparing ASXL1-fs cells with wild-type cells (left), and for the nearest gene of the indicated peaks comparing ASXL1-fs cells treated with DMSO or iBAP (right). H) Representative tracks showing the expression level of HMGN5, STAT5A, HOXA11, BCAR1, TWIST1 and MBD2 genes in THP1-ASXL1-WT and THP1-ASXL1-fs treated with either DMSO or iBAP.

Figure 5:
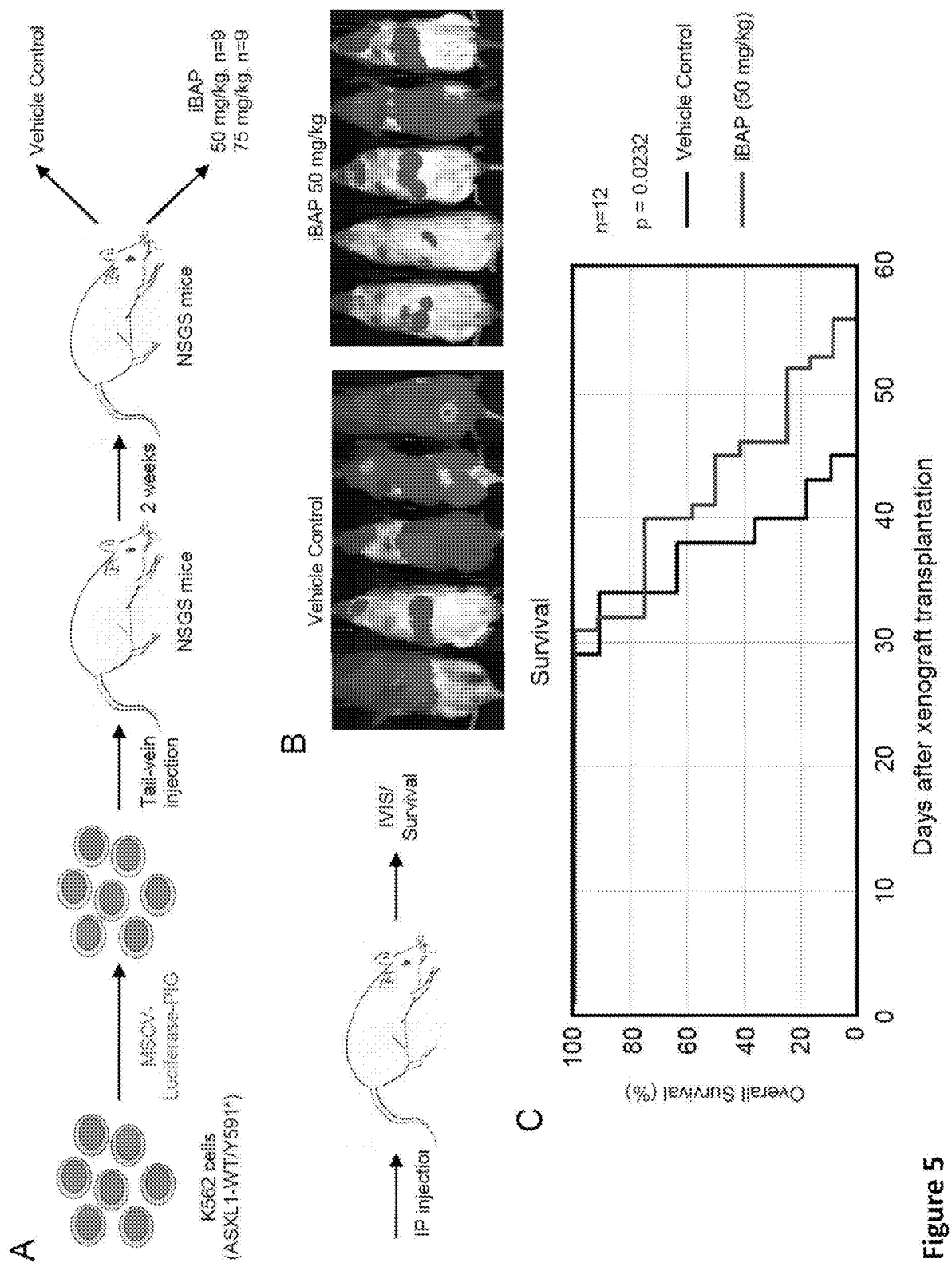

FIG. 5. iBAP delays the progression of ASXL1-mutant leukemia and improves survival. A) Schematic of the development K562 leukemia and iBAP inhibitor treatment in a NSGS mouse model. Drug treatments were started at day 14 after transplantation. B) The Relative luminescence intensity is shown for five mice per treatment group on 21 of treatment. C) Kaplan-Meier survival curves of K562 transplanted NSGS mice after vehicle and iBAP treatment at day 40. Vehicle or 50 mg/kg was administered daily by I.P. The number (n) indicates the number of mice in each group. The P-values were calculated using the log-rank test.

Figure 6:
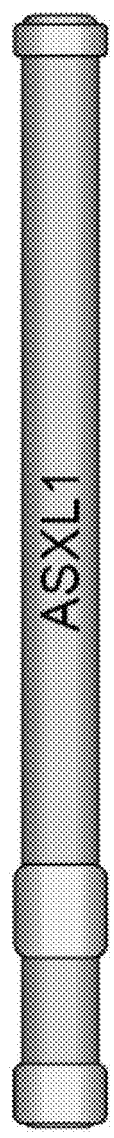
Figure 6:
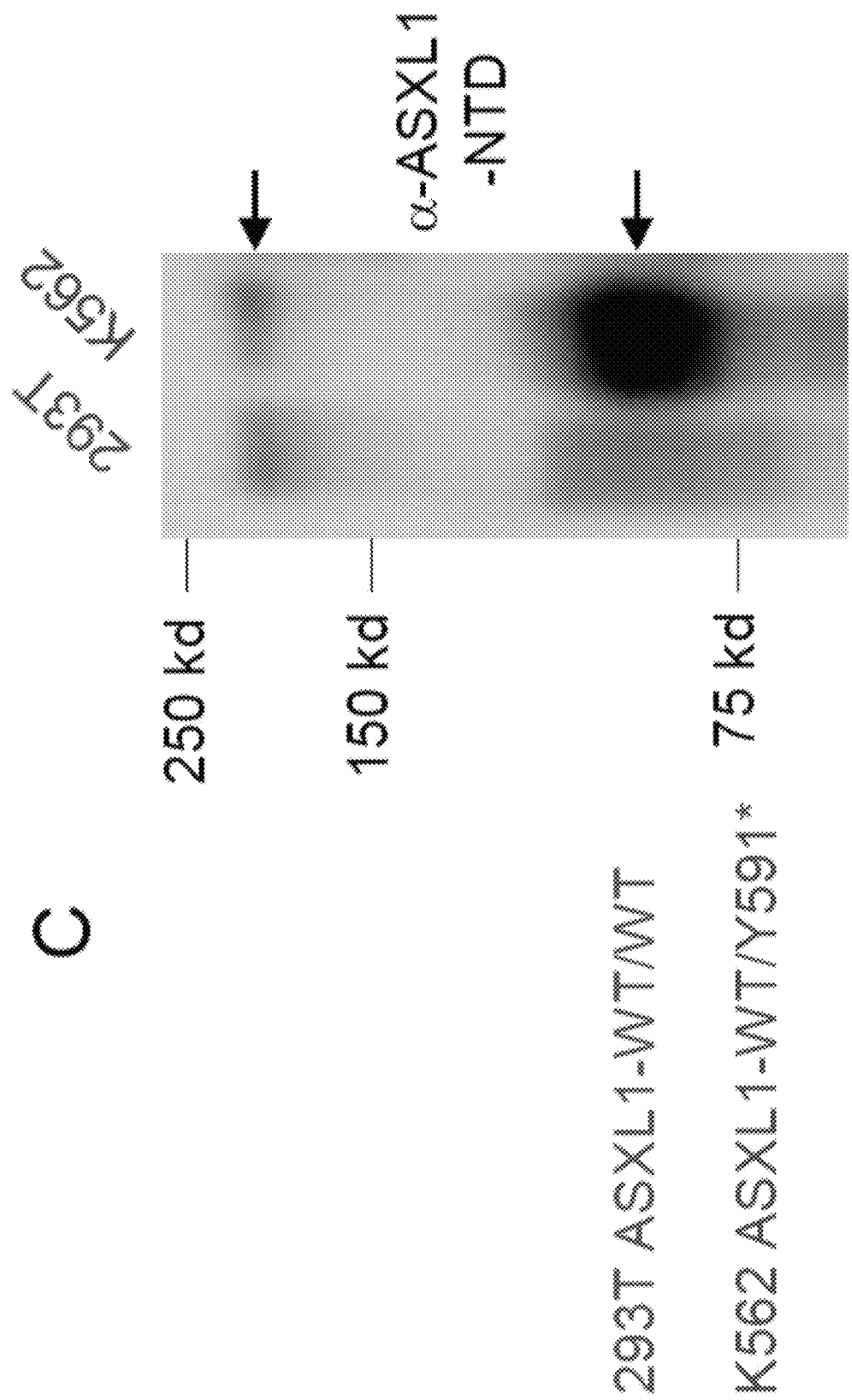
Figure 6:
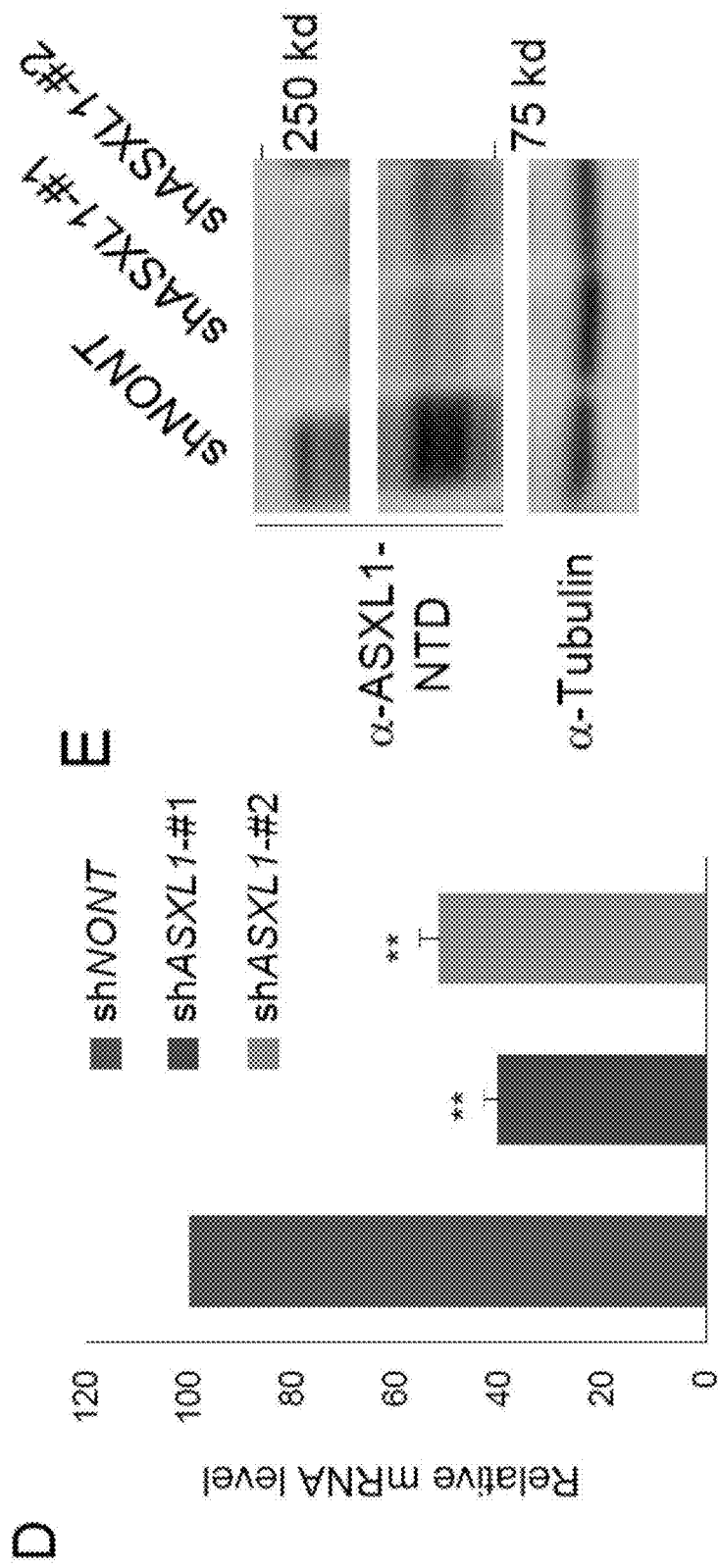
Figure 6:
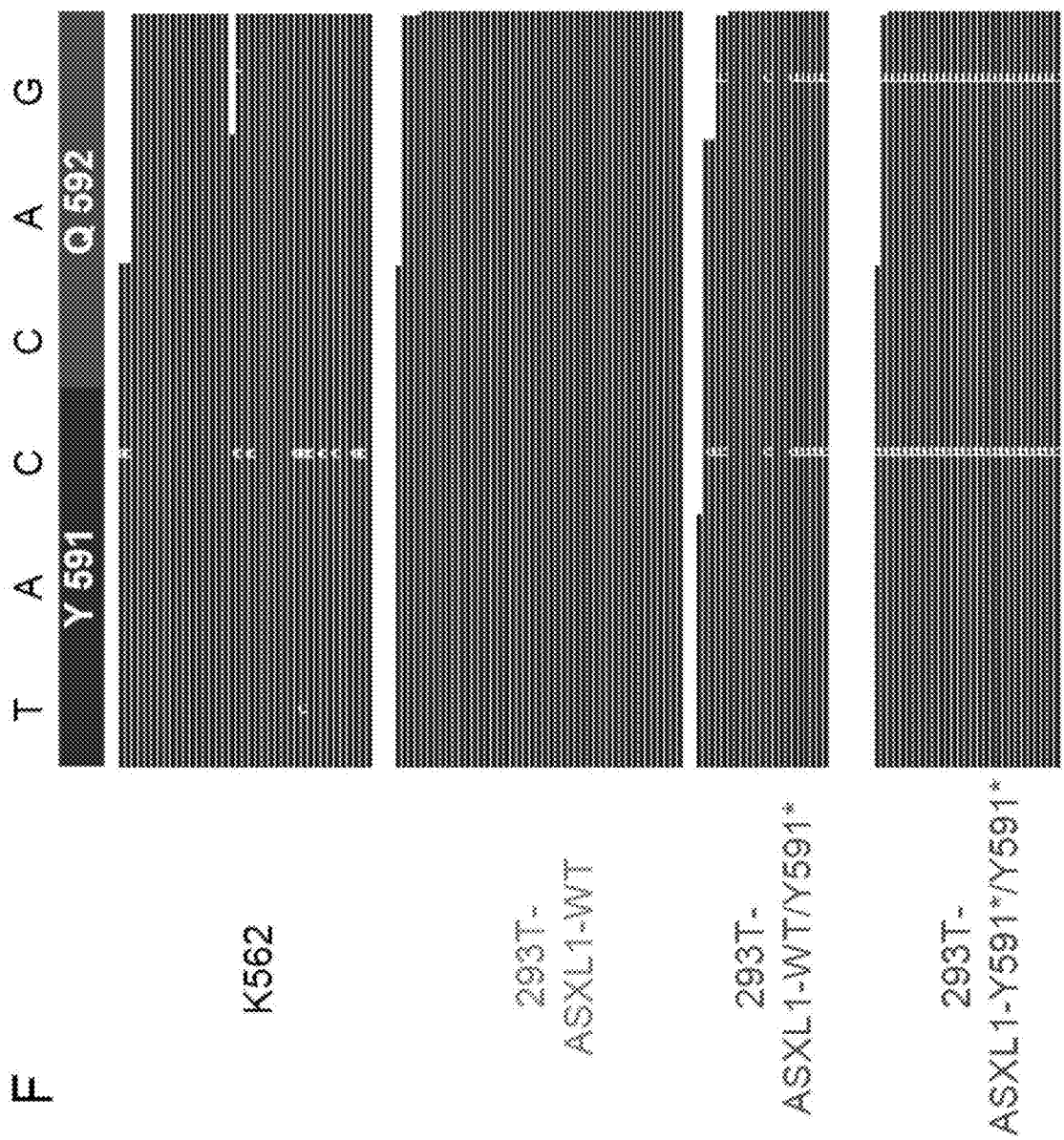
Figure 6:
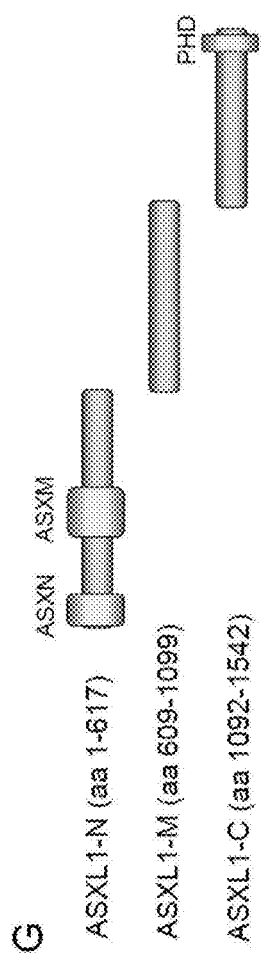
Figure 6:
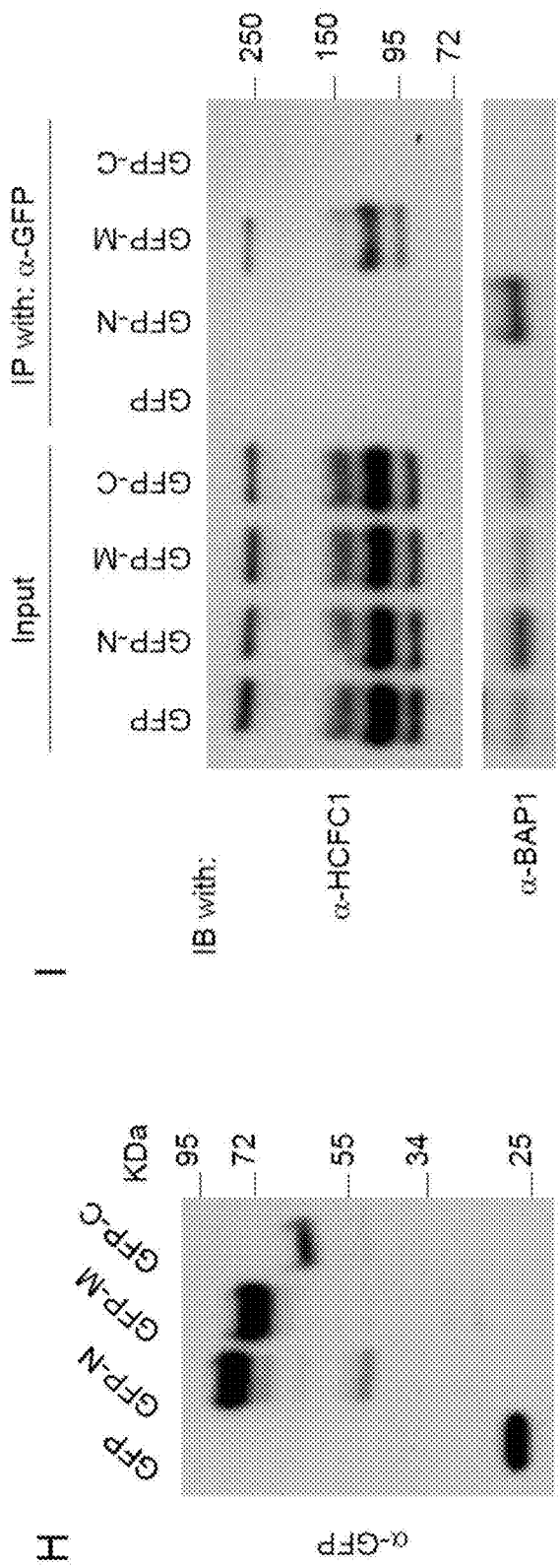

FIG. 6. Generation of anti-ASXL1-NTD antibody A) Mutation status of K562 cell line. B) Schematic of human ASXL1 protein and the antigen peptide for generation of the polyclonal antibody. C) Whole-cell lysates were used for western blot with ASXL1-NTD antibody in 293T and K562 cells, n=3. ASXL1 gene was knocked down in K562 cells by two different shRNA. The real-time PCR (D) and western blot (E) was performed to confirm the knocking down efficiency, n=3. F) Mutations status of ASXL1 gene in K562, 293T-ASXL1-WT, 293T-ASXL1-Y591* mutant cells. G) Schematic diagram depicting the domain organization of ASXL1 protein. The indicated fragments were sub-cloned as a GFP-tag fusion into pLNCX plasmid. Whole-cell lysates were used for immunoprecipitation with GFP antibodies followed by immunoblotting for GFP (H), HCFC1 and BAP1 (I) in cells transfected with empty vector (GFP) or ASXL1 truncations in (G), n=3.

Figure 7:
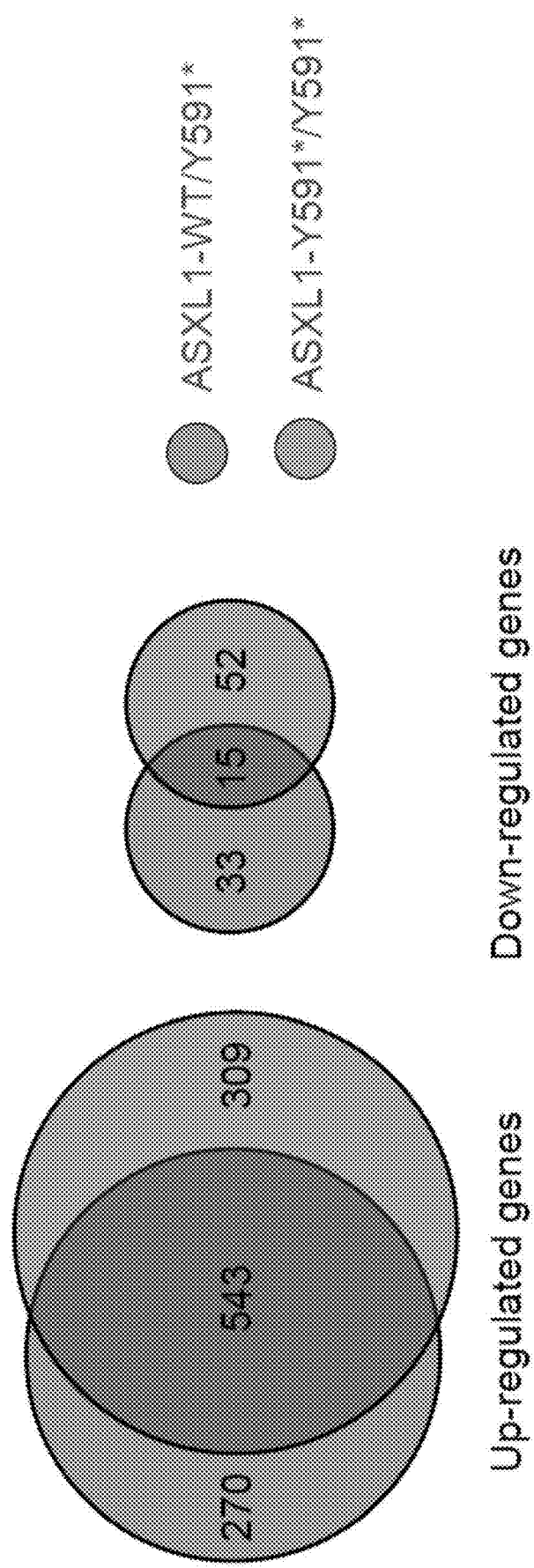

FIG. 7. Truncated ASXL1 drives transcription Venn diagram showing genes that are up/down-regulated by ASXL1 mutation (p<0.01, fold change>2), n=2, P-value from a two-tailed unpaired t-test is shown.

Figure 8:
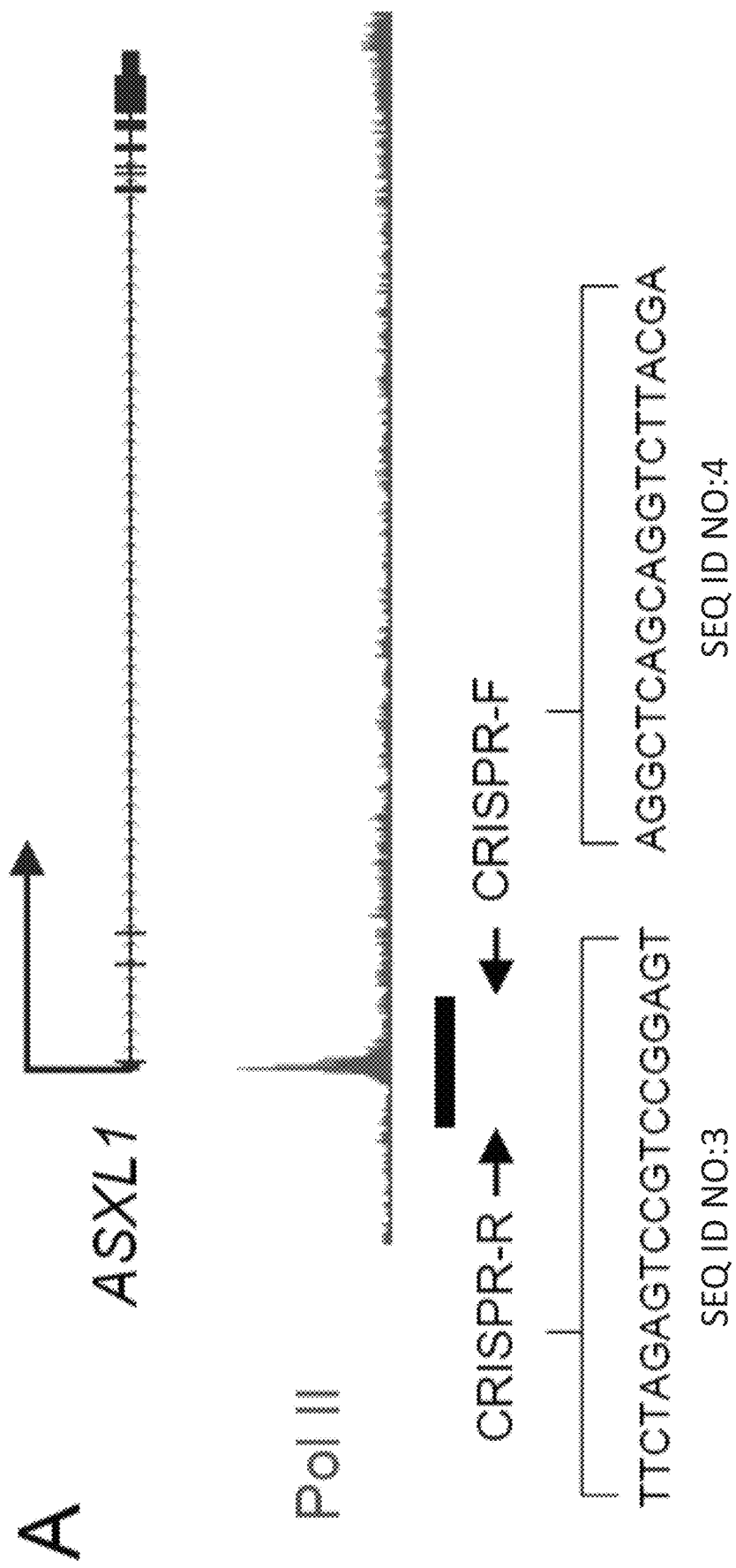
Figure 8:
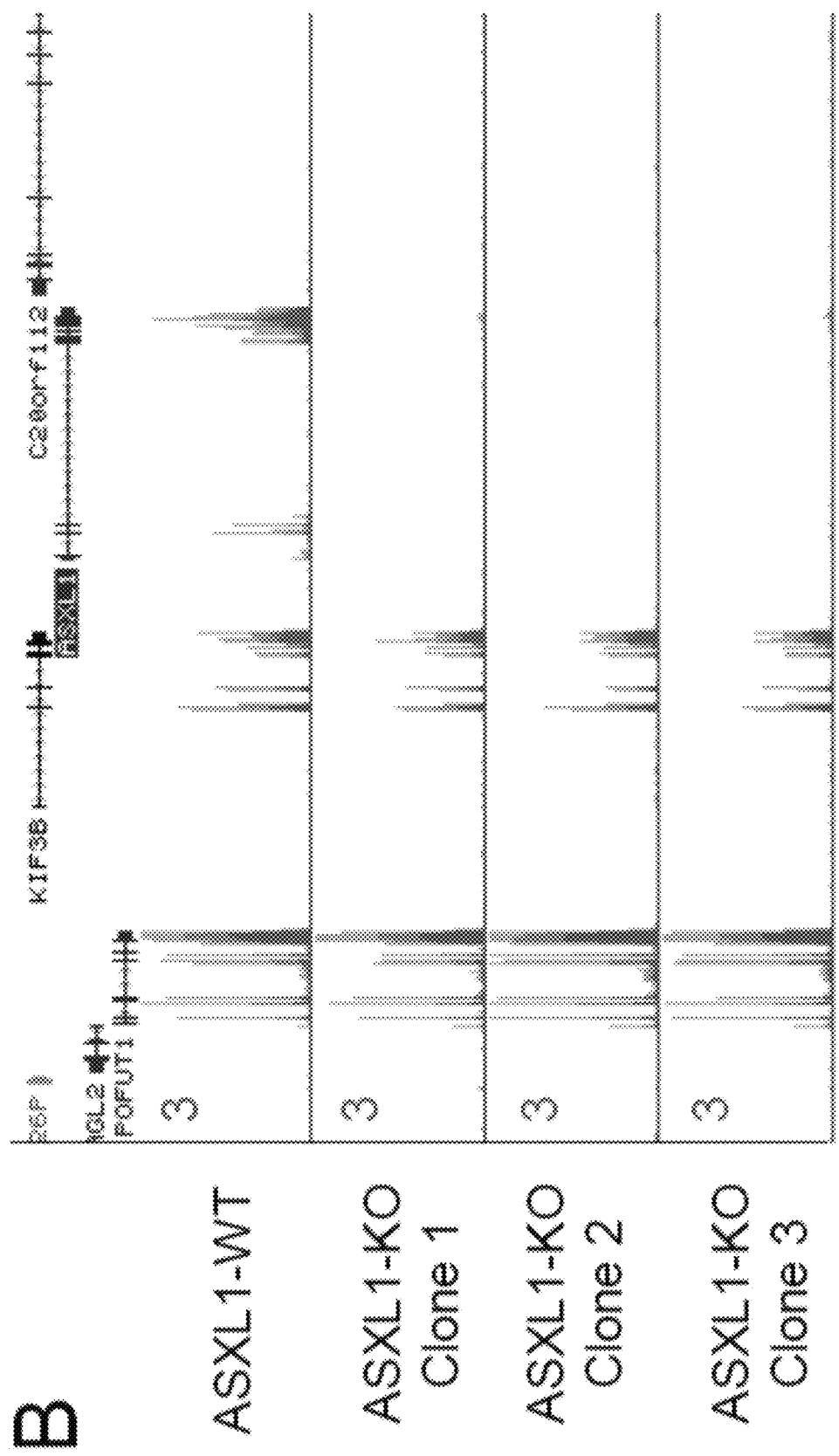
Figure 8:
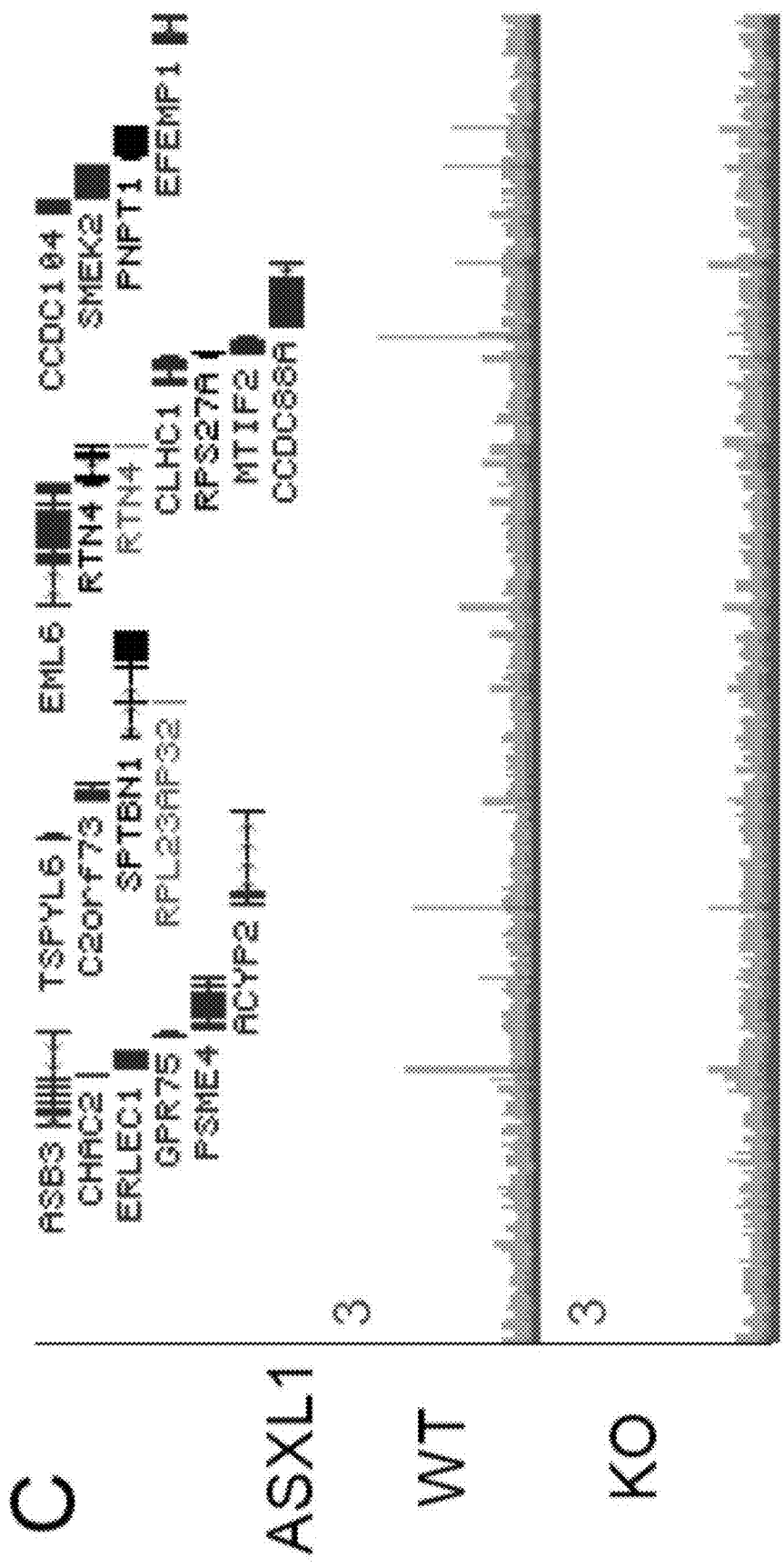
Figure 8:
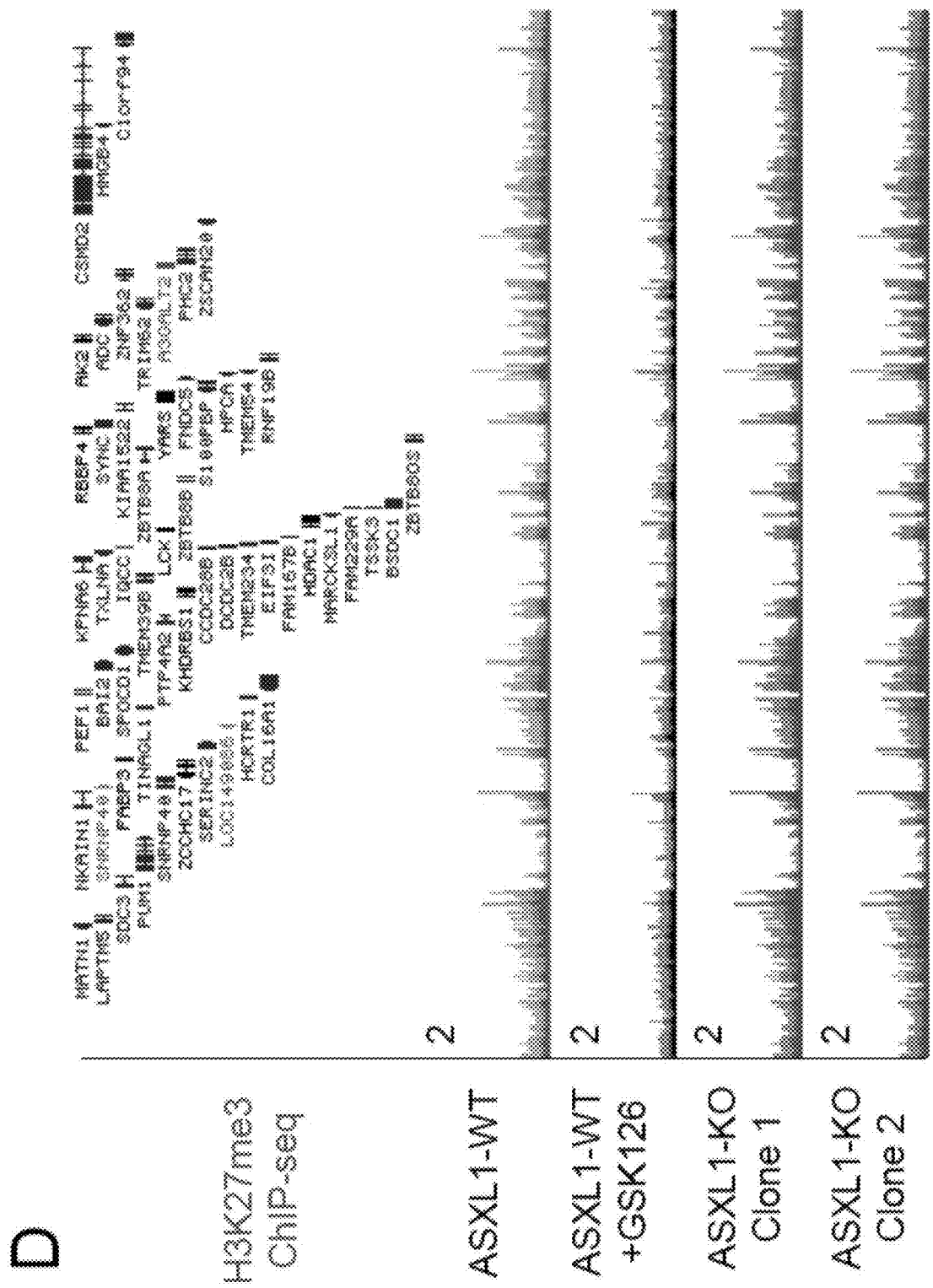
Figure 8:
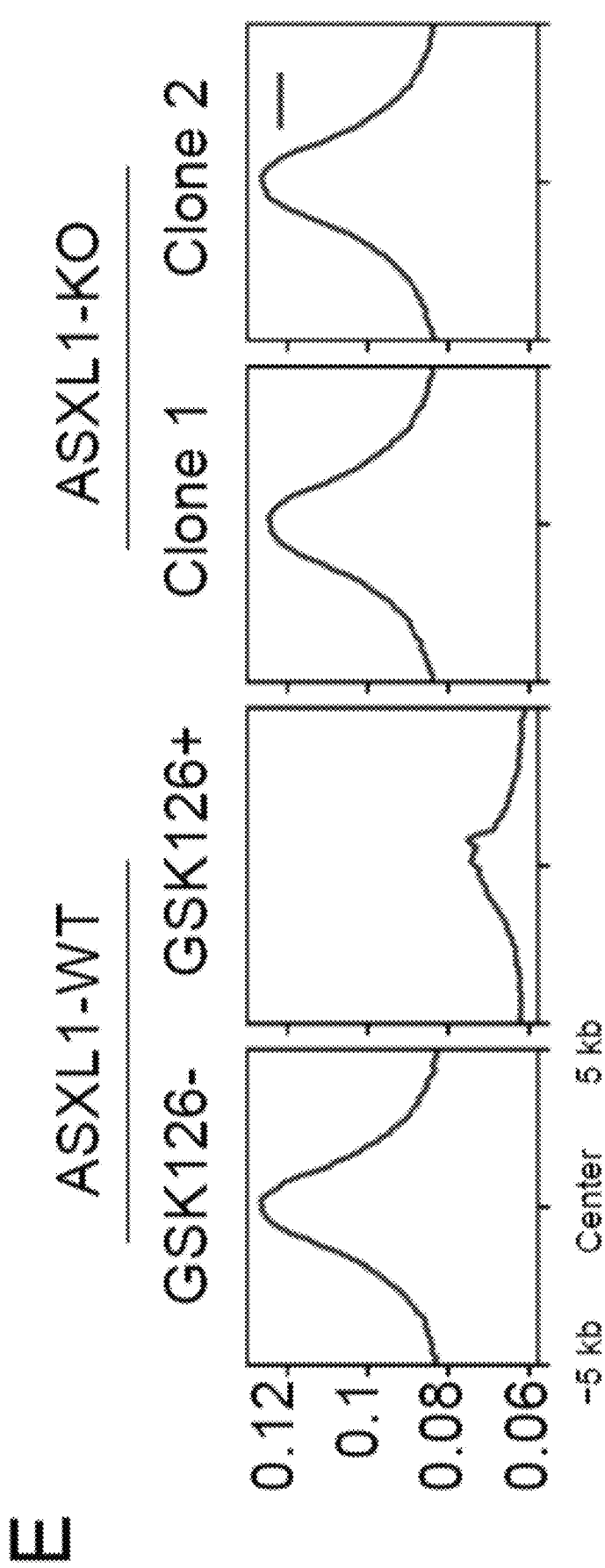
Figure 8:
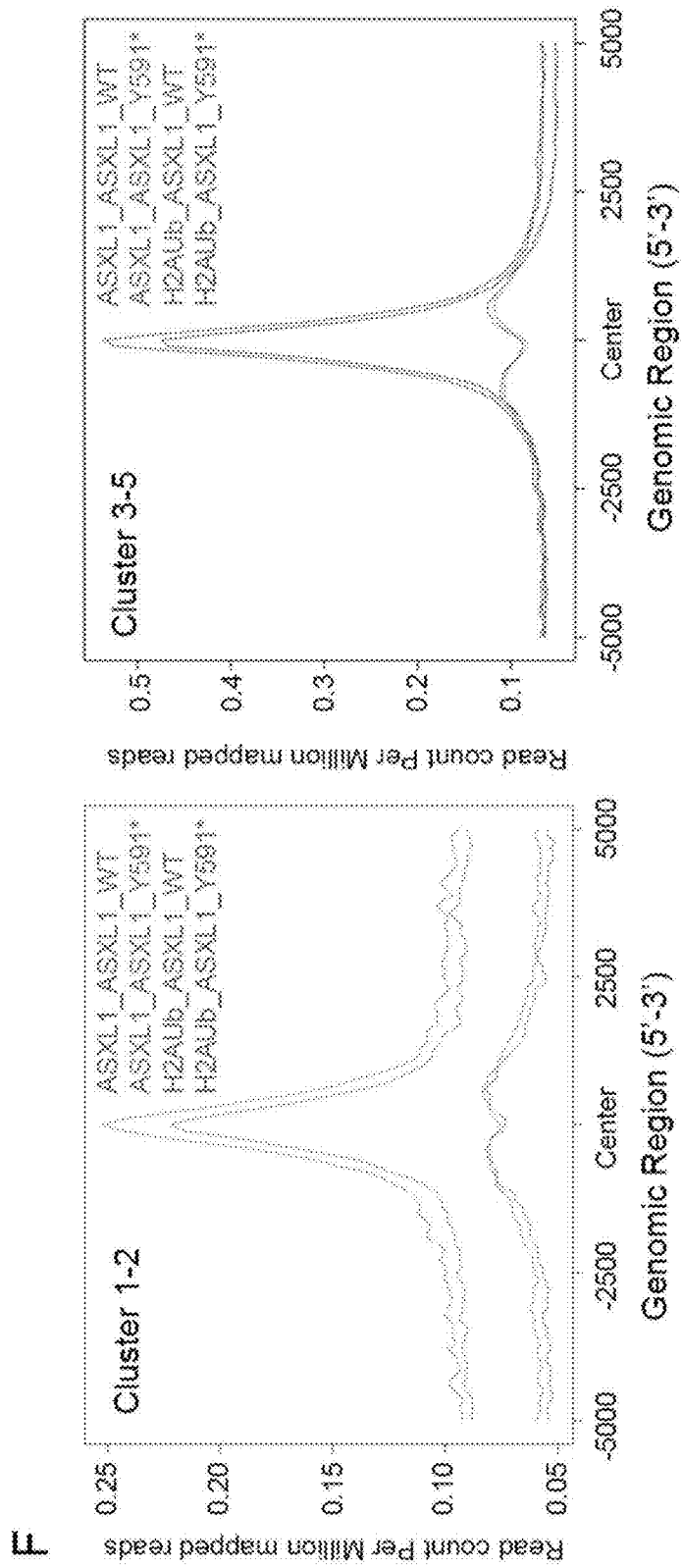
Figure 8:
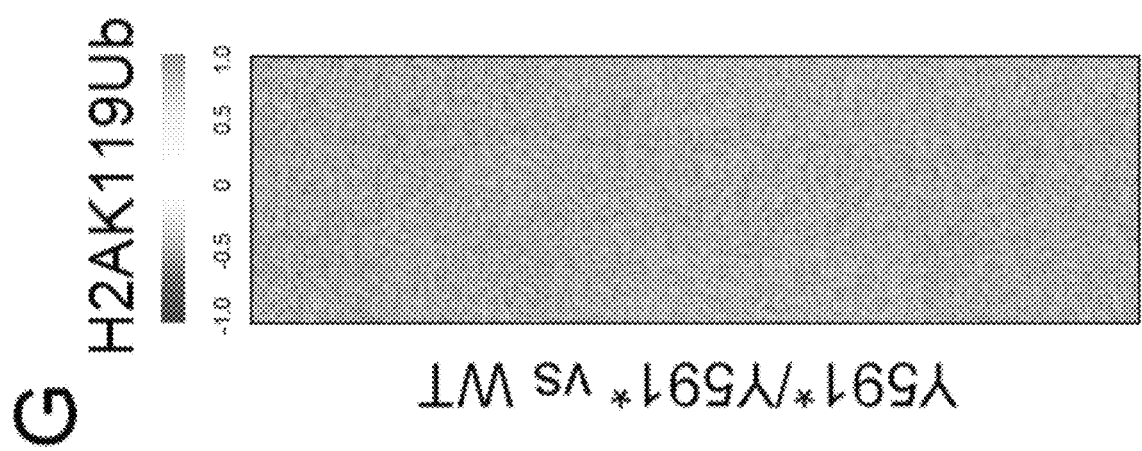

FIG. 8. Genome-wide binding of ASXL1 mutants A) Schematic of the human ASXL1 gene locus and the CRISPR gRNA designed to target promoter and Exon 1 of the ASXL1 gene. B) RNA-seq was performed in ASXL1-WT and ASXL1-KO cells, and the representative tracks show the depletion of ASXL1 gene in CAL51 cells, n=2. C) ChIP-seq track example shows the specificity of ASXL11 antibodies in ASXL1-WT and ASXL1-KO cells. D) ChIP-seq track example shows the occupancy of H3K27me3 level in ASXL1-WT, ASXL1-WT-GSK126-treated and ASXL1-KO cells. E) The average plot show the H3K27me3 levels in ASXL1-WT, ASXL1-WT-GSK126-treated and ASXL1-KO cells. F) The metaplot shows ASXL1 and H2K119Ub peaks from ASXL1-WT and ASXL1-Y591* cells are centered on BAP1 peaks at Cluster 1-2 (left) and Cluster 3-5 (right) loci. G) ChIP-seq analysis of H2AUb level in ASXL1-WT and ASXL1-Y591* cells at BAP1 binding regions.

Figure 9:
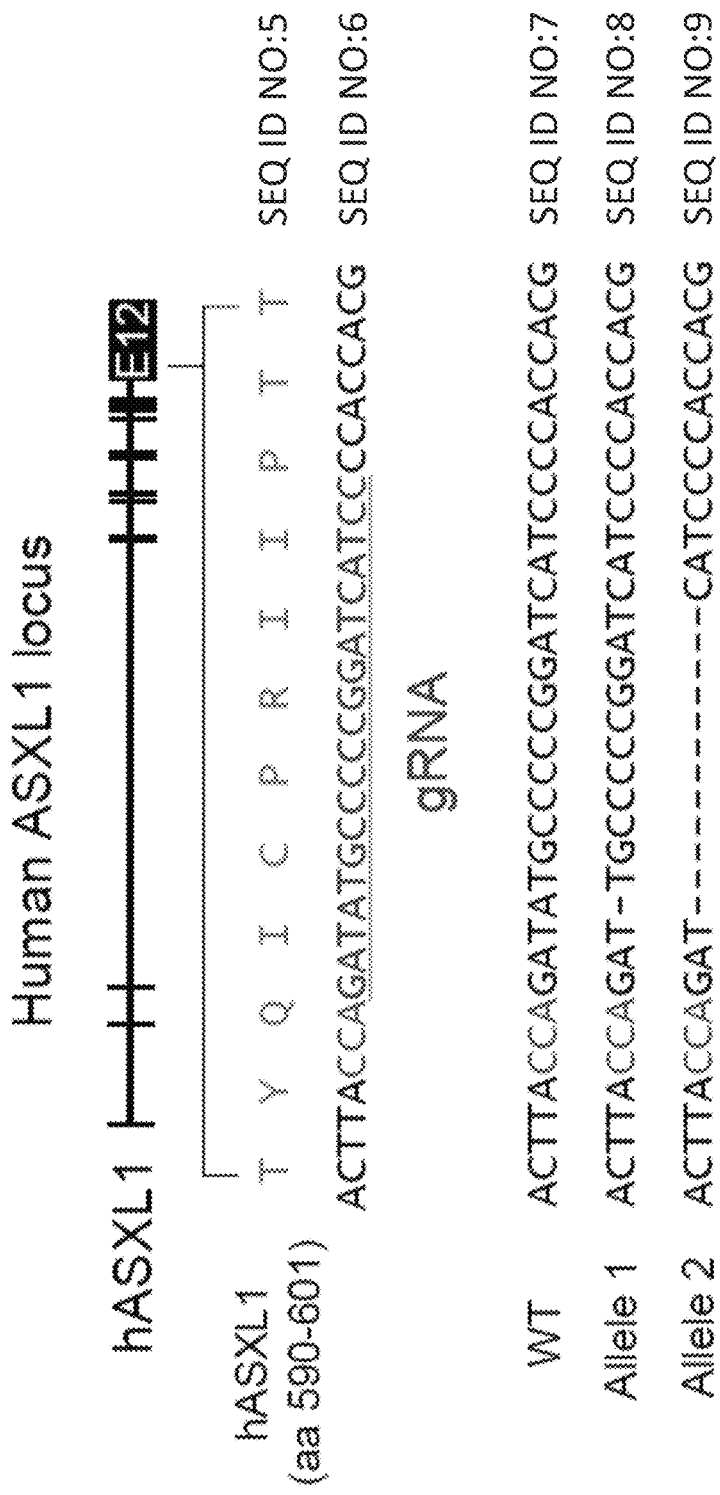
Figure 9:
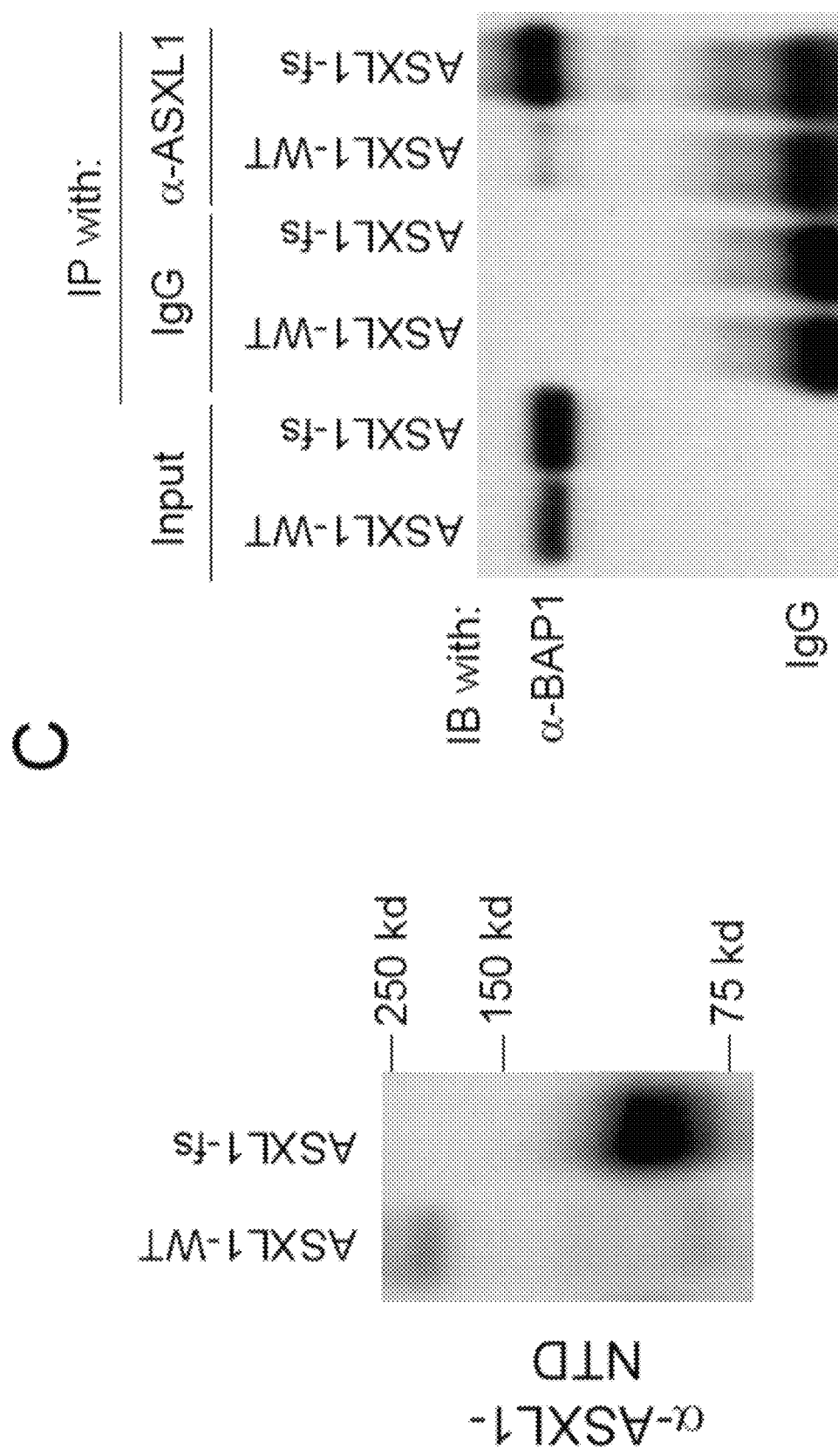
Figure 9:
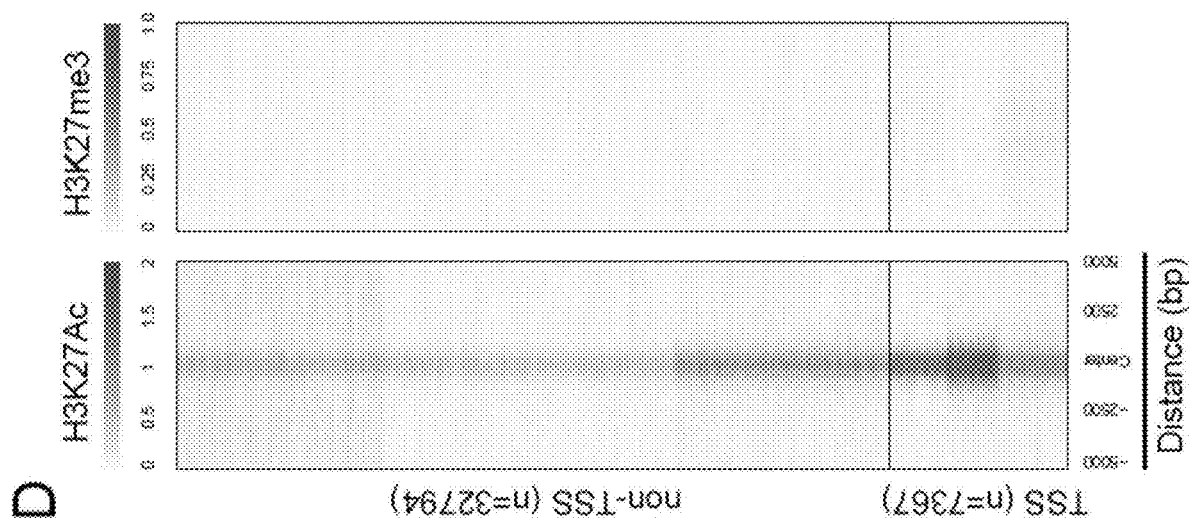
Figure 9:
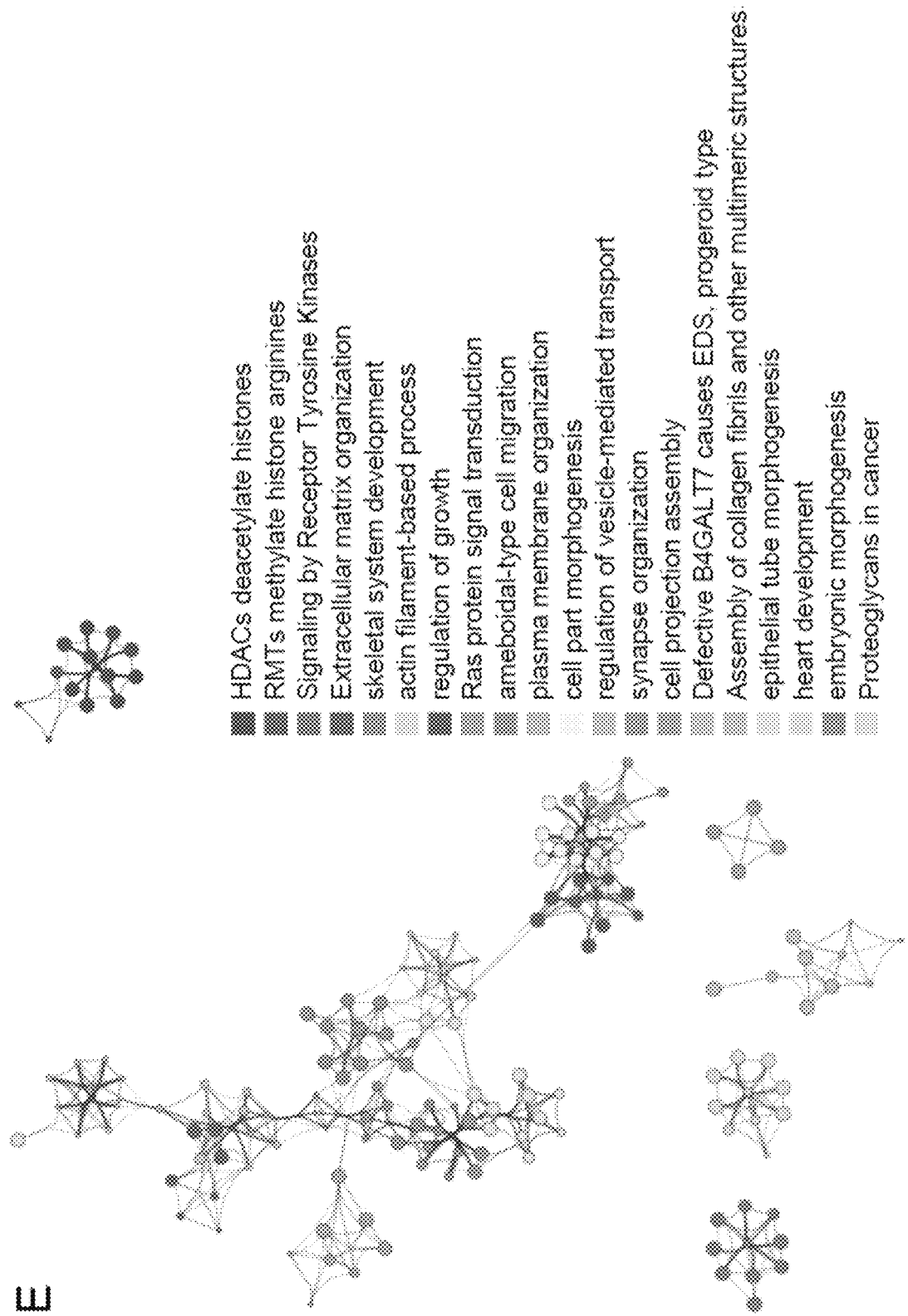

FIG. 9. GOF ASXL1 mutants stabilizes BAP1 and increases BAP1 recruitment A) Exon 12 of the ASXL1 gene was chosen for targeting with CRISPR-CAS9. The sequence of mutated allele is shown containing frame-shift mutations. B) Whole-cell lysates were used for western blot with ASXL1-NTD antibody in THP1-ASXL1-WT and THP1-ASXL1-fs cells, n=3. C) Whole-cell lysates were used for immunoprecipitation with ASXL1-NTD antibodies followed by immunoblotting for BAP1 (I) in cells expressing wild-type ASXL1 or frame-shift ASXL1 truncations, n=3. D) The heat map shows the occupancy of H3K27Ac and H3K27me3 level at BAP1 binding loci. E) Pathway analysis of the significantly up-regulated genes in ASXL1-fs cells was performed with Metascape, n=2.

Figure 10:
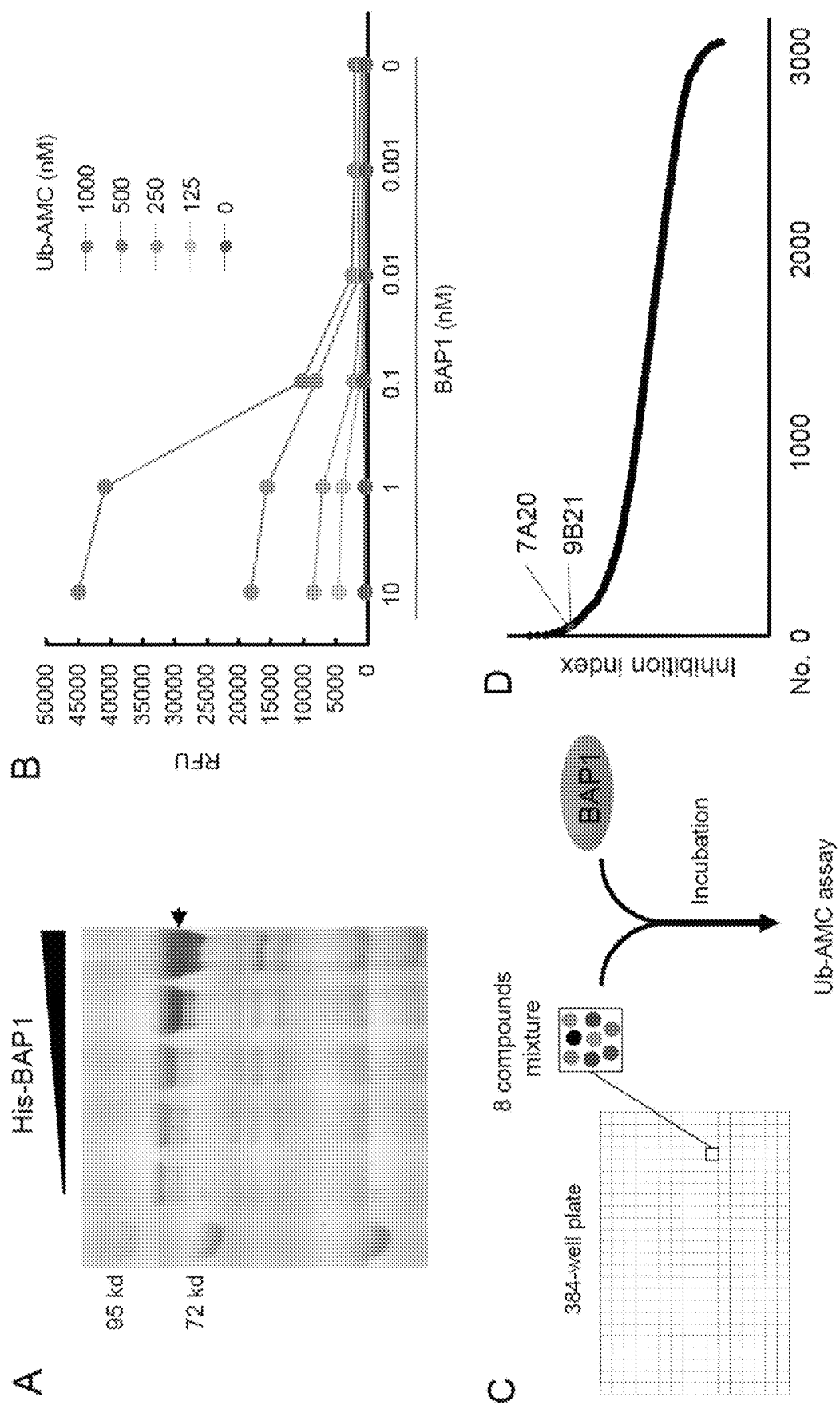
Figure 10:
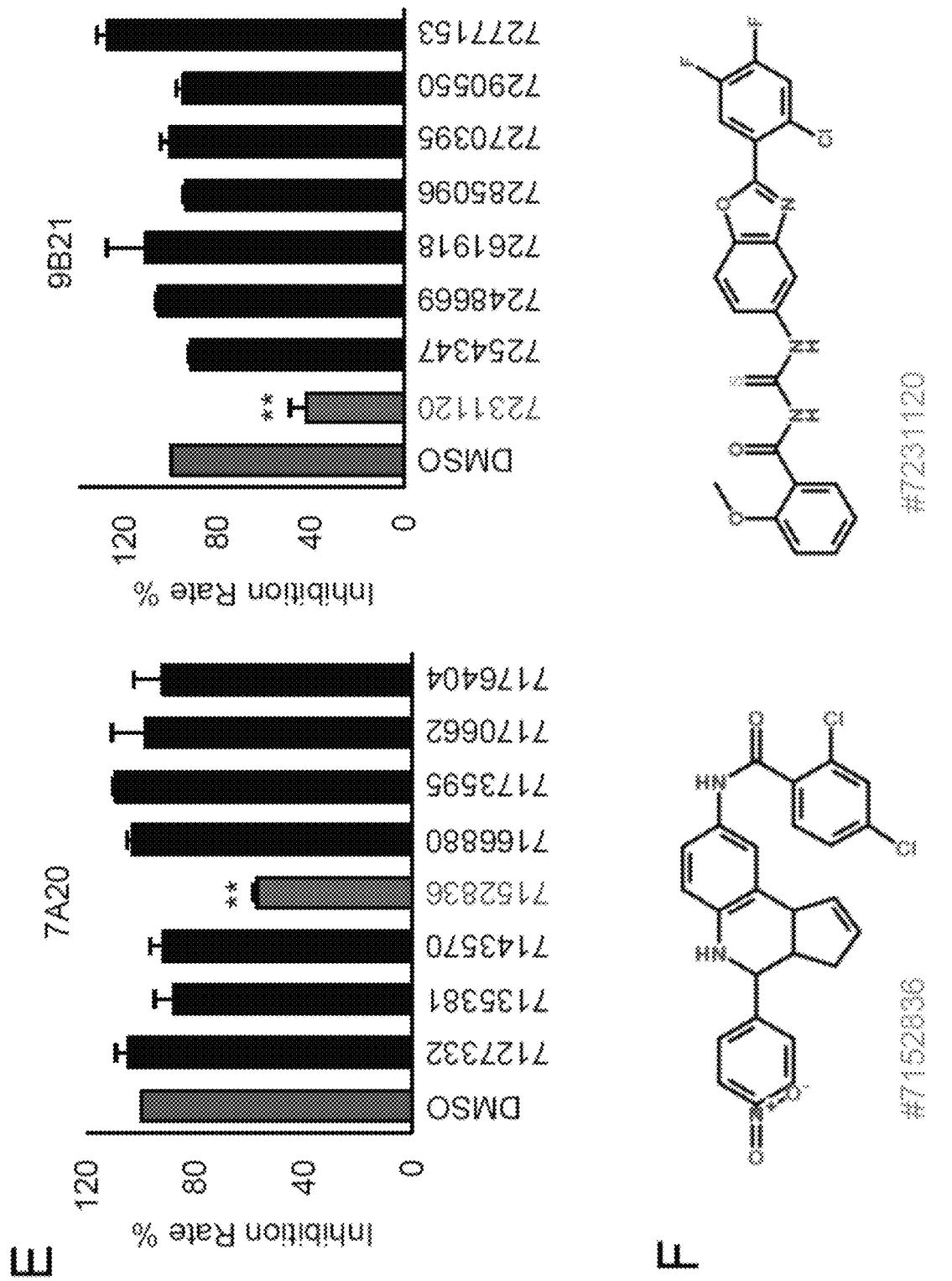
Figure 10:
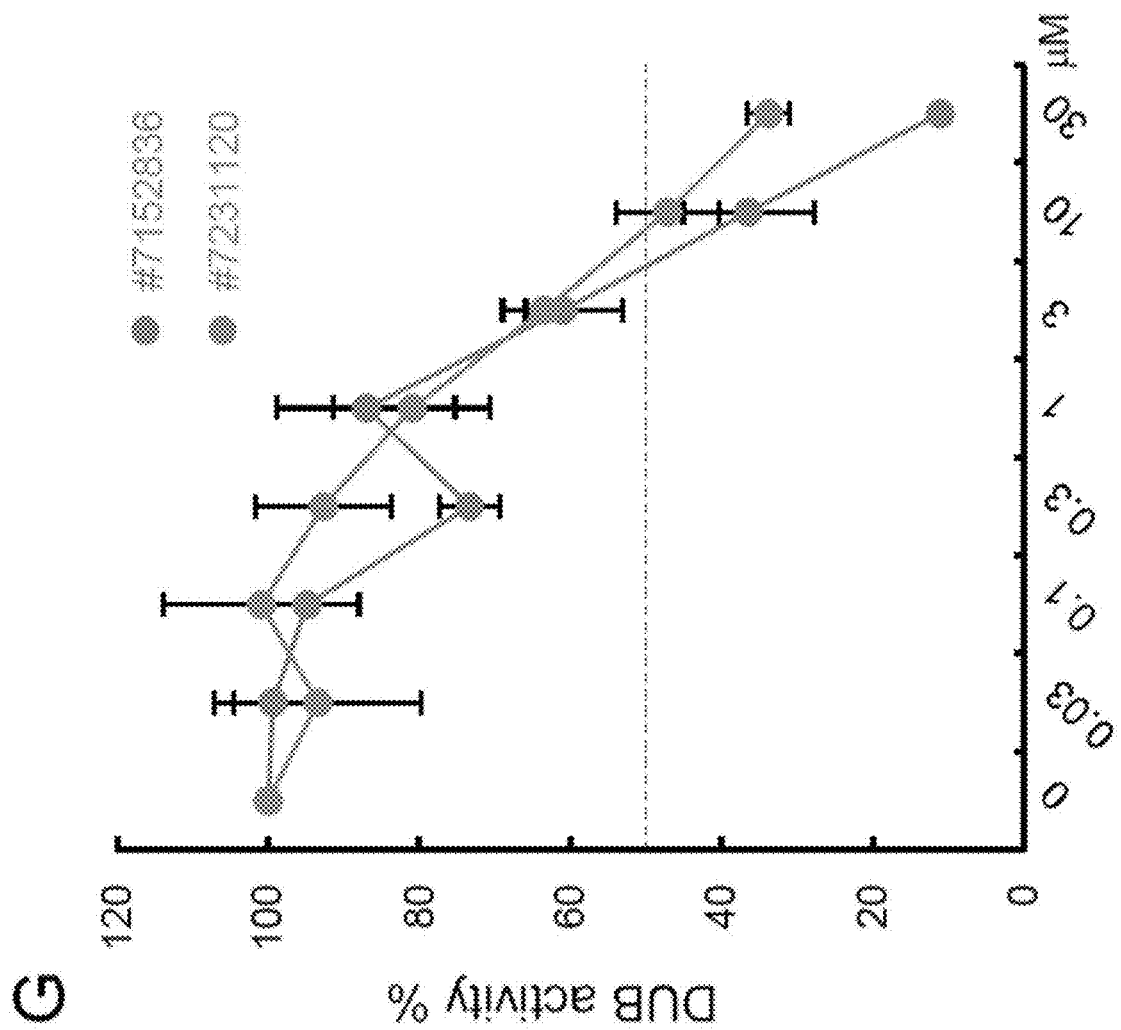

FIG. 10. Small molecule screening for BAP1 inhibitor A) Purification of recombinant BAP1 from bacteria. B) Optimization of Ub-AMC assay with recombinant BAP1. C) Schematic diagram of small molecule screening platform. D) Inhibition index of the 3,000 of 8-compound mixtures by Ub-AMC assay. E) Inhibition effect of 7A20 and 9B21 mixture by Ub-AMC assay. F) Structure of Compound #7152836 and #7231120. G) Dose-dependent inhibition of BAP1 activity by Compound #7152836 and #7231120 in Ub-AMC assay.

Figure 11:
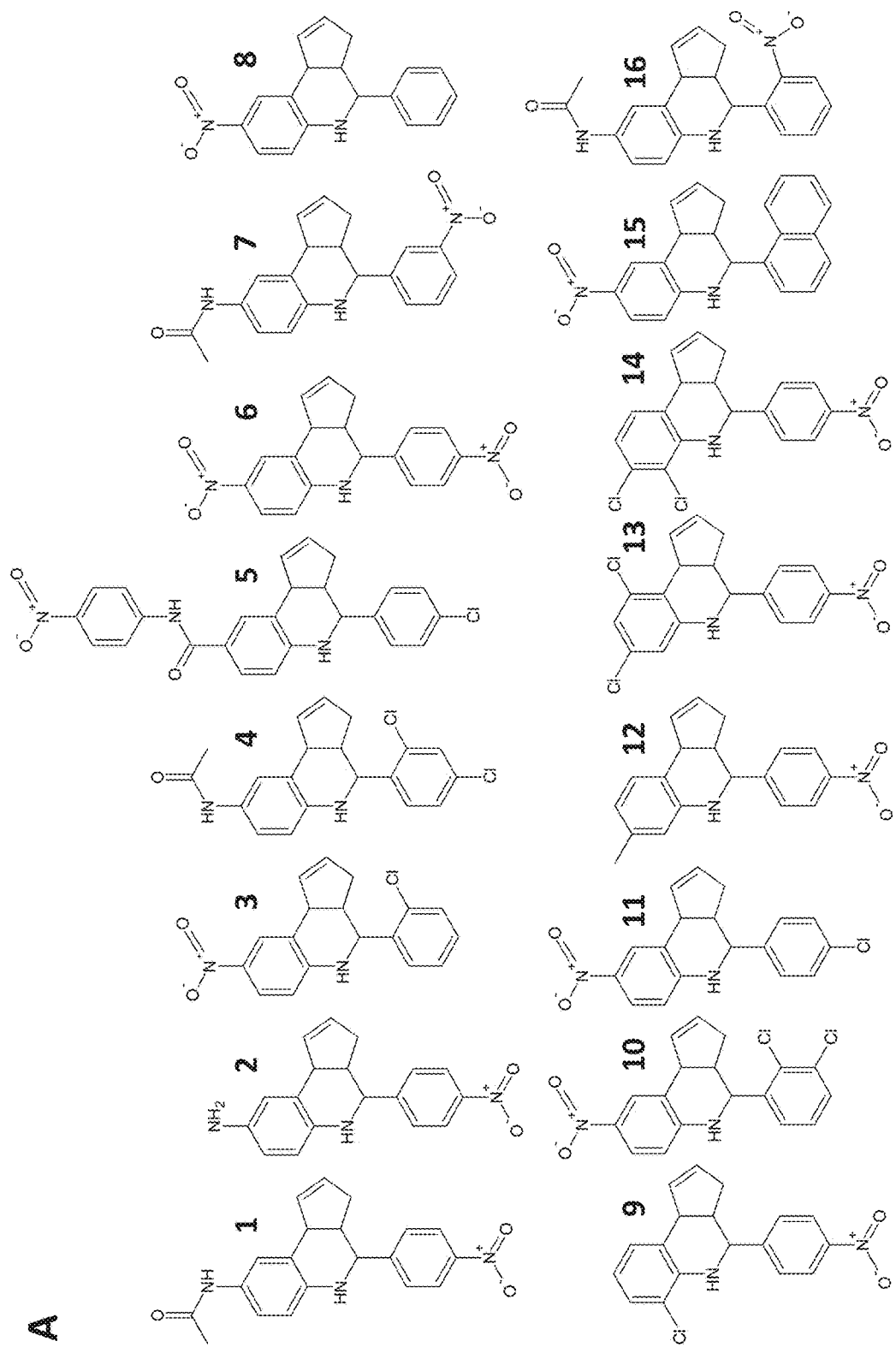
Figure 11:
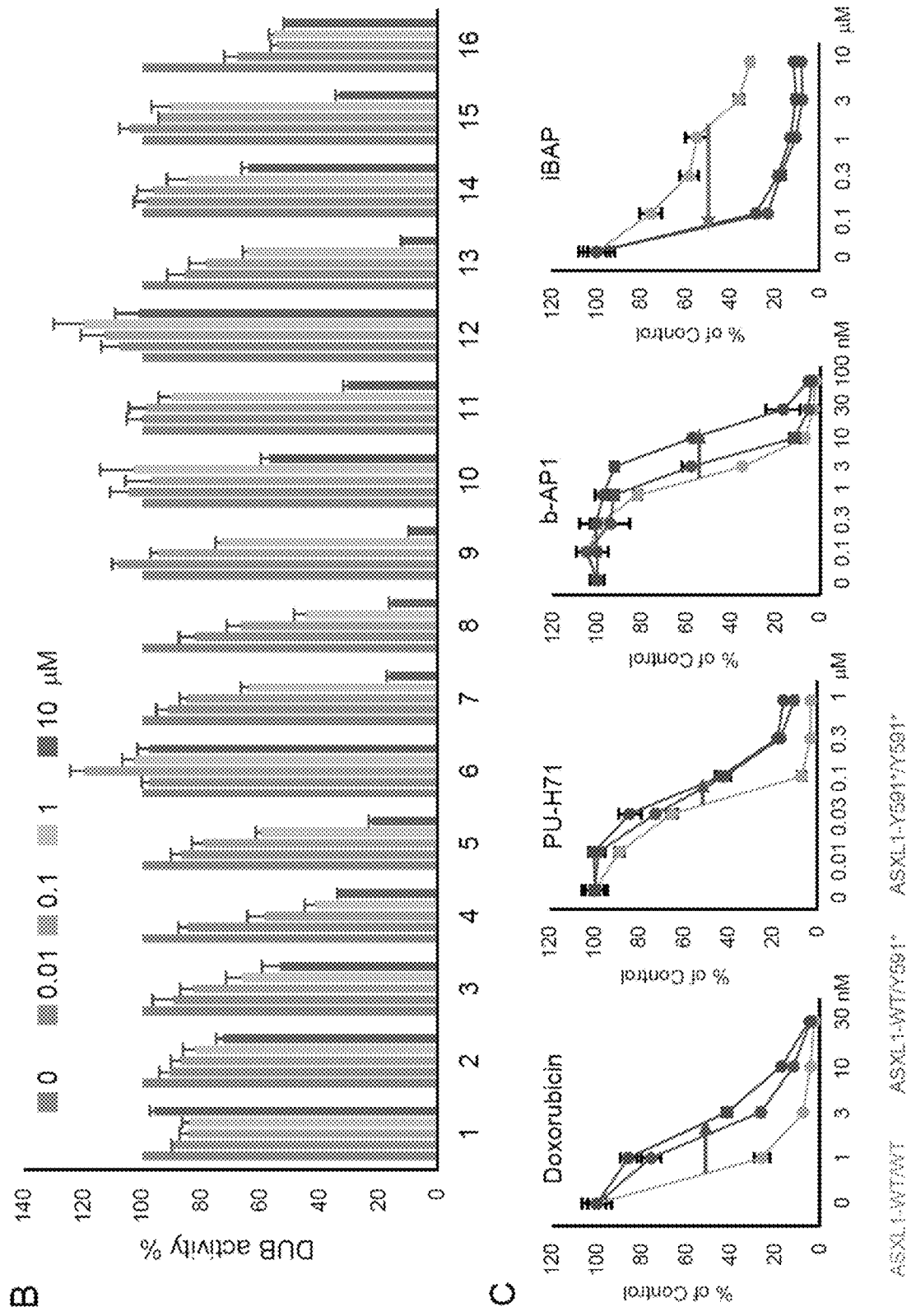

FIG. 11. Analog for compound #7152836 A) Structure of 16 analogs for compound #7152836. B) Dose-dependent inhibition of BAP1 activity the analogs in (A) in Ub-AMC assay. C) 293T-ASXL1-WT, 293T-ASXL1-Y591* mutant cells were treated with different concentrations of Doxorubicin, HSP90 inhibitor PU-H71, UCHL5 inhibitor b-AP1 and iBAP for 72 hours. The cell viability was determined by cell counting assay.

Figure 12:
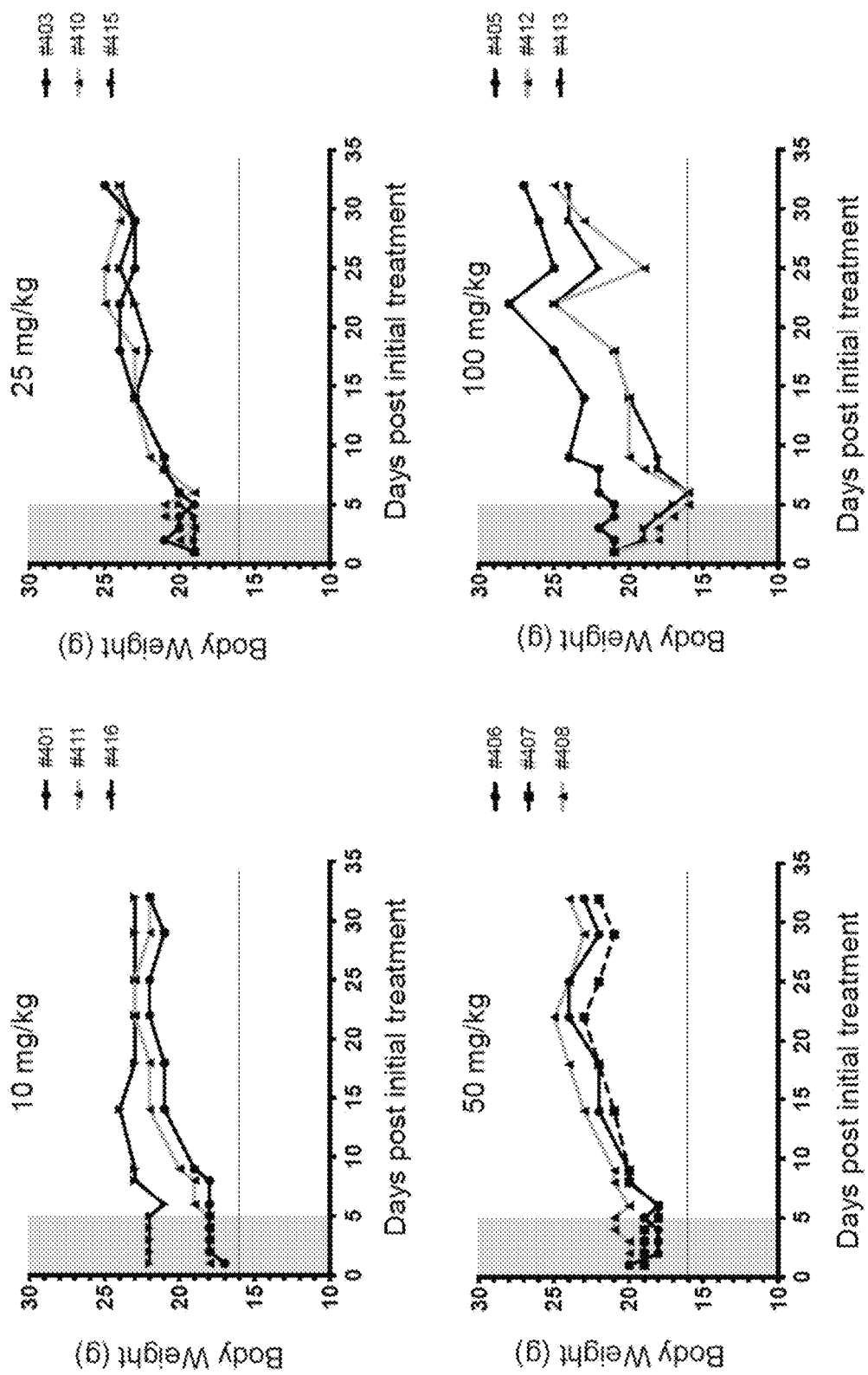

FIG. 12. Toxicity test for iBAP in vivo. NSGS mice were treated with different dosage (10, 25, 50 and 100 mg/kg) of iBAP once per day for five days. The body weight of mice from each group was measured.

DETAILED DESCRIPTION

The present invention is described herein using several definitions, as set forth below and throughout the application.

Definitions

Unless otherwise specified or indicated by context, the terms "a", "an", and "the" mean "one or more." For example, "a compound" and a "therapeutic agent" should be interpreted to mean "one or more compounds" and "one or more therapeutic agents," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus <10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The disclosed subject matter relates to methods, compounds and compositions, for inhibiting the activity of the BAP1 histone H2A deubiquitinase (DUB) complex, for example, to treat cancers associated with BAP1 complex activity. BAP1, or BRCA1-associated protein 1, is a tumor suppressor that is deleted and mutated in a number of cancers. (See Murali et al., Tumours associated with BAP1 mutations," Pathology 45, 116-126 (2013); and Carbone et al., "BAP1 and cancer," Nat. Rev. Cancer, 153-159 (2013), the contents of which are incorporated herein by reference in their entireties). BAP1 is a chromatin-associated protein that is assembled into large multiprotein complexes containing several transcription factors and co-factors, including ASXL1, and BAP1 complexes have been shown to regulate the expression of genes involved in cell proliferation. (See Bott et al., "The nuclear deubiquitinase BAP1 is commonly inactivated by somatic mutations and 3p21.1 losses in malignant pleural mesothelioma," Nat. Genet. 43, 668-672 (2011); Yu et al., "The ubiquitin carboxyl hydrolase BAP1 forms a ternary complex with YY1 and HCF-1 and is a critical regulator of gene expression," Mol. Cell. Biol. 30, 5071-5085 (2010); and Pan et al., "BAP1 regulates cell cycle progression through E2F1 target genes and mediates transcriptional silencing via H2A monoubiquitination in uveal melanoma cells. Int. J. Biochem," Cell Biol. 60, 176-184 (2015); the contents of which are incorporated by reference in their entireties). ASXL1 is frequently mutated and/or truncated in various cancer types, such as myeloid malignancies, but most truncated ASXL1 proteins retain the N-terminal region required for interaction with BAP1. (See Scheuermann et al., "Histone H2A deubiquitinase activity of the Polycomb repressive complex PR-DUB," Nature 465, 243-247 (2010); and Katoh, "Functional and cancer genomics of ASXL family members. Br. J. Cancer 109, 299-306 (2013); the contents of which are incorporated herein by reference in their entireties." Although the ASXL1 interaction with BAP1 was initially revealed to be dispensable for leukemia development, it was recently shown that leukemia-associated mutations of ASXL1 lead to an aberrant enhancement of BAP1 activity. (See Abdel-Wahab et al., ASXL1 mutations promote myeloid transformation through loss of PRC2-mediated gene repression. Cancer Cell 22, 180-193 (2012); and Balasubramani et al., "Cancer-associated ASXL1 mutations may act as gain-of-function mutations of the ASXL1-BAP1 complex. Nat. Commun. 6, 7307 (2015); the contents of which are incorporated herein by reference in their entireties).

As used herein, a "subject" may be interchangeable with "patient" or "individual" and means an animal, which may be a human or non-human animal, in need of treatment, for example, treatment by include administering a therapeutic amount of one or more therapeutic agents that inhibit the biological activity of one or more members of the BAP1 histone H2A deubiquitinase complex, otherwise referred to as the BAP1 complex.

A "subject in need of treatment" may include a subject having a disease, disorder, or condition that is responsive to therapy with an inhibitor of the biological activity of one or more members of BAP1 complex ay. For example, a "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus. In particular, cancers may include but are not limited to myeloid neoplasms such as acute myeloid leukemia (AML), myelodysplastic syndrome (MDS), myeloproliferative neoplasm (MPN), chronic myelomonocytic leukemia (CMML), and chronic myeloid leukemia (CML).

A "subject in need of treatment" may include a subject having a cancer that is characterized by a mutation in the ASXL1 gene. As would be understood in the art, the ASXL1 gene is the human homolog of the *Drosophila* Asx gene, a core subunit in the BAP1 histone H2A deubiquitinase complex. A "subject in need of treatment" may include but is not limited to a subject having a myeloid neoplasm and further having a mutation in the ASXL1 gene. Optionally, the ASXL1 mutation results in a frame-shift ASXL1 truncation and/or optionally the ASXL1 mutation results in a gain-of-function mutation. Optionally, the ASXL1 mutation results in a frame-shift ASXL1 truncation where the truncated ASXL1 protein stabilizes the BAP1 complex, and/or enhances recruitment of the BAP1 complex to chromatin, and/or promotes the expression of numerous leukemia associated genes such as HMGN5, STAT5A, HOXA11, BCAR1, TWIST1 and MBD2.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

Chemical Entities

Chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-$C_6$ alkyl group). Exemplary alkylene groups include, but are not limited to —$CH_2$—, —$CH_2CH_2$—, —$CH_2CH_2CH_2$—, —$CH(CH_3)CH_2$—, —$CH_2CH(CH_3)CH_2$—, —$CH(CH_2CH_3)CH_2$—, and the like.

The term "halo" refers to a halogen atom or a halogen radical, for example, —F, —Cl, —Br, or —I.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. The term "heteroaryl" is art-recognized and refers to an aryl group in which carbon atom within a ring of the aryl group is substituted with a hetereoatom, which may include N, O, and S, for example. Unless specified otherwise, the aromatic ring or an aryl group or a heteroaryl group may be substituted at one or more ring positions with, for example, halogen, azide, alkyl, aralkyl, alkenyl, alkynyl, cycloalkyl, hydroxyl, alkoxy, amino, nitro, sulfhydryl, imino, amido or carboxyamido, carboxylic acid, —C(O)alkyl, —C(O)O-alkyl, carbonyl, carboxyl, thioalkyl, sulfonyl, sulfonamido, sulfonamide, ketone, aldehyde, ester, heterocyclyl, aryl or heteroaryl moieties, —$CF_3$, —CN, or the like. In certain embodiments, the aromatic ring or an aryl group or a heteroaryl group is substituted at one or more ring positions with halogen, alkyl, hydroxyl, or alkoxyl. In certain other embodiments, the aromatic ring or an aryl group or a heteroaryl group is not substituted, i.e., it is unsubstituted. In certain embodiments, the aromatic ring or an aryl group or a heteroaryl group is a 6-10 membered single ring structure or a bicyclic ring structure.

The term "arylalkyl" is art-recognized and refers to a radical defined as -alkyl-aryl, where "alkyl" and "aryl" are as defined herein. The term "heteroarylalkyl" is art-recognized and refers to a radical defined as -alkyl-heteroaryl, where "alkyl" and "heteroaryl" are as defined herein.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "carboxyalkyl" as used herein refers to the radical -alkyl-COOH, in which "alkyl" is an alkyl radical which may be straight chain or branched as described herein.

The term "amide" or "amido" or "amidyl" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pharmaceutical Compositions and Formulations

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given.

The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates the activity of the BAP1 complex may be administered as a single compound or in combination with another compound that modulates the activity of the BAP1 complex or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, a-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with the activity of the BAP1 complex, which may include but are not limited to cell proliferative diseases and disorders such as cancer. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating one or more of the aforementioned diseases or disorders.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Therapeutic Targeting of the BAP1 Complex in Cancer

The present inventors have disclosed methods, compounds, and compositions for treating diseases and disorders, including cell proliferative diseases and disorders such as cancer, which are characterized by therapeutic targeting of the BAP1 histone H2A deubiquitinase (DUB) complex, otherwise referred to as the BAP1 complex. In the disclosed methods, a subject having a disease or disorder, such as cancer, is administered a therapeutic amount of a therapeutic agent that inhibits the biological activity of the BAP1 histone H2A deubiquitinase (DUB) complex (i.e., the "BAP1 complex").

In some embodiments, the subject may have a cancer, such as a myeloid neoplasm. In particular, the subject may have a cancer selected from the group consisting of acute myeloid leukemia (AML), myelodysplastic syndrome (MDS), myeloproliferative neoplasm (MPN), chronic myelomonocytic leukemia (CMML), and chronic myeloid leukemia (CML).

In some embodiments, the subject may have a cancer which is further characterized by a mutation in the ASXL1 gene. The mutation may result in a truncated ASXL1 protein which exhibits a gain-of-function biological activity.

In the disclosed methods, a subject in need of treatment is administered a therapeutic agent that inhibits the biological activity of the BAP1 histone H2A deubiquitinase (DUB) complex (i.e., the "BAP1 complex"). In some embodiments, the therapeutic agent comprises a compound of the following formula or a suitable pharmaceutical salt or solvate thereof:

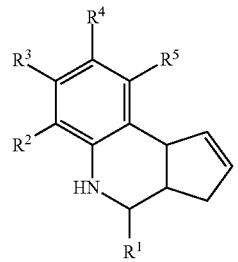

wherein:

$R^1$ is hydrogen, or aryl (e.g., phenyl or naphthyl) or heteroaryl (e.g., pyridinyl which is pyridin-2-yl, pyridin-3-yl, or pyridin-4-yl) optionally substituted at one or more positions with halo (e.g., fluoro or chloro) or nitro;

$R^2$ is selected from hydrogen and halo (e.g., fluoro or chloro);

$R^3$ is selected from hydrogen and halo (e.g., fluoro or chloro);

$R^4$ is selected from hydrogen, halo (e.g., fluoro or chloro), amino, nitro, alkylcarboxyamido (e.g., $CH_3C(O)NH-$), $R^6-C(O)NH-$ wherein $R^6$ is aryl (e.g. phenyl or naphthyl) or heteroaryl (e.g., pyridinyl which is pyridin-2-yl, pyridin-3-yl, or pyridin-4-yl) optionally substituted at one or more positions with halo or nitro (e.g., 2,4-dichlorophenyl-carboxyamido), or $R^6-NH-C(O)-$ wherein $R^6$ is aryl (e.g. phenyl or naphthyl or heteroaryl (e.g., pyridinyl which is pyridin-2-yl, pyridin-3-yl, or pyridin-4-yl) optionally substituted at one or more positions with halo (e.g., fluoro or chloro) or nitro (e.g., 4-nitrophenyl-carboxyamido); and $R^5$ is selected from hydrogen and halo (e.g., fluoro or chloro).

In some embodiments of the disclosed methods, a subject in need of treatment is administered a therapeutic amount of a compound selected from the following compounds or pharmaceutical salts or solvates thereof:

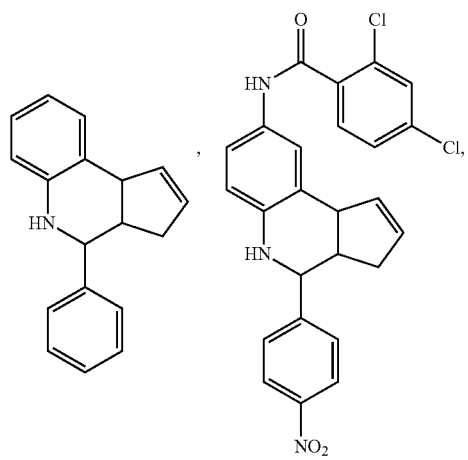

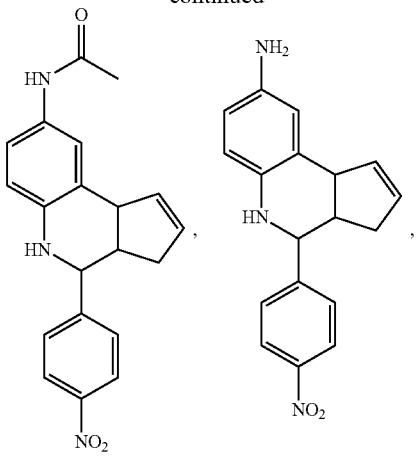
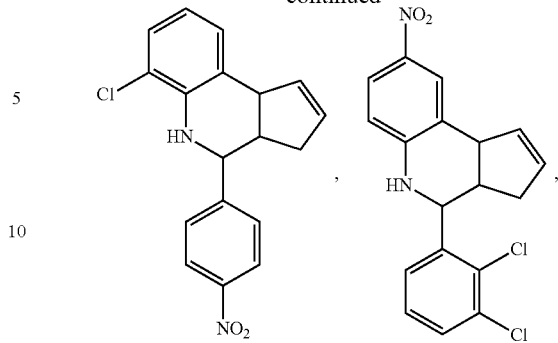
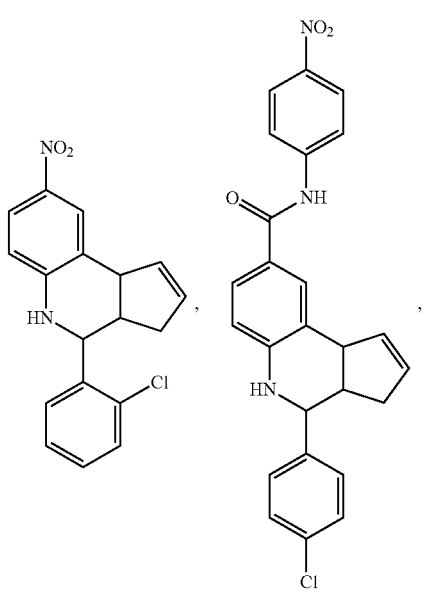
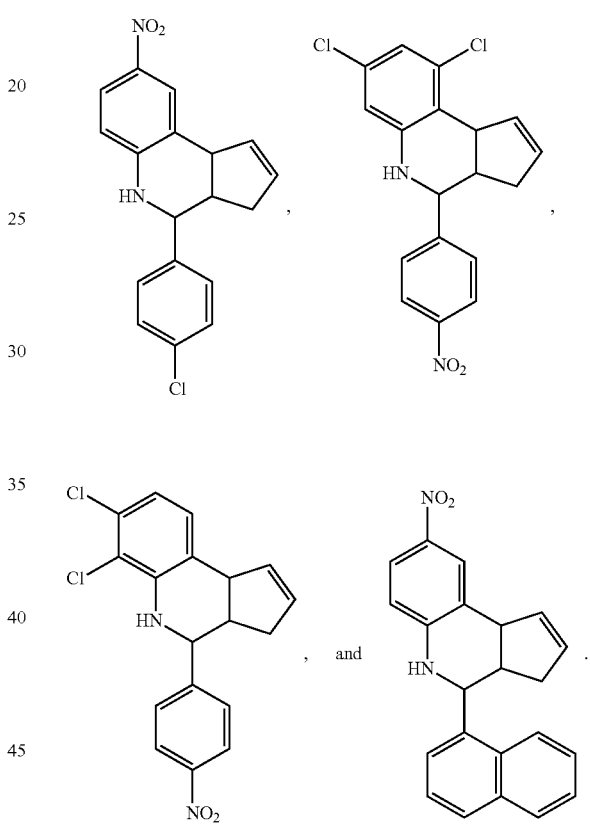
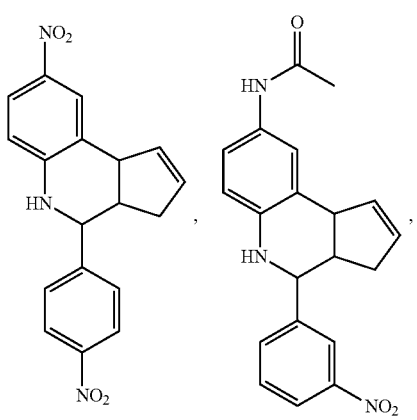
In other embodiments of the disclosed methods, a subject in need of treatment is administered a therapeutic agent which comprises a compound of the following formula or a suitable pharmaceutical salt or solvate thereof:
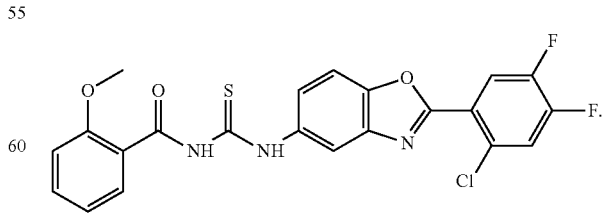
The compounds disclosed and contemplated herein may be synthesized by schemes that include, but are not limited to, the following scheme:

17

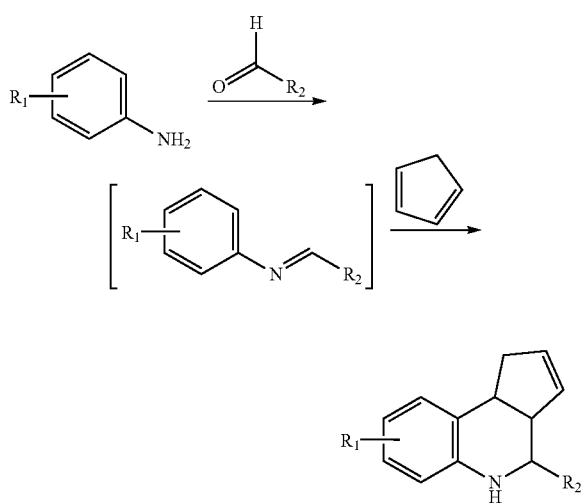

Illustrative Embodiments

The following Embodiments are illustrative and should not be interpreted to limit the scope of the claimed subject matter.

Embodiment 1. A method for treating cancer in a subject in need thereof, the method comprising administering to the subject a therapeutic amount of a therapeutic agent that inhibits the biological activity of the BAP1 histone H2A deubiquitinase (DUB) complex (BAP1 complex).

Embodiment 2. The method of embodiment 1, wherein the cancer is a myeloid neoplasm.

Embodiment 3. The method of embodiment 1 or 2, wherein the cancer is selected from the group consisting of acute myeloid leukemia (AML), myelodysplastic syndrome (MDS), myeloproliferative neoplasm (MPN), chronic myelomonocytic leukemia (CMML), and chronic myeloid leukemia (CML).

Embodiment 4. The method of any of the foregoing embodiments, wherein the subject has a mutation in the ASXL1 gene.

Embodiment 5. The method of embodiment 4, wherein the mutation results in a truncated ASXL1 protein.

Embodiment 6. The method of any of the foregoing embodiments, wherein the therapeutic agent comprises a compound of the following formula or a suitable pharmaceutical salt or solvate thereof:

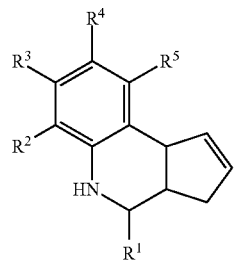

18 wherein:

$R^1$ is hydrogen, or aryl or heteroaryl optionally substituted at one or more positions with halo or nitro;

$R^2$ is selected from hydrogen and halo;

$R^3$ is selected from hydrogen and halo;

$R^4$ is selected from hydrogen, halo, amino, nitro, alkyl-carboxyamido (e.g., CH$_3$C(O)NH—), $R^6$—C(O)NH— wherein $R^6$ is aryl or heteroaryl optionally substituted at one or more positions with halo or nitro (e.g., 2,4-dichlorophenyl-carboxyamido), or $R^6$—NH—C(O)— wherein $R^6$ is aryl or heteroaryl optionally substituted at one or more positions with halo or nitro (e.g., 4-nitrophenyl-carboxyamido); and $R^5$ is selected from hydrogen and halo.

Embodiment 7. The method of embodiment 6, wherein the compound is selected from the following compounds or pharmaceutical salts or solvates thereof:

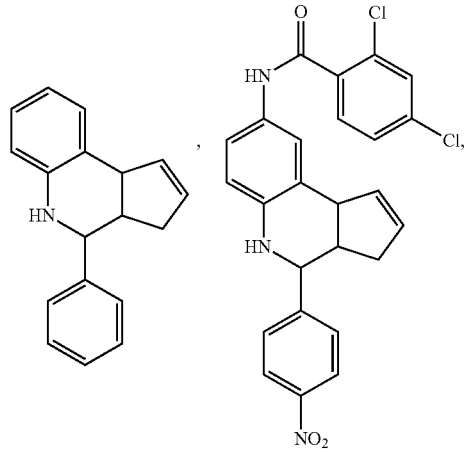

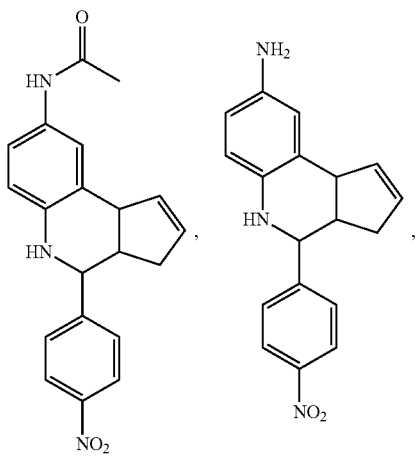

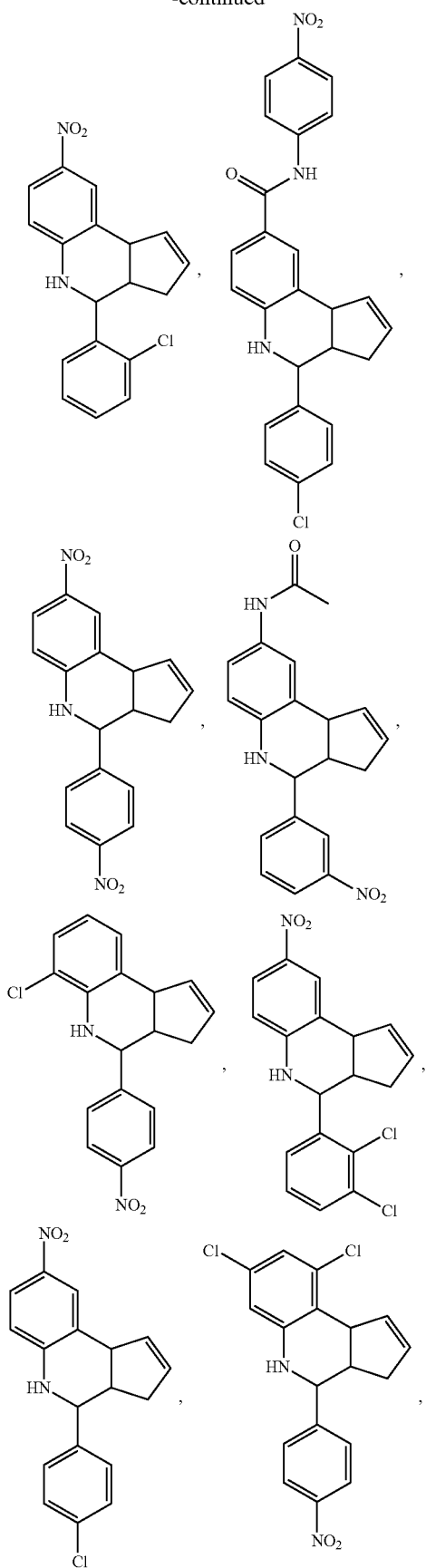

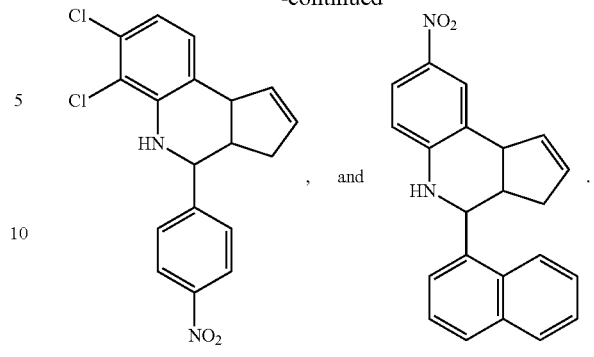

and

Embodiment 8. The method of any of embodiments 1-5, wherein the therapeutic agent is a compound of the following formula or a suitable pharmaceutical salt or solvate thereof:

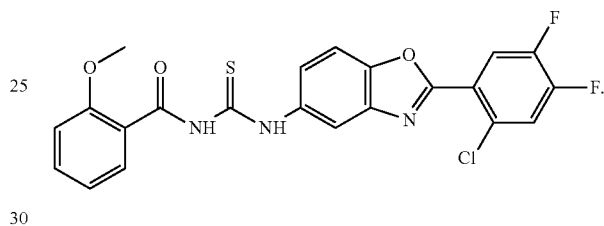

EXAMPLES

The following Examples are illustrative and should not be interpreted to limit the scope of the claimed subject matter.

Title—Epigenetic targeted therapy of leukemia through a BAP/Asxl1 axis

Abstract

The ASXL1 gene is the human homolog of the Drosophila Asx gene, a core subunit in the BAP1 histone H2A deubiquitinase complex. Mutations of ASXL1 occur in myeloid neoplasms, including acute myeloid leukemia (AML), myelodysplastic syndrome (MDS), myeloproliferative neoplasm (MPN), chronic myelomonocytic leukemia (CMML), and chronic myeloid leukemia (CML) and are uniformly associated with poor prognosis. However, the molecular basis of the role of ASXL1 mutations in regulating the BAP1 complex during leukemogenesis remains unclear. Here we demonstrate that cancer-associated frame-shift ASXL1 truncations, originally proposed to act as destabilizing loss-of-function mutations, in fact encode stable gain-of-function proteins. Truncated ASXL1 stabilizes BAP1 and enhances BAP1 complex recruitment to chromatin and promotes the expression of numerous leukemia associated genes such as HMGN5, STAT5A, HOXA11, BCAR1, TWIST1 and MBD2. Chemical inhibition of BAP1 fully rescues these changes in the gene expression pattern in leukemic cells inhibiting tumor progression. This study represents a breakthrough advance in our understanding of the molecular mechanisms of ASXL1 mutations in leukemic pathogenesis and identifies small molecular inhibitors of BAP1 function as a potential targeted therapy for leukemia.

Introduction

Mutations in the genes encoding for the epigenetic enzymes are frequently detected in human diseases, especially cancer (1-3). Perturbation of chromatin modifiers such as DNA methyltransferases, the Ten-eleven Translocation (TET) enzymes, histone protein lysine methyltransferases (KMTs), and others through mutations and translocations are a common mechanism driving tumorigenesis (4-6). A recent study demonstrated the existence of a balance between the trithorax/COMPASS family of histone H3 lysine 4 (H3K4) methyltransferases and the Polycomb group (PcG) family of histone H3K27 methyltransferases and demethylase and H2AK119 deubiquitinase through the function of the BAP1 complex (2).

ASXL1 gene encodes a 1084 amino acid nuclear protein that is a core component in histone H2A deubiquitinase BAP1 complex (7, 8). ASXL1 is a one of the most frequently mutated genes in malignant myeloid diseases and these mutations are associated with increased aggressiveness and poor clinical outcome (9-11). To date, the function of ASXL1 mutations and whether these mutations could be therapeutic targets remains unclear. Mutations within ASXL1 have been reported as loss-of-function mutations that cause decreased PRC2 occupancy and dysregulation of polycomb-mediated gene silencing (12). On the other hand, other studies suggested that ASXL1 represent a gain-of-function mutations, because ectopic overexpression of truncated ASXL1 stimulates the catalytic activity of BAP1 in cells, and directly induces leukemia in animals (13, 14). Although the function of ASXL1 protein in BAP1 complex remains unclear, the catalytic activity of BAP1 is indeed involved in ASXL1 mutations induced malignancy (14). However, the development of small molecule inhibitors targeting BAP1 has been hindered due to the lack of an atomic resolution X-ray crystal structure of BAP1 or the BAP1-ASXL complex.

Here, we demonstrate that nonsense or frameshift mutations of ASXL1 encode truncated proteins with increased stability that substantially increase the association of the BAP1 complex with chromatin. Given the importance of BAP1 catalytic activity in malignant transformation, we performed an unbiased screen for small molecule inhibitors of BAP1 catalytic activity and identified a compound which we have named iBAP. Treatment of ASXL1 mutant cells with iBAP fully rescues the aberrant oncogenic patterns of gene expression. Our study has provided a molecular insight to the role of ASXL1 mutations in BAP1 stability in cancer and provided a possible targeted therapeutic approach for ASXL1 mutated leukemia by inhibition of BAP1 catalytic activity.

Results

Figure 1:
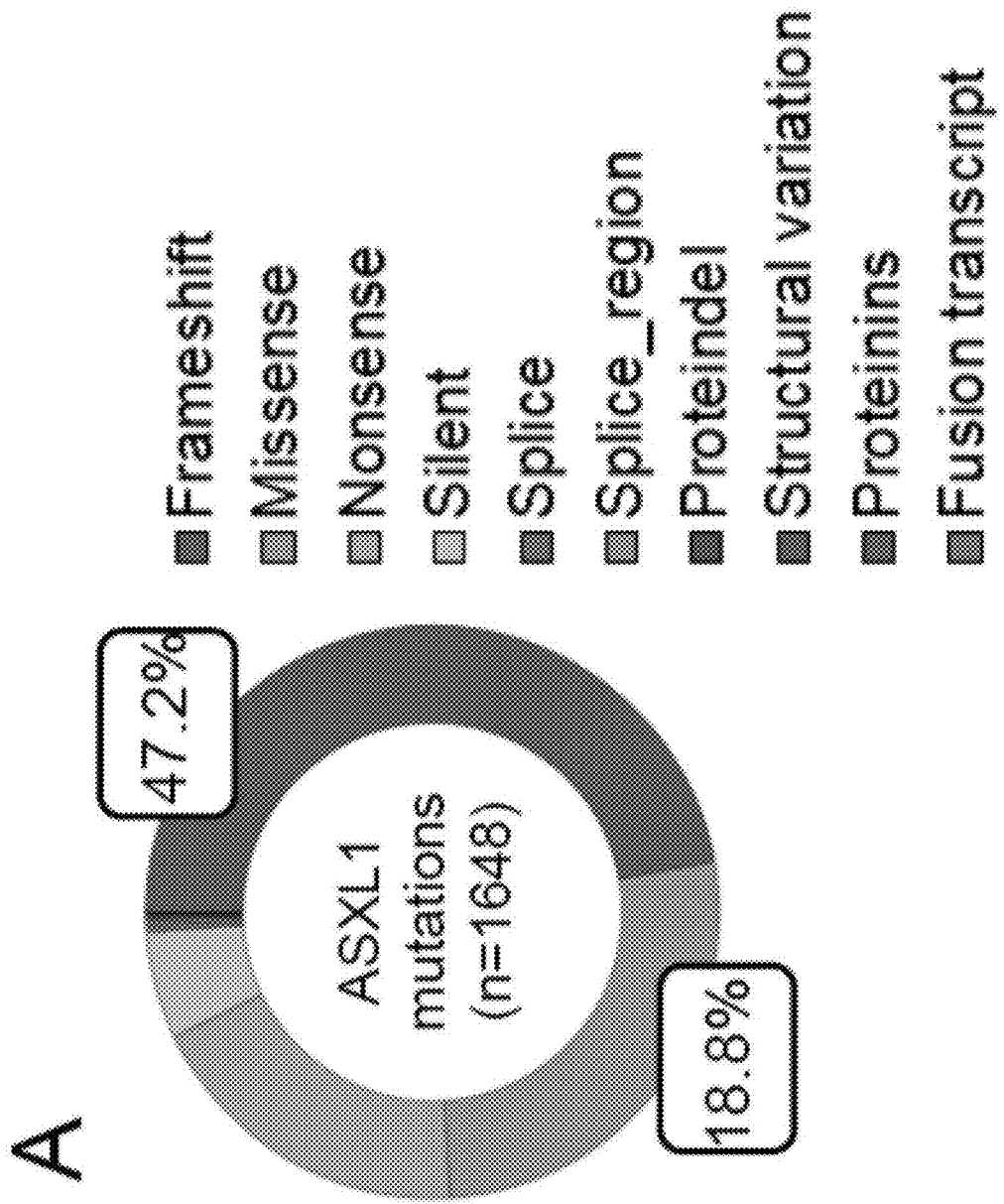
FIG. 1. A) The annotation of ASXL1 mutations in human cancers. B) The most enriched recurrent mutations within ASXL1 in human cancers. The different colors in the pie diagram indicate different cancer type. C) Schematic of the human ASXL1 gene locus and the CRISPR gRNA designed to target ASXL1 gene. D) Whole-cell lysates were used for western blot with BAP1 and ASXL1 NTD antibody for BAP1 and ASXL1 in 293T-ASXL1-WT, 293T-ASXL1-WT/Y591* and 293T-ASXL1-Y591*/Y591* cells. HSP90 was used as loading control, n=3. E) Whole-cell lysates were used for immunoprecipitation with ASXL1-NTD antibody followed by immunoblotting for BAP1 and ASXL1 in 293T-ASXL1-WT, 293T-ASXL1-WT/Y591* and 293T-ASXL1-Y591*/Y591* cells. HSP90 was used as loading control, n=3. F) An N-terminal 591 amino acid portion of human ASXL1 gene was expressed as a GFP-tagged fusion protein in HEK293T cells and subjected to GFP-purification from nuclear extracts and used for mass spectrometry analysis. Peptide numbers of each subunit of BAP1 complex purified by ASXL1-NTD were shown.
Figure 1:
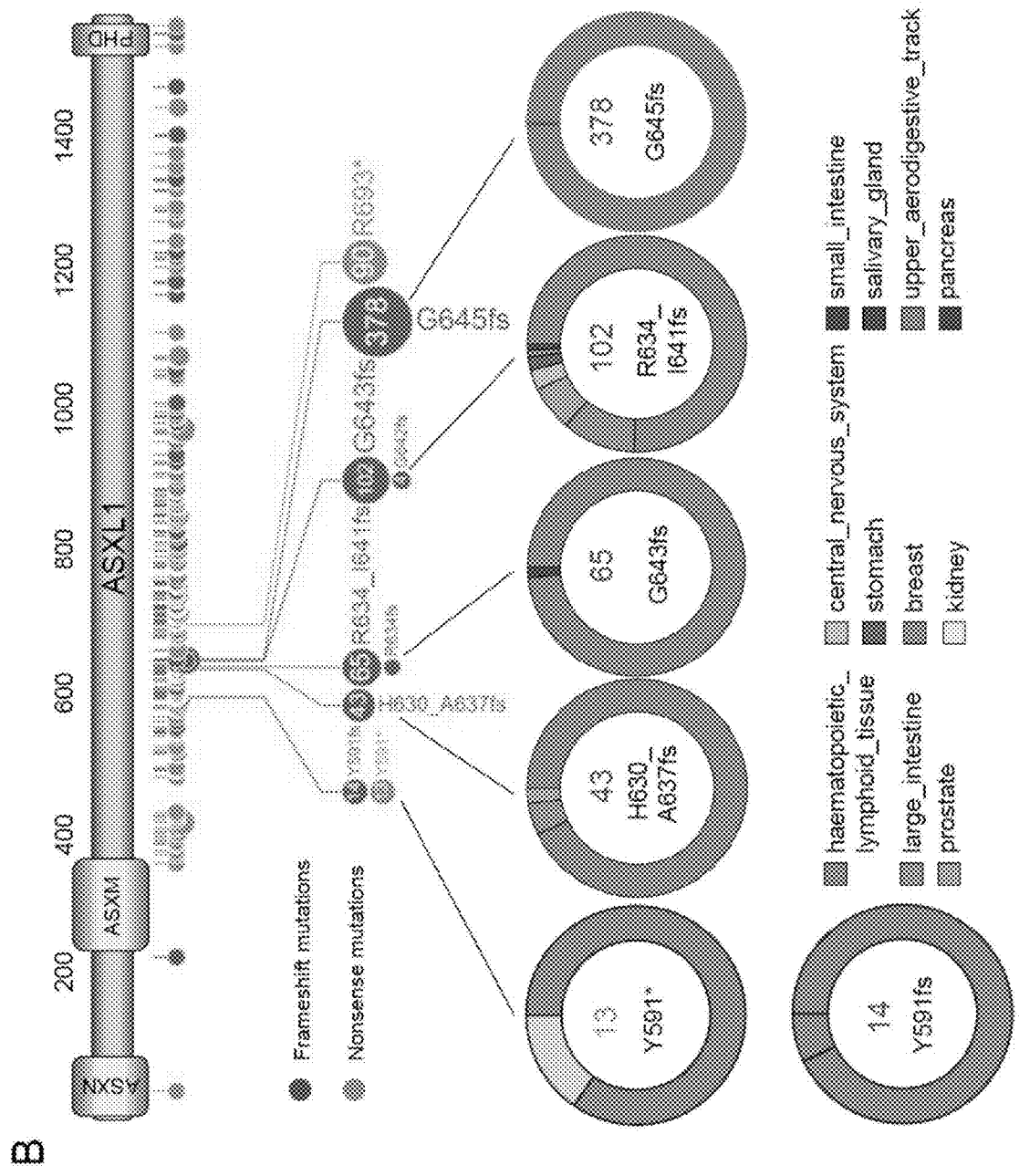
Figure 1:
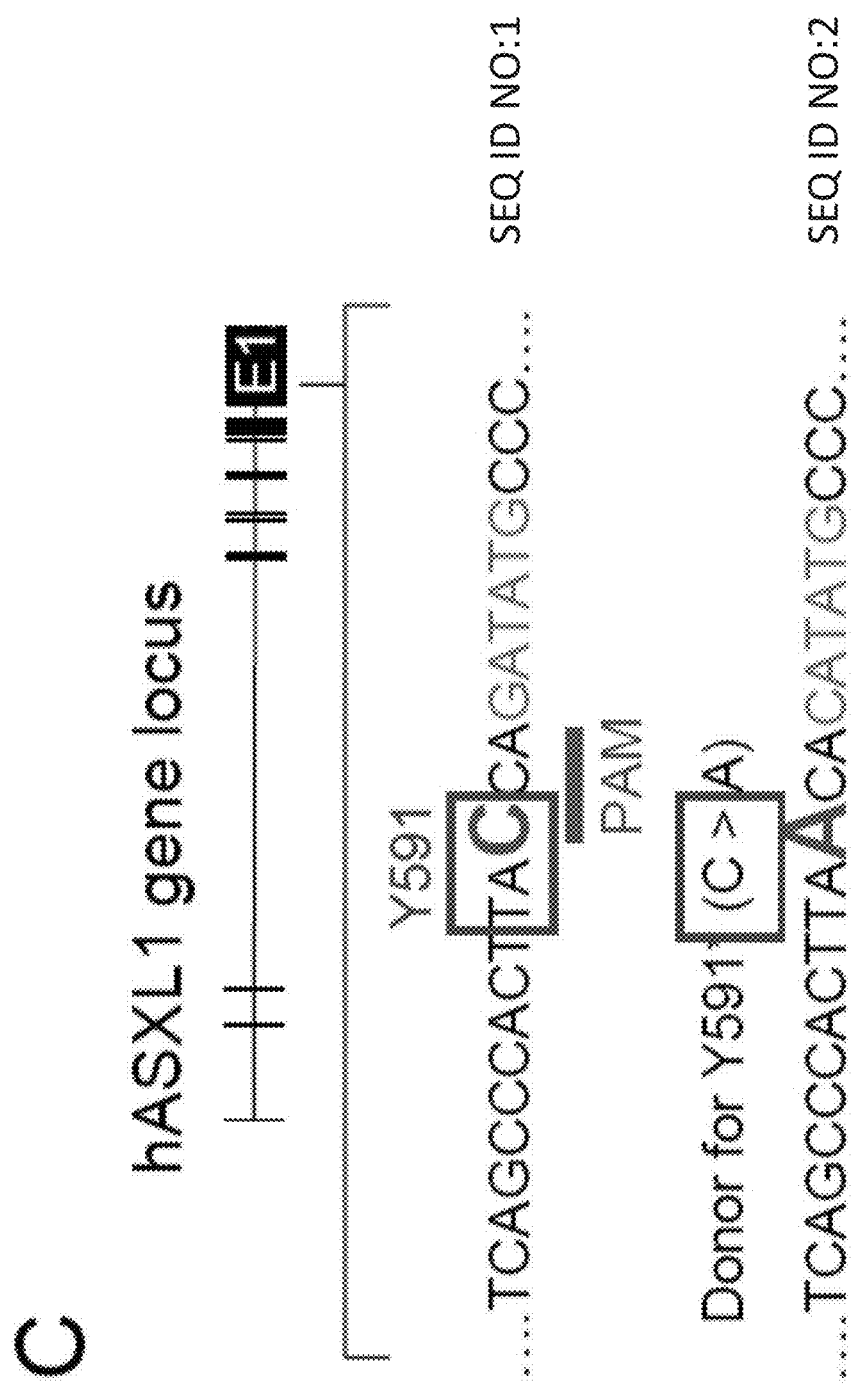
Figure 1:
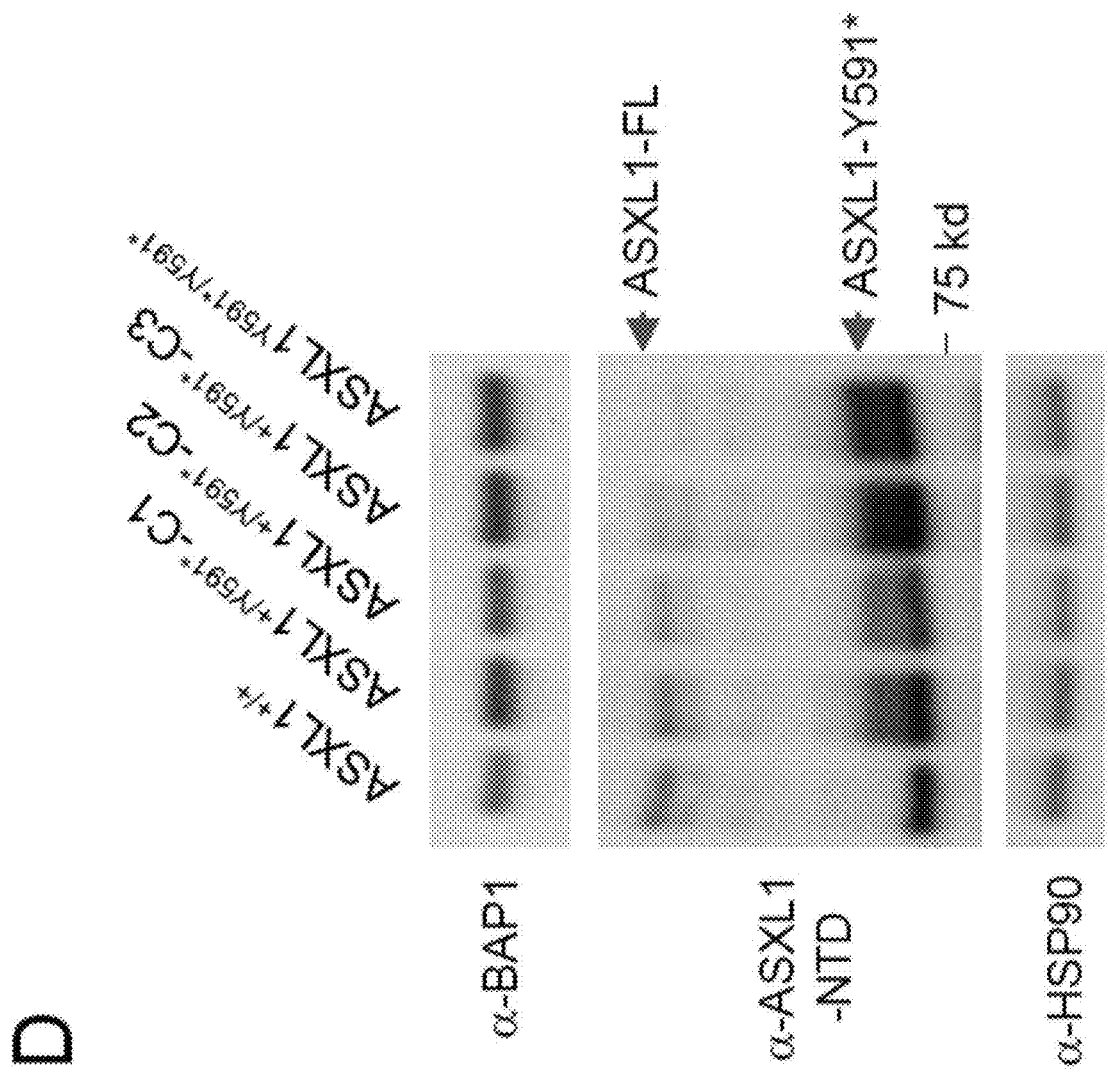
Figure 1:
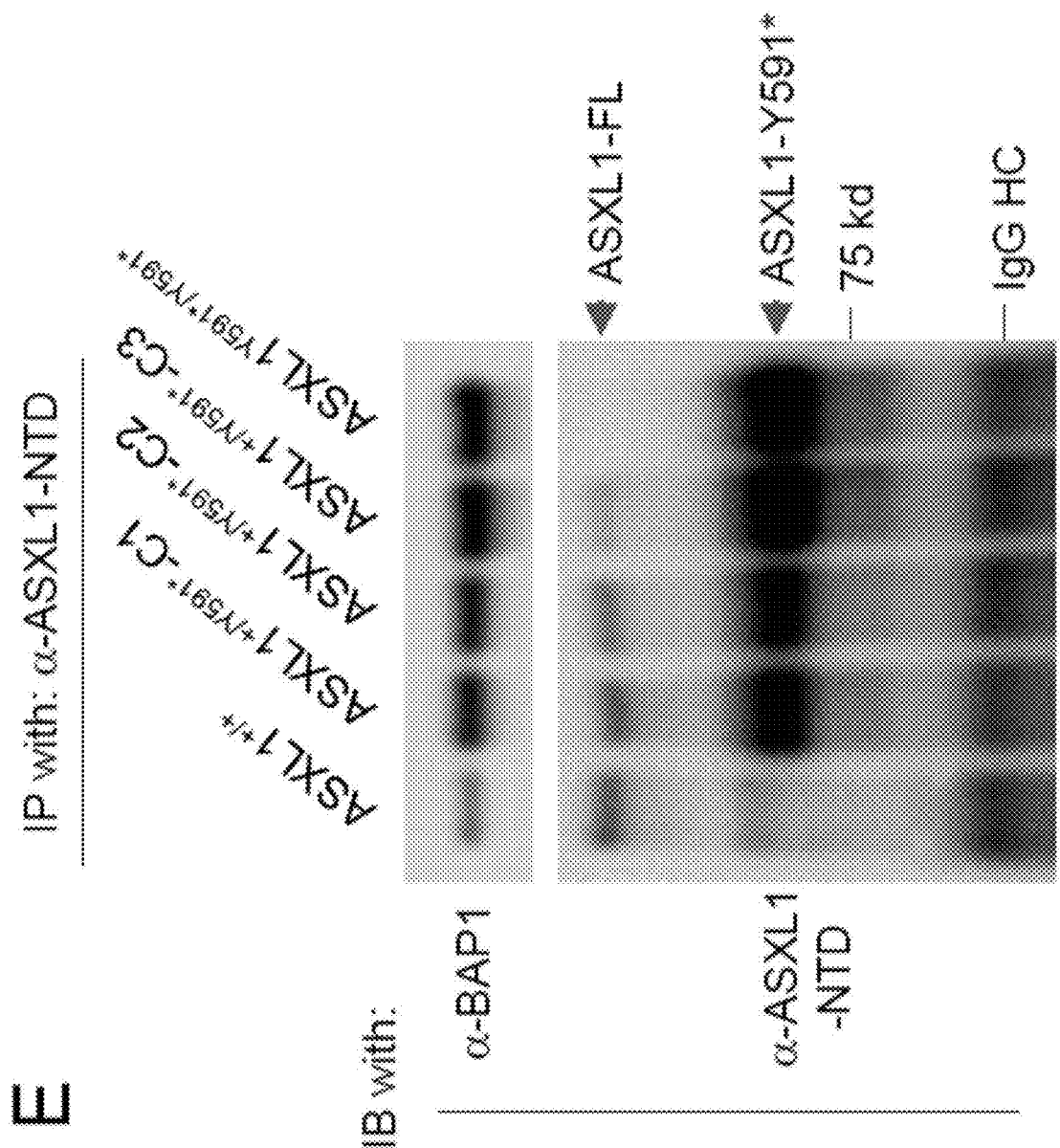

ASXL1 N-terminally truncated protein is stable. Recent studies suggest that ASXL1 mutations are a driver of human leukemogenesis. To gain further insight into ASXL1 mutations, we assigned ASXL1 mutations from all of human tumor samples (n=1648) into 10 different categories (FIG. 1A). The vast majority of ASXL1 mutations (66%) encode pre-mature stop codons: 47.2% are frameshift mutations and 18.8% are nonsense mutations (FIG. 1A) are located C-terminal to the highly conserved ASXN and ASXM domains (FIG. 1B). This unanticipated distribution of mutations suggests that the amino terminal domain of ASXL1 might retain a functional activity that is important for tumorigenesis. To test this possibility we selected two cancer associated ASXL1 truncation (Y591* and Y591fs), which are present in the well-characterized leukemia cell line K562 (FIG. 6A). To detect ASXL truncations, we generated a novel polyclonal antibody against ASXL1 N-terminus (FIG. 6B). We detected highly elevated expression of ASXL1 truncations in K562 cells as compared to 293T cells, which express wildtype ASXL1 (FIG. 6C). To further validate the specificity of our antibody, and confirm that the smaller 80 kDa band detected in K562 is ASXL1, we knocked down ASXL1 gene with two different shRNAs (FIG. 6D). ASXL1 shRNAs caused a dramatic reduction of both full length ASXL1 and the truncated product detected in K562 (FIG. 6E). These data demonstrated that ASXL1-Y591* mutated protein is not only expressed, but in fact exhibits increased stability, and may have important function in leukemia cells.

To study the function of truncated ASXL1, we introduced the c.1773>G mutation that creates ASXL1-Y591* truncation in 293T cells by CRISPR-CAS9 technology (FIG. 1C, FIG. 6F). Similar to K562 cells, the nonsense mutations express an 80 kDa truncated protein which further leads to an increase of BAP1 protein level (FIG. 1D). To determine whether the truncated N-terminal ASXL1 still interacts with BAP1 complex, we performed immunoprecipitation experiment in ASXL1-WT, ASXL1 heterozygous KI, and homozygous ASXL1 knock in cells with ASXL1-NTD antibody. We confirmed these knock-ins by western blotting and found that no full-length ASXL1 was detectable in the homozygous knock-in cells, and that expression of truncated of truncated ASXL1 correlates with increased BAP1 levels (FIG. 1E). Interestingly, we found the truncated form of ASXL1 still interacts with BAP1 protein, and BAP1 appears to be even more stable as the result of the expression of truncated ASXL1 (FIG. 1D, E). Consistent with the IP experiment, we purified N-terminus of ASXL1 (aa1-591) from HEK293T cells, and by mass spectrometry experiment, we found the N-terminal ASXL1 could also pull down BAP1 complex (FIG. 1F). We further performed immunoprecipitation experiment and confirmed that BAP1 only binds to the N-terminus of ASXL1 (FIG. 6G-I).

Figure 2:
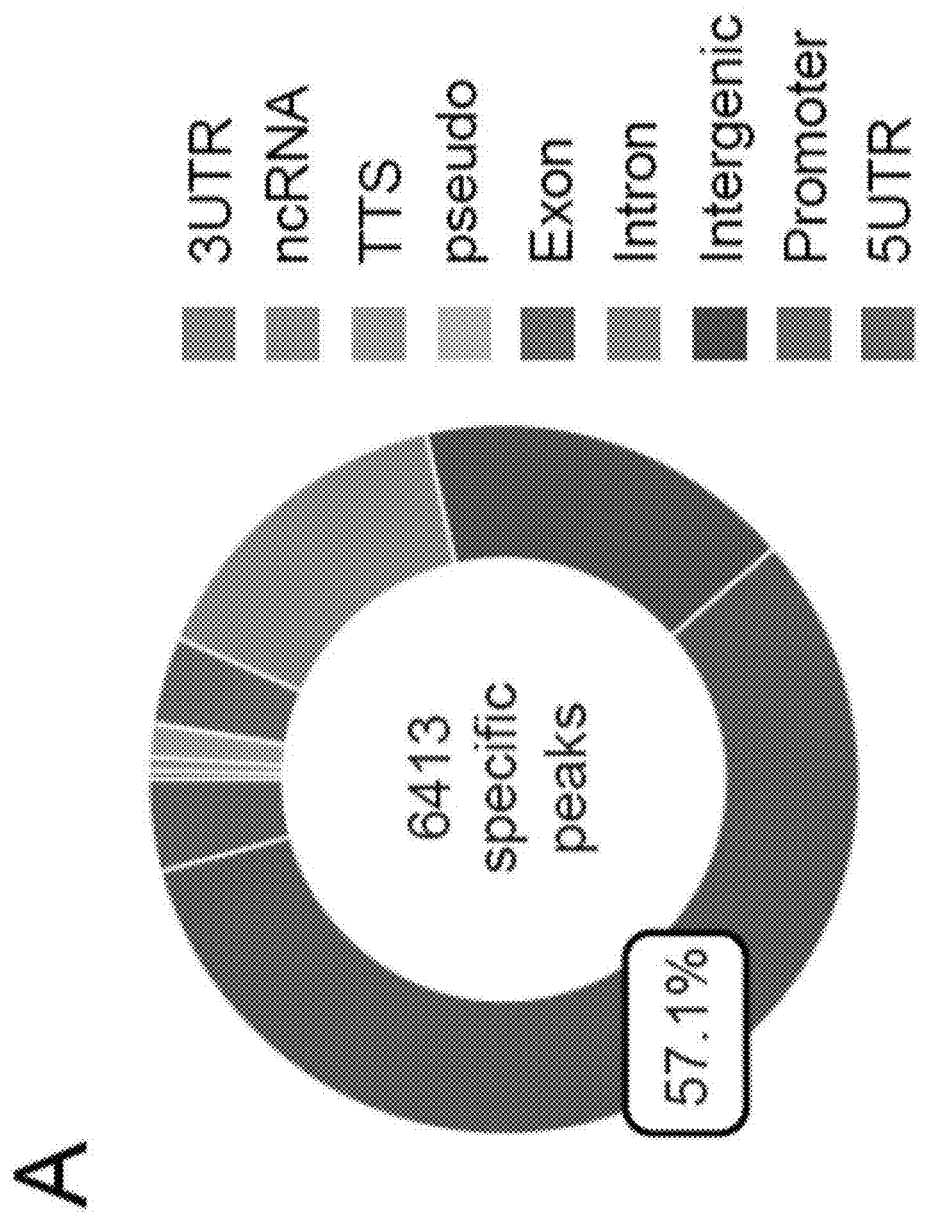
FIG. 2. A) Distribution of ASXL1 binding to gene regions in the human breast cancer cell line CAL51, as assessed by chromatin immunoprecipitation sequencing (ChIP-seq) using ASXL1 specific antibodies. Annotation summaries for ASXL1 peaks are presented in the pie chart. B) Representative tracks showing chromatin occupancy by H3K27Ac, H3K4me34 in wild type cells, and ASXL1 in ASXL1-WT and ASXL1-KO cells, n=2. C) Heat maps generated from ChIP-seq data show the occupancy of BAP1, ASXL1 and H3K4me1 as well as H3K4me3 in ASXL1 wild-type CAL51 cells. All rows are centered on BAP1 peaks, and further divided into five clusters based on K-means clustering. Cluster 1-2 peaks are enriched with enhancer marks, and Cluster 3-5 are enriched with promoter marks. (See methods for details on the clustering procedure). D) The heat map shows log2 fold changes of the occupancy levels of BAP1 and ASXL1 between ASXL1-WT and ASXL1-Y591* homozygous knock in cells. Rows are ordered as in FIG. 2c. E) The average plot shows the occupancy of BAP1 peaks between ASXL1-WT and mutant cells. Cluster 1 & 2, left panel. Cluster 3-5, right panel. F) A Venn diagram presentation of the overlap of ASXL1-WT and ASXL1-Y591* peaks. G) Pathway analysis with peaks in F). H) Representative tracks showing chromatin occupancy by ASXL1 and BAP1 in ASXL1-WT and -mutant cells, n=2.
Figure 2:
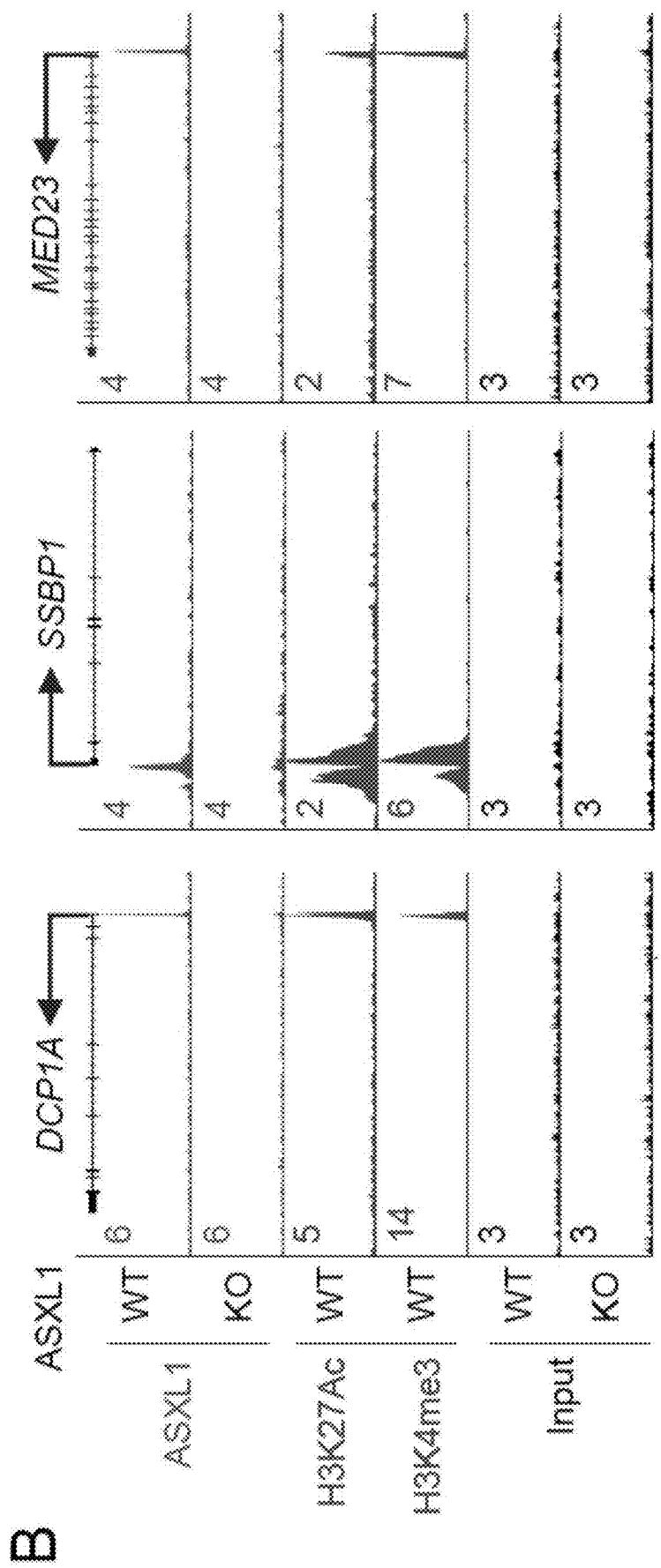
Figure 2:
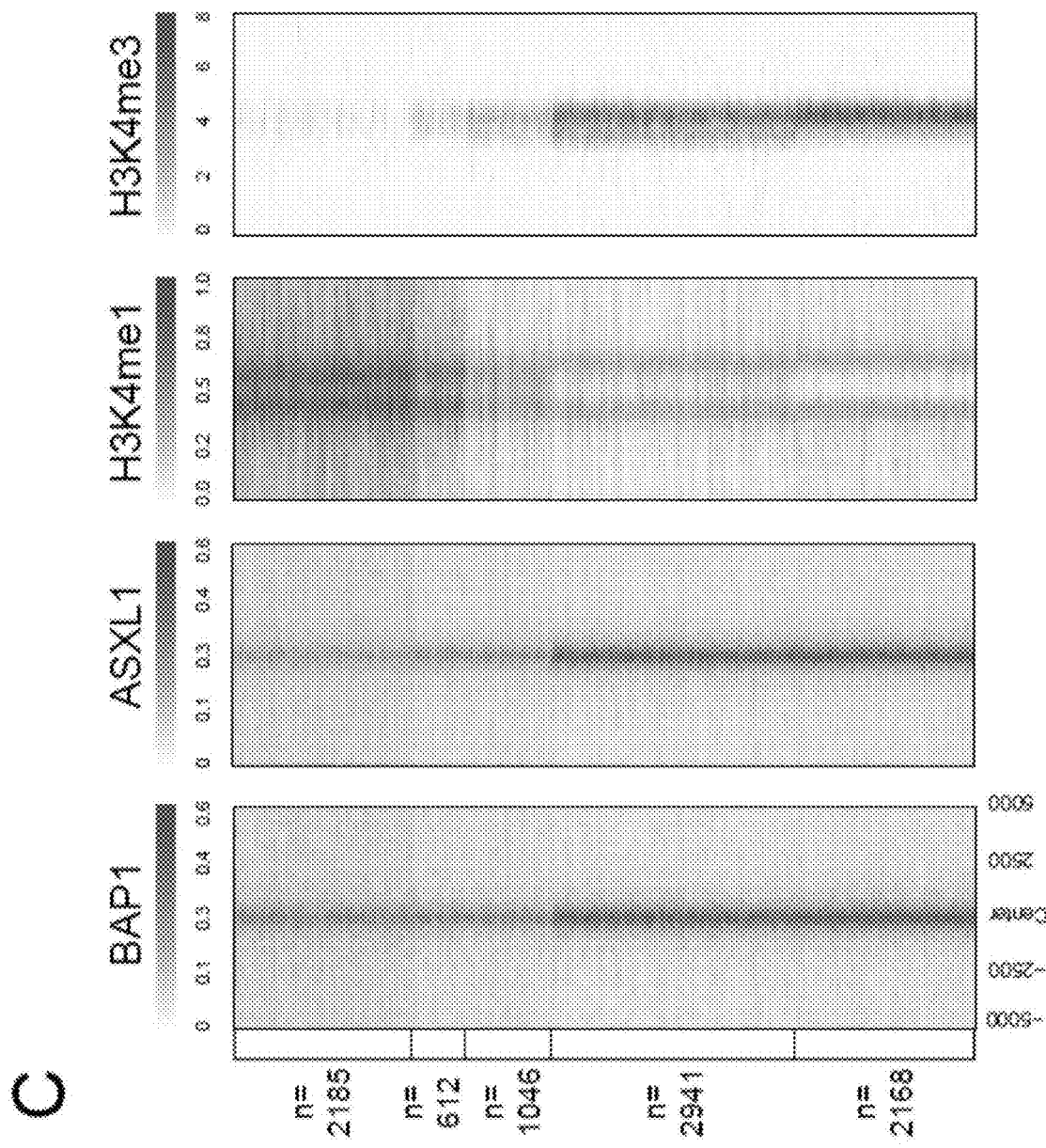
Figure 2:
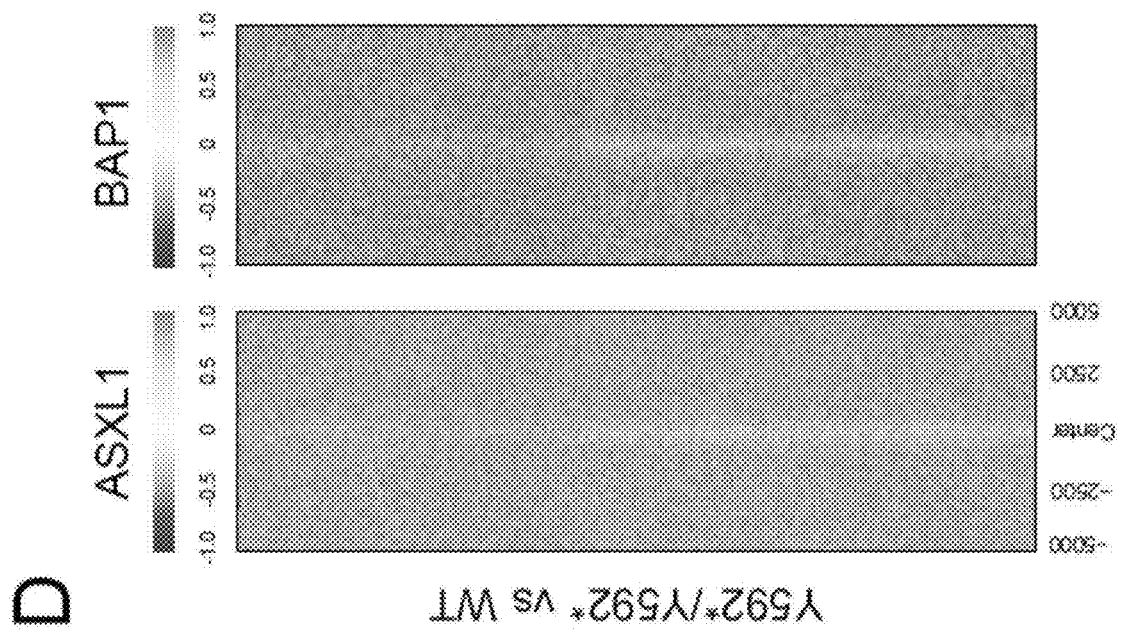
Figure 2:
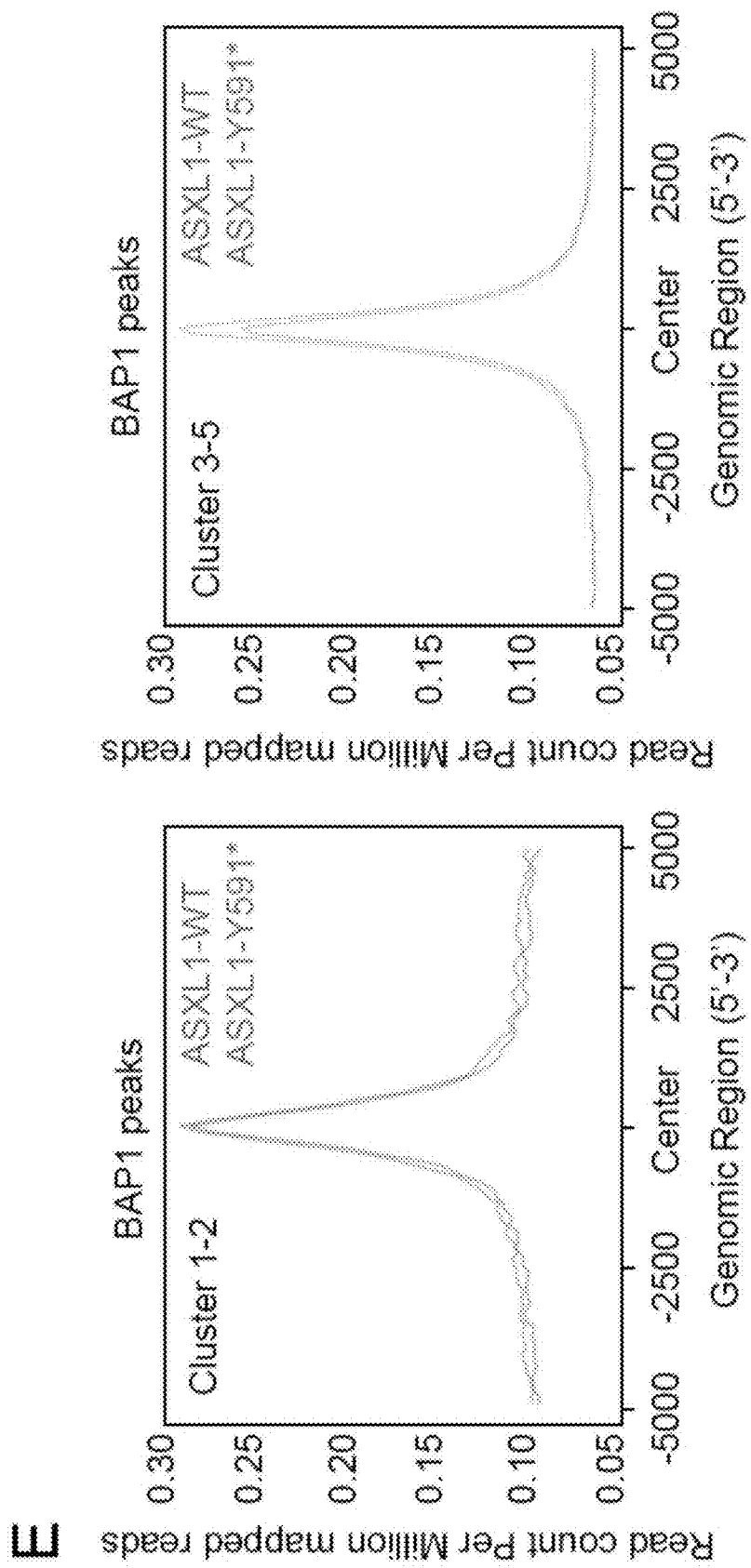
Figure 2:
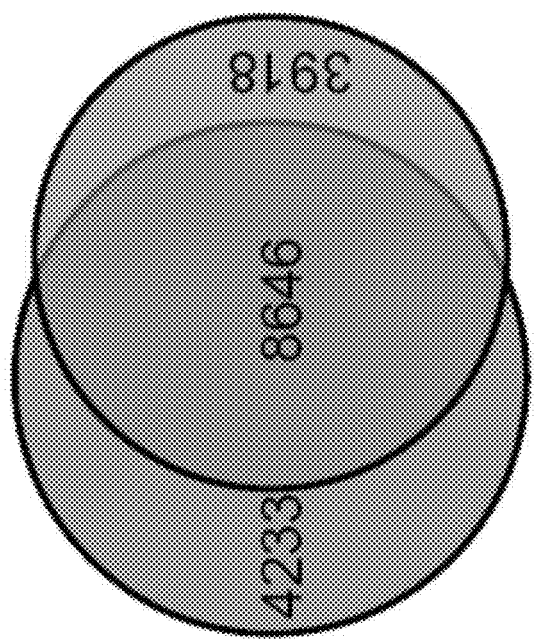
Figure 2:
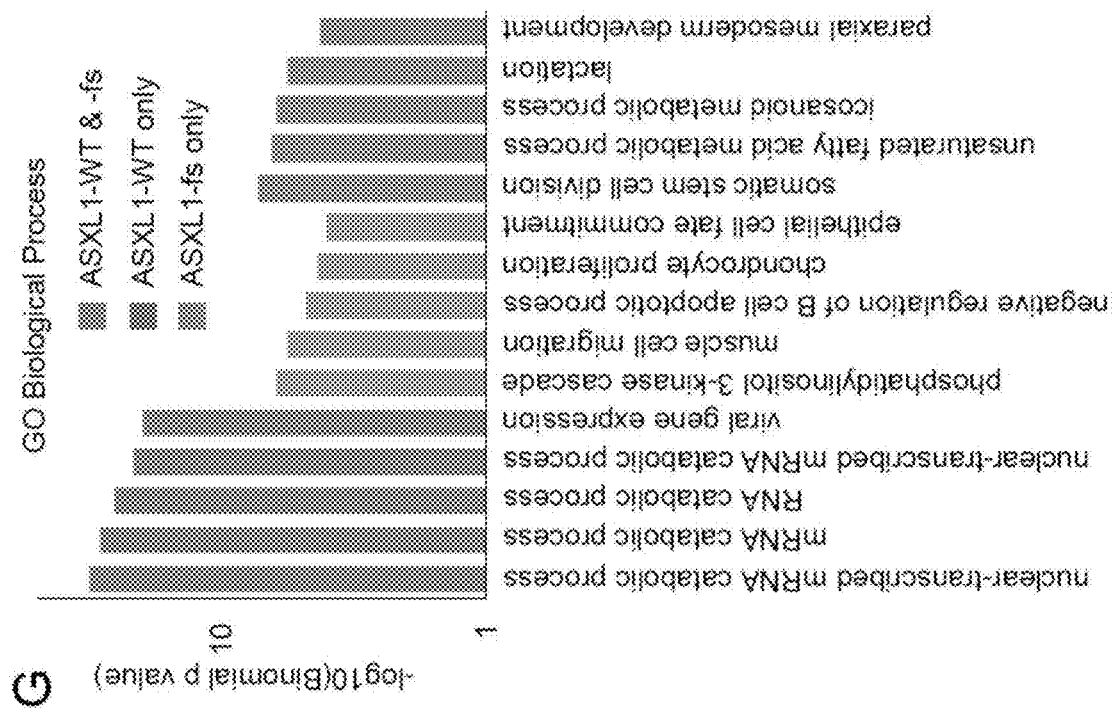
Figure 2:
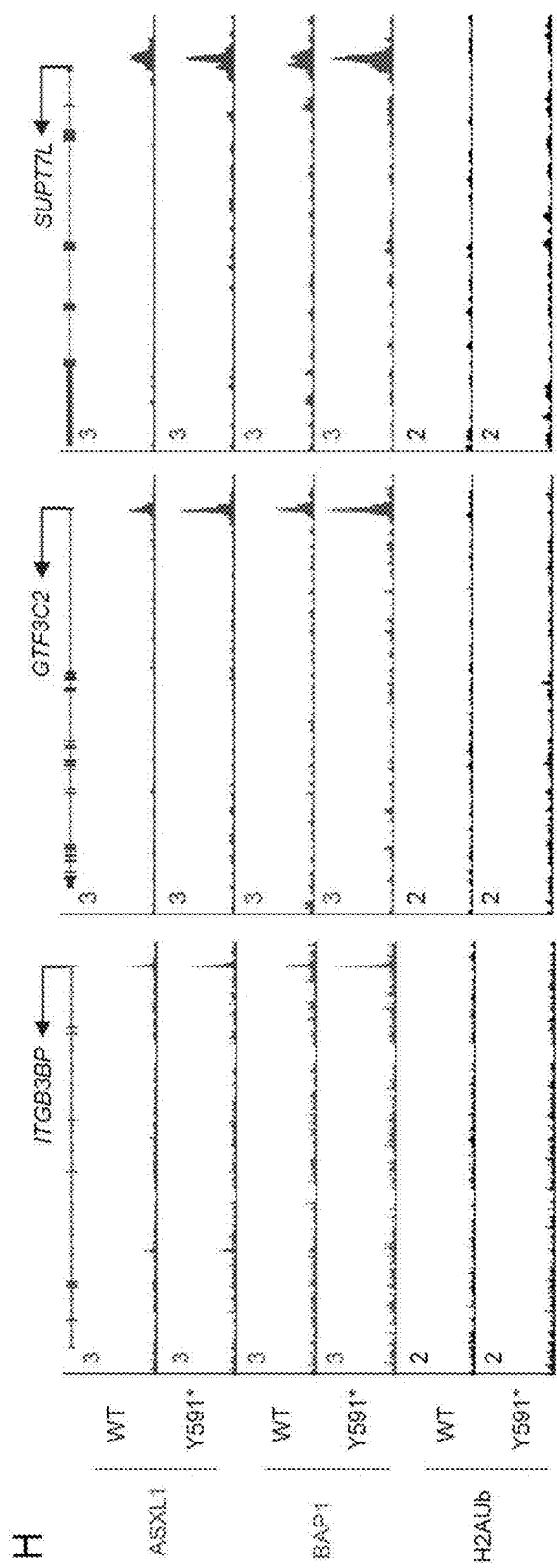

BAP1 complex functions as a general transcriptional activator (15), therefore, to determine whether ASXL1 mutations contribute to transcription regulation, we performed RNA-seq to measure gene expression changes in ASXL1-WT and ASXL1-Y591* cells. Heterozygous and homozygous knock-in cells exhibit similar gene expression patterns (FIG. 2A). We found 543 genes are significantly up-regulated (p<0.01, fold-change >2) in both heterozygous and homozygous knock in cells (FIG. 2B). A mere 15 genes are down-regulated in both of the genetic backgrounds. This result suggests that similar to BAP1 function, ASXL1 mutations also function to activate transcription. Additionally, we found the genes in Kras pathway and EMT pathway are mostly enriched in the both heterozygous and homozygous mutant cells (data not shown).

Genome-wide binding pattern of truncated ASXL1. To further explore the mechanism of how truncated ASXL1 activates gene expression, we knocked out ASXL1 in CAL51 cells by CRISPR Cas9 gene editing. The promoter region and the first exon was chosen as the target for CRISPR (FIG. 8A). By RNA-seq, we confirmed that there is no detectable ASXL1 mRNA in all three different KO clones (FIG. 8B). We then performed ASXL1 ChIP-seq in the WT and KO cells to determine the genome-wide binding pattern of wild-type ASXL1 with our homemade ASXL1 N-terminal specific antibody (FIG. 8C). We detected 6413 specific peaks in ASXL1 wild type cells (FIG. 2A) and annotation analysis that the vast majority of ASXL1 binding sites (57.1%) localized to the promoter regions (FIG. 2A, B). To determine whether loss of ASXL1 affects histone H3K27me3 level, we performed H3K27me3 ChIP-seq in ASXL1-WT and —KO cells, with EZH2 inhibitor GSK126 as positive control. ASXL1 loss does not globally affect H3K27me3 levels, indicated that the ASXL1/PRC2 contact may be cell type specific (FIG. 8D, E, and data not shown). To determine whether ASXL1 mutations affect its chromatin binding or BAP1 complex function, we centered all of the ASXL1 peaks at the BAP1 peaks in CALM cells, and further divided the peaks into five clusters, as previously described (2). This ChIP-seq analysis revealed a striking co-occupancy of ASXL1 and BAP1 at both promoters and enhancers (FIG. 2C). Interestingly, we found mutations in ASXL1 leads to a significant enrichment of BAP1 at promoters but not at enhancers (FIG. 2D, E, FIG. 8F) in CALM cells. In cells expressing mutated ASXL1 (Y591*), we observed 4233 gained peaks comparing with the full-length ASXL1 (FIG. 2F, G). These binding sites were strongly associated with genes encoding regulators of metabolism and developmental (FIG. 2G).

Figure 3:
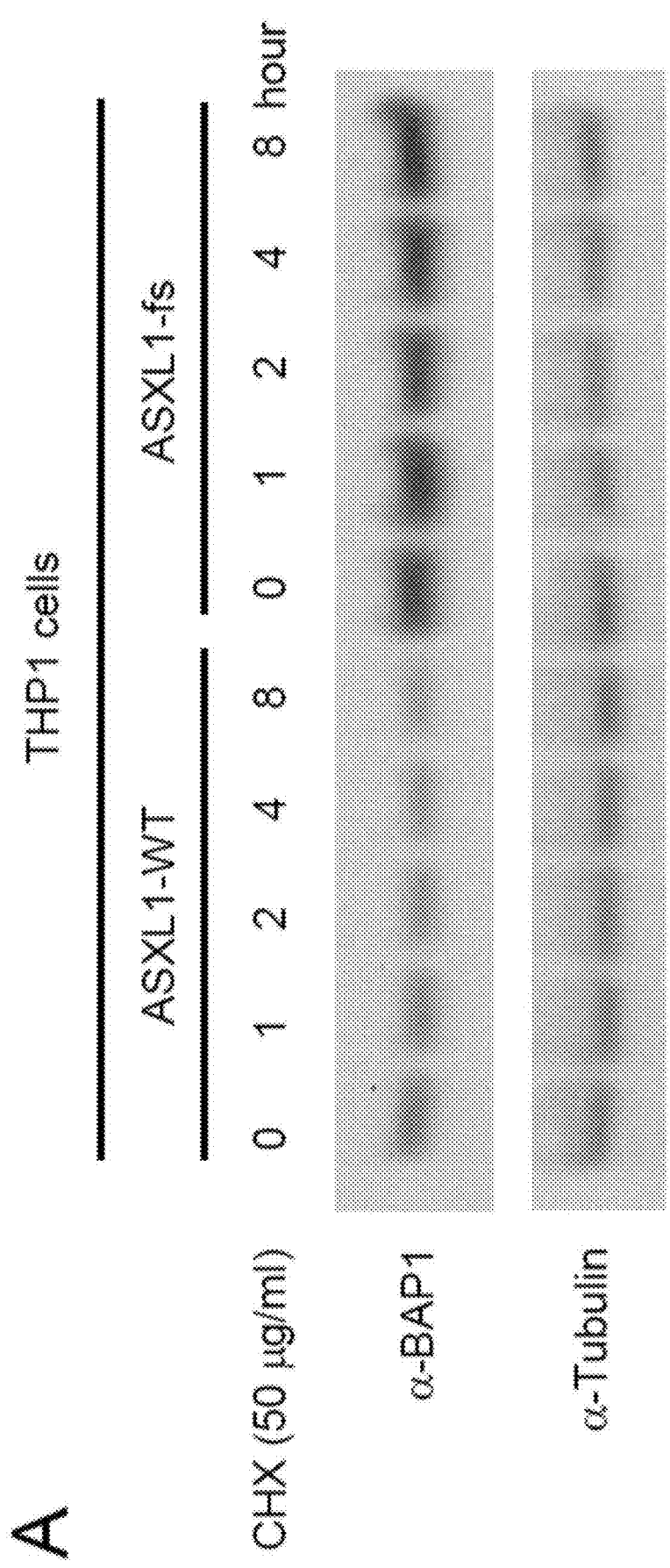
FIG. 3. GOF ASXL1 mutants stabilizes BAP1 and increases BAP1 recruitment in leukemia. The THP1-ASXL1-WT and -fs cells were treated with 50 μg/ml CHX for different time. The BAP1 protein was determined by western blot (A) and further quantified by imageJ (B). C) Heat maps generated from ChIP-seq data showing the occupancy of BAP1, ASXL1 and H2AK119Ub in ASXL1-
Figure 3:
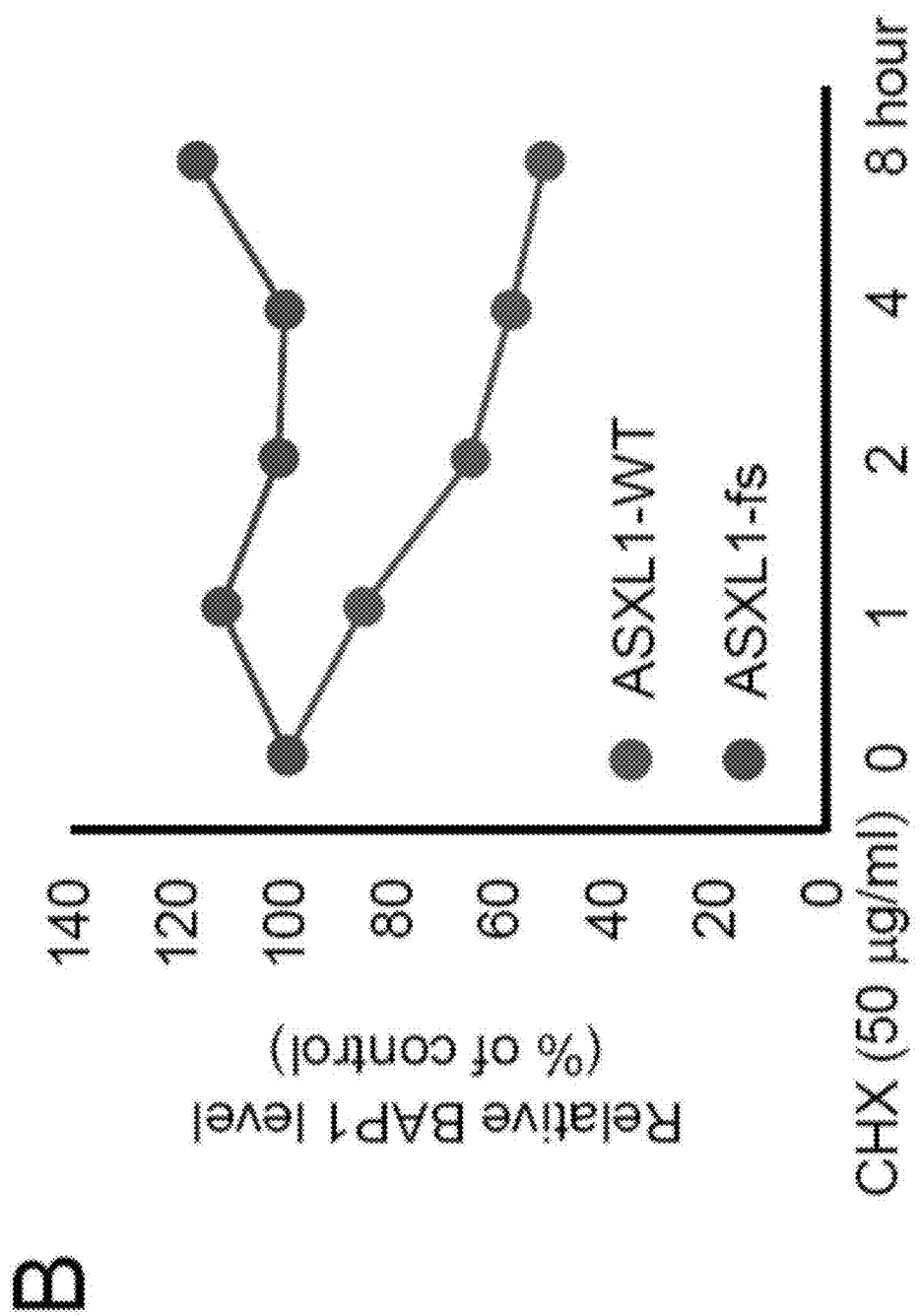
Figure 3:
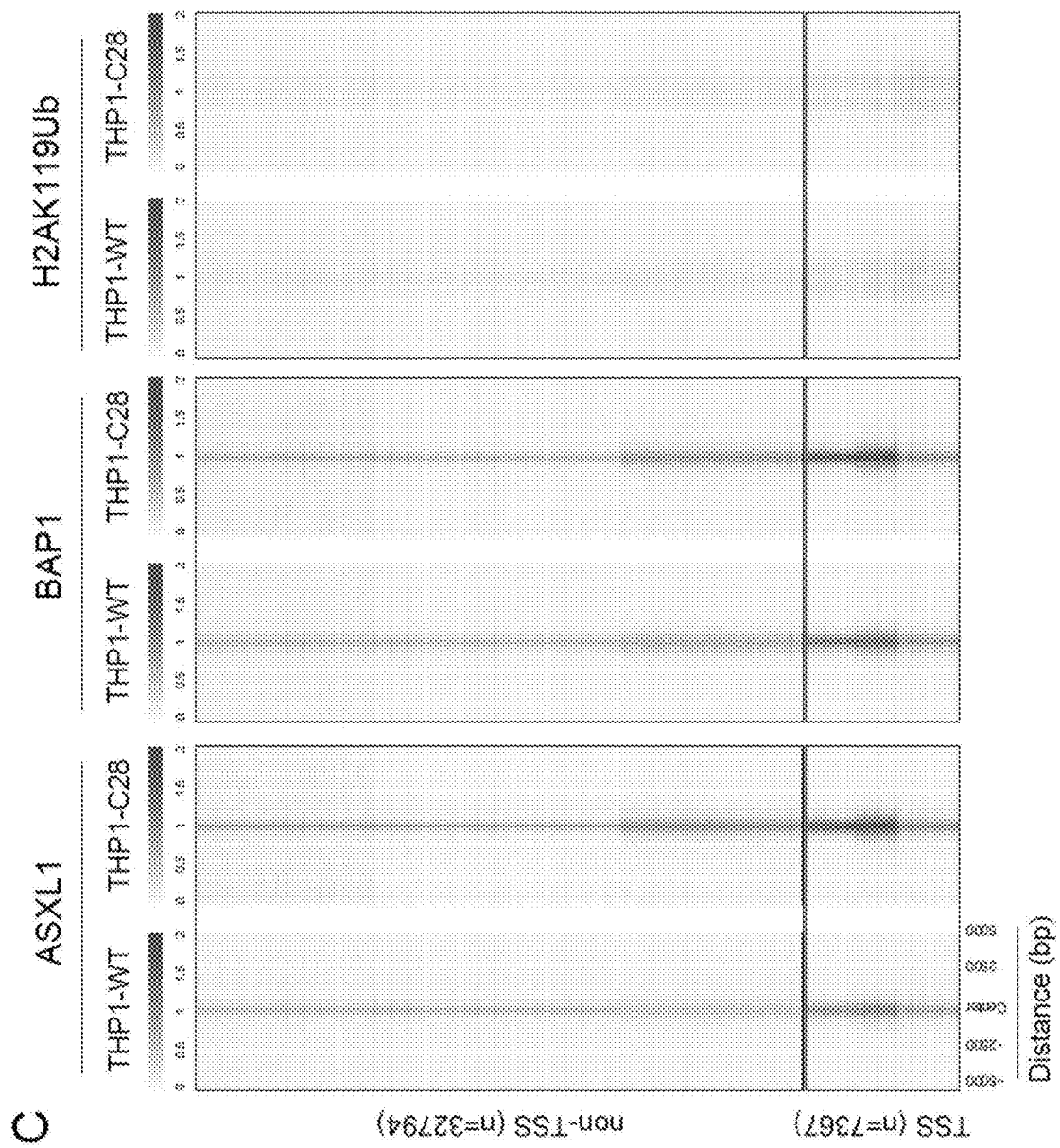
Figure 3:
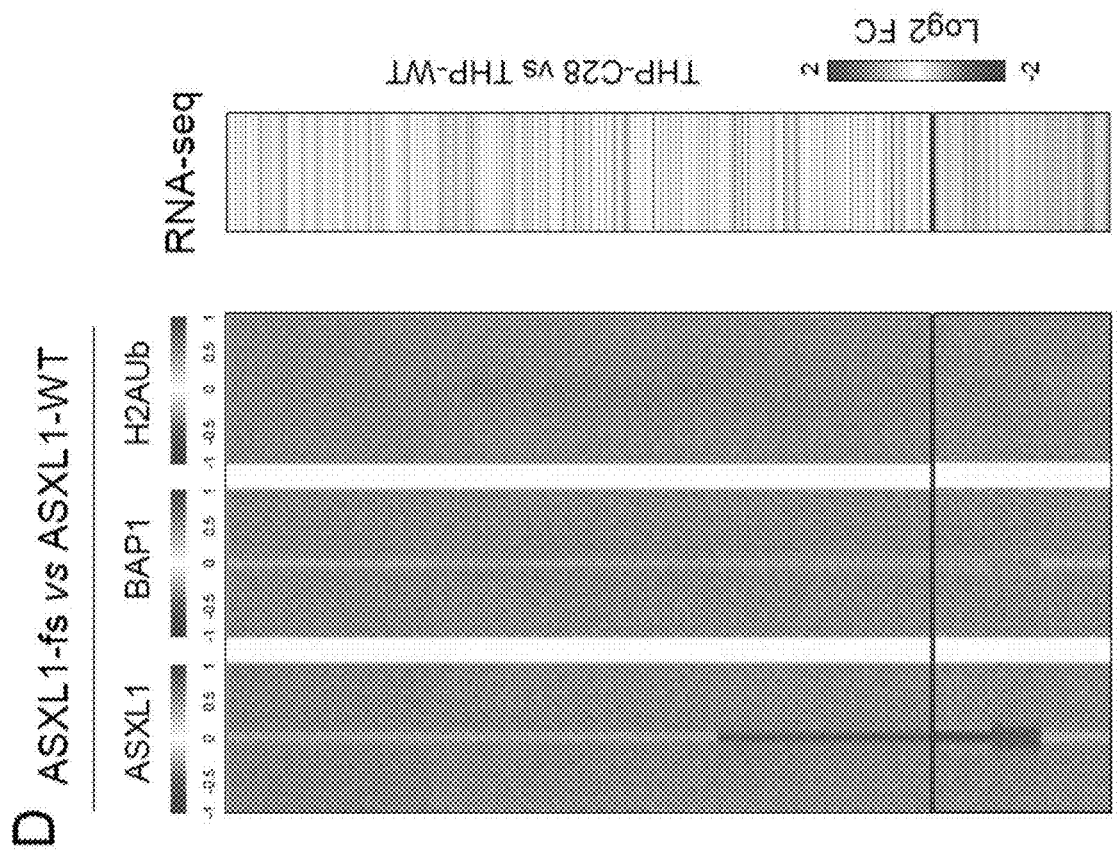
Figure 3:
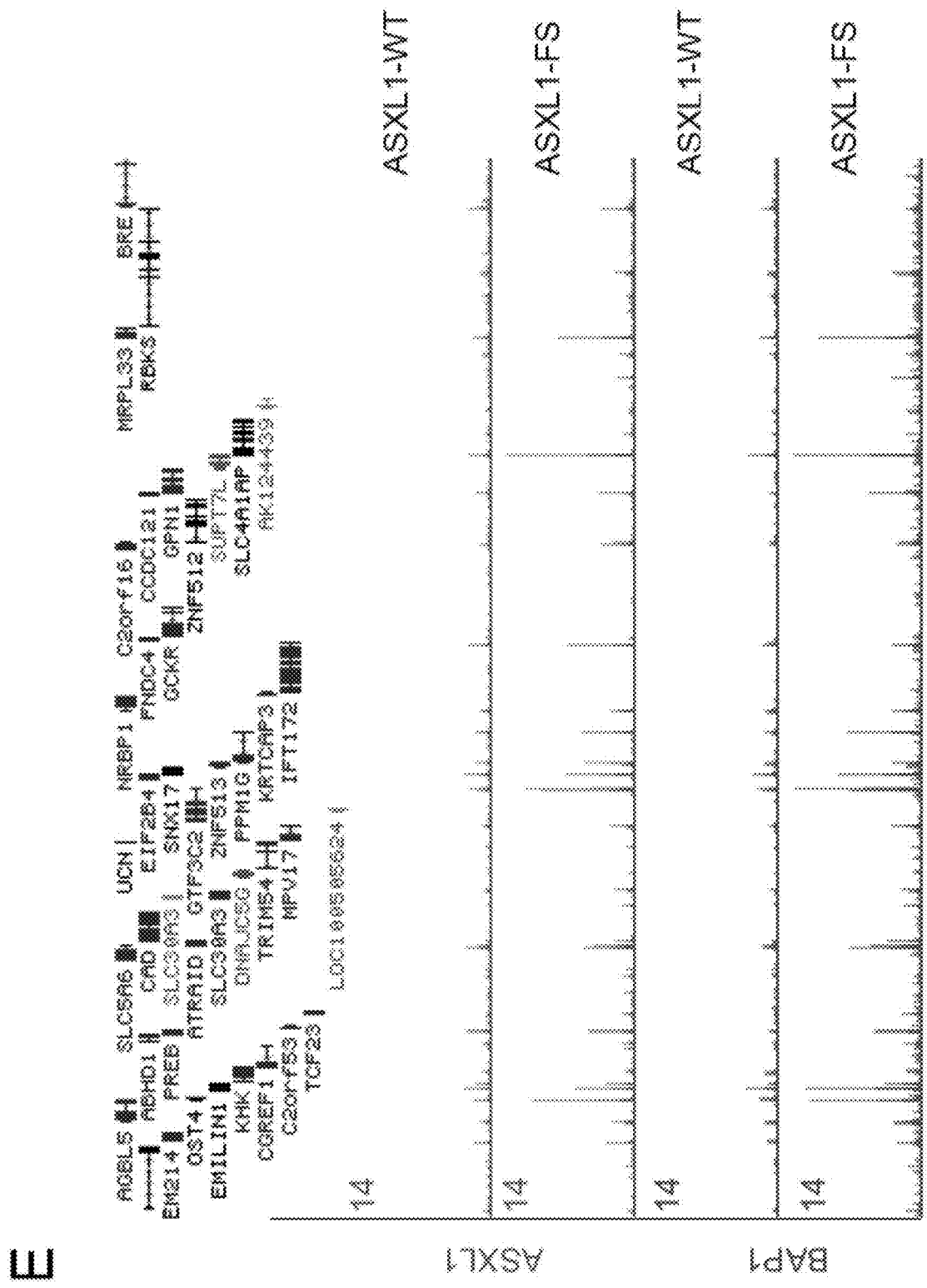
Figure 3:
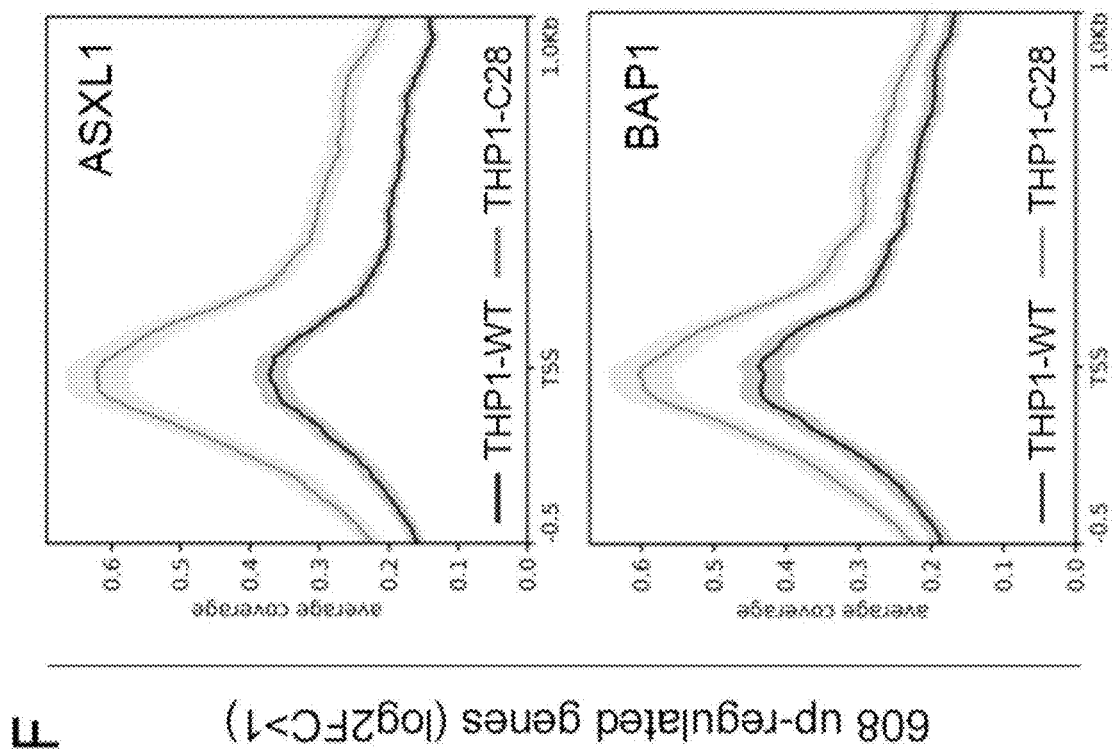

ASXL1 GOF mutants stabilize BAP1 and increases BAP1 recruitment to chromatin in leukemia. Because ASXL1 mutations are mostly frequently detected in hematological malignancies, we sought to investigate whether ASXL1 mutations may gain of oncogenic function in leukemia. Because frameshift mutations are the most common mutations in leukemia, we introduced reading frameshift (FS) mutations by CRISPR-CAS9 in the THP1 cell line, which express wild-type ASXL1 gene (FIG. 9A). As shown in Supplementary FIG. 4B, we found that the mutations also lead to the shorter but more stable product of ASXL1 protein in THP1 cells. Furthermore, the mutant ASXL1 also interacts and stabilizes BAP1 protein in these cells (FIG. 9C, FIG. 3A, B). We then performed ASXL1 and BAP1 ChIP-seq to determine the chromatin binding of both factors in ASXL1-WT and -FS THP1 cells. ASXL1 occupies both promoter region as well as active enhancer regions (FIG. 9D), which further increases the BAP1 binding at those regions (FIG. 3C-E). RNA-seq analysis shows that the enriched ASXL1 and BAP1 complex at chromatin can activate the expression of genes nearby (FIG. 3D). Comparing with ASXL1-WT cells, there are 608 genes significantly up-regulated ($p<0.01$, fold change $>2$) in ASXL1-FS cells, (FIG. 3F, FIG. 9E), and the average plot indicated that both BAP1 and the truncated ASXL1 are all enriched at the promoter region of those genes.

iBAP selectively inhibits cells with ASXL1 GOF mutations. Since the truncated ASXL1 functions as co-activator of BAP1 in human leukemic cells, and based on previous studies, mutations in ASXL1 lead to the hyper-activation of BAP1 in mice (16), we sought to identify small molecule inhibitors that inhibit BAP1 catalytic activity. Although crucial catalytic residues in BAP1 have been identified through general homology with other deubiquitinases, a detailed atomic resolution structure of BAP1 has yet to be determined. Therefore, because a structure-based approach is currently unattainable, we adopted a structure-agnostic unbiased biochemical screen for small molecule inhibitors of BAP1's deubiquitinase activity. Toward this goal, we employed an Ubiquitin- 7-amino-4-methylcoumarin (Ub-AMC) screening platform. Ubiquitin-AMC (Ub-AMC) is a fluorogenic substrate for ubiquitin hydrolases based on the C-terminus derivatization of ubiquitin with 7-amido-4-methylcoumarin (AMC). Upon incubation with a protease recognizing Ubiquitin, such as BAP1, AMC is released and the increase in fluorescence can be measured (7, 17) (FIG. 4A). We optimized the screening condition and finally used 100 nM Ub-AMC and 0.1 nM recombinant BAP1 (FIG. 10A) for the reaction (FIG. 10B). The top 1% hits from 3,000 of 8-compound mixtures were subjected for a secondary validation (FIG. 10C, D). The final two hits, 7A20 and 8B21 were selected and the 8 compounds from each of the hit were further validated one by one (FIG. 10E). One out of eight compounds in each mixture (#7152836 and #7231120) could efficiently inhibit BAP1 catalytic activity in vitro (Figure SE and F). Because Compound #7152836 exhibited the best inhibition activity (FIG. 10G), we tested all commercially available analogs of this compound by Ub-AMC assay (FIG. 11A, B). This led us to identify Analog 8 as the most efficient inhibitor of BAP1 of all compounds tested (FIG. 4B). We name this small molecule as iBAP and further tested the drug effect in vitro. Compared with ASXL1-WT cells such as THP1 and MOLM13 cells, we found the K562 cells (ASXL1-Y591*) are significantly more sensitive to iBAP treatment in vitro (FIG. 4C). To further test the drug specificity, we treated THP1-ASXL1-WT, THP1-ASXL1-fs (Clone 1 and 2) cells with iBAP and found that cells with ASXL1 frameshift mutations are ten times more sensitive to iBAP treatment (FIG. 4D, E). To determine whether iBAP treatment affects gene expression, we performed RNA-seq with THP1-ASXL1-WT and THP1-ASXL1-fs cells treated with either DMSO or iBAP (10 uM). iBAP treatment globally down-regulates the expression of these genes that are up-regulated in ASXL1-fs cells (FIG. 4F). The venn-diagram in FIG. 4G shows 246 genes significantly up-regulated in ASXL1-fs cells can be rescued by iBAP treatment. Numerous leukemia associated genes such as HMGNS, STATSA, HOXA11, BCAR1, TWIST1 and MBD2 are direct transcriptional targets of mutated ASXL1, and they are fully rescued by iBAP treatment (FIG. 4H). Consistent with the drug effect in leukemia cells, we found 293T cells harboring ASXL1 point mutations, which are resistant to chemo-agents treatment, are also sensitive to iBAP treatment compared to wild-type cells (FIG. 11C).

iBAP delays the progression of ASXL1-mutant leukemia and improves animal survival. To further test the effect of BAP1 inhibition by small molecule on leukemic progression in vivo, we studied the efficacy of iBAP in K562 (ASXL1-WT/Y591*) xenograft model. First, we tested the drug toxicity at 10, 25, 50 and 100 mg/kg in mice, and we found only the highest dosage reduced the body weight of 2 out of 3 mice (FIG. 12). Based on this result, we decided to treat the animal with 50 mg/kg iBAP in the next experiment. We labeled K562 cells with luciferase, and transplant these cells in NSGS mice through tail-vein injection. Two weeks after transplantation, we started to treat the animals with either PBS or iBAP (50 mg/kg) (FIG. 5A). We found BAP1 inhibition by iBAP significantly delayed the progression of the disease (FIG. 6C).

Discussion

Mutations in the BAP1 deubiquitinase cause a human cancer predisposition syndrome with a high incidence of uveal melanoma, mesothelioma, and renal cell carcinoma (18-21). In mice, it has been shown that loss of BAP1 induces myeloid transformation, indicating that BAP1 may function as a tumor suppressor in vivo (7). In our recent studies, we have shown that BAP1 mediates the recruitment of MLL3/COMPASS tumor suppressive complex to enhancer chromatin, and loss of BAP1 or mutations within MLL3 PHD fingers that affect MLL3/BAP1 interaction leads to the dysregulation of gene expression due to the imbalance of COMPASS and Polycomb (2). However, in other studies, BAP1 was also found to be critical for cancer cell survival. For instance, depletion of BAP1 in human breast cancer cells strongly suppressed lung metastasis (22). These seemingly contradictory results can be reconciled by recent work from the Dixit lab showing that BAP1 can function as an oncogene or tumor-supressor in a tissue dependent manner (23). The precise basis of these tissue dependent functions of BAP1 is currently unclear but may involve interactions with the PRC1/Ring1 complex and represents an important area for future research. In animals, reducing the catalytic activity of BAP1 could also prevent ASXL1 truncation-driven myeloid malignancy (16). These data suggested that BAP1 may have content dependent function, and targeting BAP1 may serve as a novel therapeutic strategy especially when BAP1 is hyper-activated.

We demonstrate conclusively that truncations of BAP1 encoding the amino terminal fragment spanning the ASXN and ASXM domains are expressed at higher levels than full length ASXL1 and have a gain-of-function activity that stabilizes BAP1. Moreover, truncated ASXL1 still participates in the BAP1 complex and may exhibit increased affinity, although future biophysical and structural studies are needed to fully elucidate these differences. Previous studies demonstrate that ASXL1 directly binds to the C-terminus of BAP1 protein (24, 25), where the E3 ligase UBE2O directly binds to and induces BAP1 protein degradation (26). We think those ASXL1 truncations may compete with endogenous UBE2O and further stabilizes BAP1 in cells.

The BAP1 catalytic activity has been demonstrated to be essential for mutated ASXL1 induced leukemia in vivo, suggesting that targeting BAP1 activity will be useful for understanding the role of mutated ASXL1 in transcription regulation and as therapeutic tools for the treatment of leukemia. Because there is no crystal structure of BAP1 complex, we have decided to perform the small molecule screening with recombinant BAP1 protein and Ub-AMC as a substrate, which has been used in previous studies (7, 17). As close family members, both of BAP1 and UCHL5 have unique extended C-terminal tails, and are able to hydrolyze small and large ubiquitin adducts (27). However, we did not observe any significant difference of the cell viability between ASXL1 wild type and mutant cells by UCHL5 inhibitor treatment (28). This result also indicated the specificity of iBAP against BAP1 enzymatic activity. Taken together, our work has demonstrated the existence of ASXL1 truncations in human leukemia, uncovered the mechanism that how truncated ASXL1 functions in leukemia, and also provided the core structure of BAP1 inhibitor which could also function as a lead for future optimization.

REFERENCES

1. M. S. Lawrence et al., Mutational heterogeneity in cancer and the search for new cancer-associated genes. Nature 499, 214-218 (2013).
2. L. Wang et al., Resetting the epigenetic balance of Polycomb and COMPASS function at enhancers for cancer therapy. Nat Med 24, 758-+(2018).
3. L. Wang, A. Shilatifard, UTX Mutations in Human Cancer. Cancer Cell 35, 168-176 (2019).
4. K. D. Rasmussen, K. Helin, Role of TET enzymes in DNA methylation, development, and cancer. Gene Dev 30, 733-750 (2016).
5. J. Y. Zhang et al., Disruption of KMT2D perturbs germinal center B cell development and promotes lymphomagenesis. Nat Med 21, 1190-+(2015).
6. A. Ortega-Molina et al., The histone lysine methyltransferase KMT2D sustains a gene expression program that represses B cell lymphoma development. Nat Med 21, 1199-+(2015).
7. A. Dey et al., Loss of the Tumor Suppressor BAP1 Causes Myeloid Transformation. Science 337, 1541-1546 (2012).
8. S. Misaghi et al., Association of C-Terminal Ubiquitin Hydrolase BRCA1-Associated Protein 1 with Cell Cycle Regulator Host Cell Factor 1. Mol Cell Biol 29, 2181-2192 (2009).
9. V. Gelsi-Boyer et al., Mutations of polycomb-associated gene ASXL1 in myelodysplastic syndromes and chronic myelomonocytic leukaemia. Brit J Haematol 145, 788-800 (2009).
10. R. Bejar et al., Clinical Effect of Point Mutations in Myelodysplastic Syndromes. New Engl J Med 364, 2496-2506 (2011).
11. J. P. Patel et al., Prognostic Relevance of Integrated Genetic Profiling in Acute Myeloid Leukemia. New Engl J Med 366, 1079-1089 (2012).
12. O. Abdel-Wahab et al., ASXL1 Mutations Promote Myeloid Transformation through Loss of PRC2-Mediated Gene Repression. Cancer Cell 22, 180-193 (2012).
13. A. Balasubramani et al., Cancer-associated ASXL1 mutations may act as gain-of-function mutations of the ASXL1-BAP1 complex. Nat Commun 6, (2015).
14. H. Yang et al., Gain of function of ASXL1 truncating protein in the pathogenesis of myeloid malignancies. Blood 131, 328-341 (2018).
15. A. Campagne et al., BAP1 complex promotes transcription by opposing PRC1-mediated H2A ubiquitylation. Nat Commun 10, (2019).
16. Y. Guo et al., Reduced BAP1 activity prevents ASXL1 truncation-driven myeloid malignancy in vivo. Leukemia 32, 1834-1837 (2018).
17. H. Yu et al., The Ubiquitin Carboxyl Hydrolase BAP1 Forms a Ternary Complex with YY1 and HCF-1 and Is a Critical Regulator of Gene Expression. Mol Cell Biol 30, 5071-5085 (2010).
18. A. Bononi et al., BAP1 regulates IP3R3-mediated $Ca^{2+}$ flux to mitochondria suppressing cell transformation. Nature 546, 549-+(2017).
19. M. R. Morris, F. Latif, The epigenetic landscape of renal cancer. Nat Rev Nephrol 13, 47-60 (2017).
20. R. Verdijk et al., Clinical significance of immunohistochemistry for detection of BAP1 mutations in uveal melanoma. Virchows Arch 465, S44-S44 (2014).
21. R. Murali, T. Wiesner, R. A. Scolyer, Tumours associated with BAP1 mutations. Pathology 45, 116-126 (2013).
22. J. Y. Qin et al., BAP1 promotes breast cancer cell proliferation and metastasis by deubiquitinating KLF5. Nat Commun 6, (2015).
23. M. He et al., Intrinsic apoptosis shapes the tumor spectrum linked to inactivation of the deubiquitinase BAP1. Science 364, 283-+(2019).
24. D. D. Sahtoe, W. J. van Dijk, R. Ekkebus, H. Ovaa, T. K. Sixma, BAP1/ASXL1 recruitment and activation for H2A deubiquitination. Nat Commun 7, (2016).
25. S. Daou et al., The BAP1/ASXL2 Histone H2A Deubiquitinase Complex Regulates Cell Proliferation and Is Disrupted in Cancer. J Biol Chem 290, 28643-28663 (2015).
26. N. Mashtalir et al., Autodeubiquitination Protects the Tumor Suppressor BAP1 from Cytoplasmic Sequestration Mediated by the Atypical Ubiquitin Ligase UBE2O. Mol Cell 54, 392-406 (2014).
27. Y. Fang, D. Fu, X. Z. Shen, The potential role of ubiquitin c-terminal hydrolases in oncogenesis. Bba-Rev Cancer 1806, 1-6 (2010).
28. P. D'Arcy et al., Inhibition of proteasome deubiquitinating activity as a new cancer therapy. Nat Med 17, 1636-U1150 (2011).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating cancer in a subject in need thereof, the method comprising administering to the subject a therapeutic amount of a therapeutic agent that inhibits the biological activity of the BAP1 histone H2A deubiquitinase (DUB) complex (BAP1 complex), wherein the subject has a mutation in the ASXL1 gene and wherein the subject has a mutation in the ASXL1 gene that results in a truncated ASXL1 protein.

2. The method of claim 1, wherein the cancer is a myeloid neoplasm.

3. The method of claim 1, wherein the cancer is selected from the group consisting of acute myeloid leukemia (AML), myelodysplastic syndrome (MDS), myeloproliferative neoplasm (MPN), chronic myelomonocytic leukemia (CMML), and chronic myeloid leukemia (CML).

4. The method of claim 1, wherein the therapeutic agent comprises a compound of formula

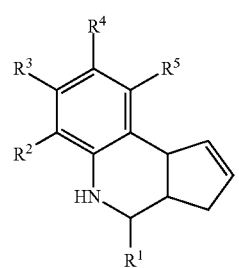

wherein:
R$^1$ is hydrogen, or aryl or heteroaryl optionally substituted at one or more positions with halo or nitro;

R² is selected from hydrogen and halo;

R³ is selected from hydrogen and halo;

R⁴ is selected from hydrogen, halo, amino, nitro, alkyl-carboxyamido, R⁶—C(O)NH—*, or R⁶—NH—C(O)—* wherein R⁶ is aryl or heteroaryl optionally substituted at one or more positions with halo or nitro and * is a point of attachment; and R⁵ is selected from hydrogen and halo; or a suitable pharmaceutical salt or solvate thereof.

5. The method of claim 4, wherein the compound is selected from

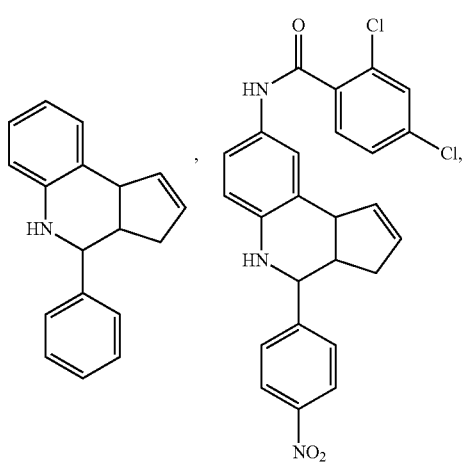

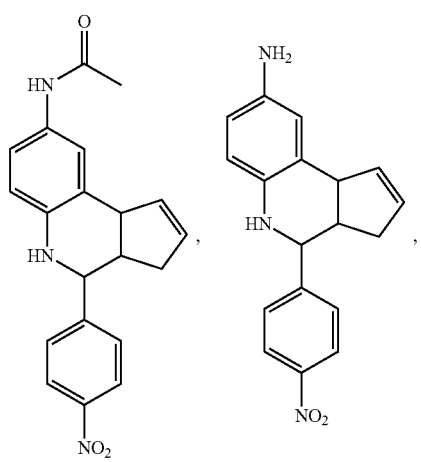

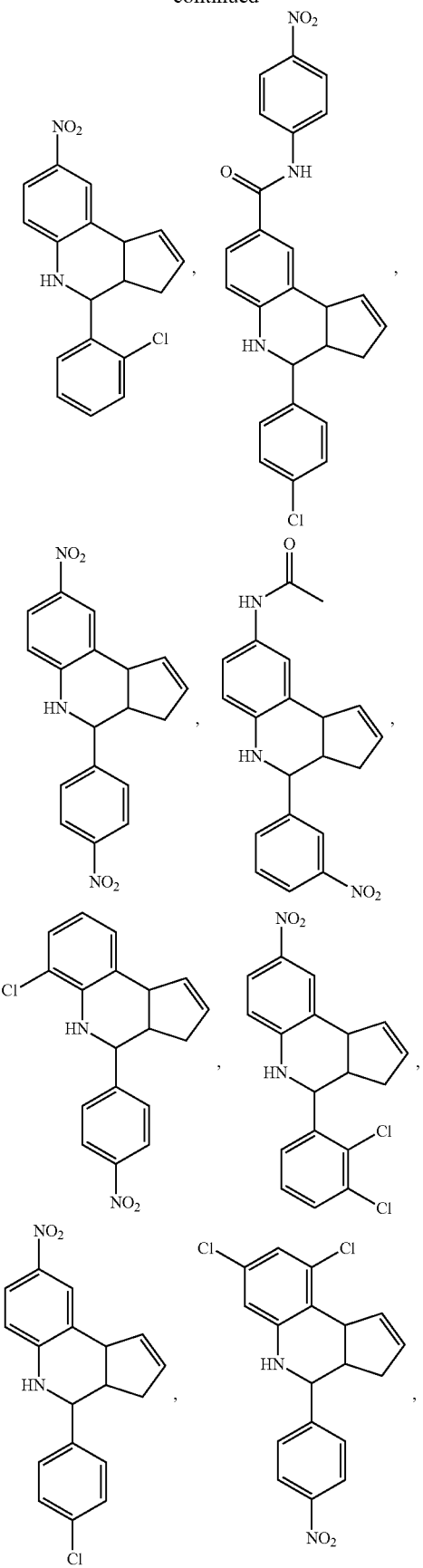

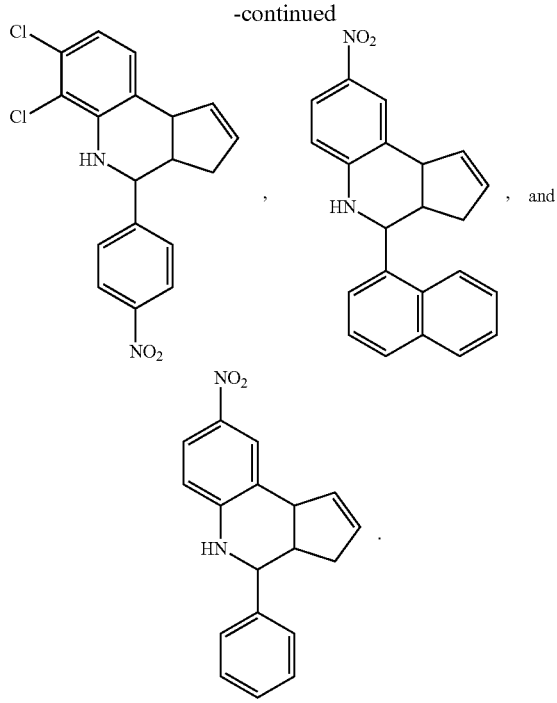

6. The method of claim 1, wherein the therapeutic agent is a compound of the following formula or a suitable pharmaceutical salt or solvate thereof:

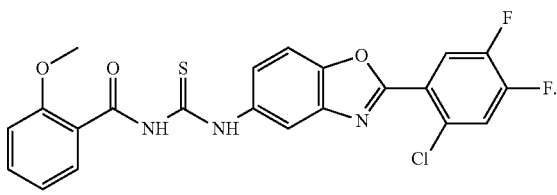 [SMILES: COc1ccccc1C(=O)NC(=S)Nc1ccc2oc(-c3cc(F)c(F)cc3Cl)nc2c1]

7. A method for treating cancer in a subject in need thereof, the method comprising administering to the subject a therapeutic amount of a therapeutic agent that inhibits the biological activity of the BAP1 histone H2A deubiquitinase (DUB) complex (BAP1 complex), wherein the therapeutic agent comprises a compound of formula

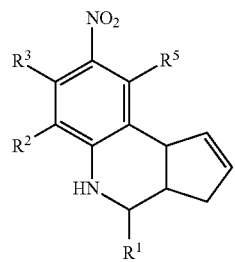

wherein:
R¹ is hydrogen, or aryl or heteroaryl optionally substituted at one or more positions with halo or nitro;
R² is selected from hydrogen and halo;
R³ is selected from hydrogen and halo; and
R⁵ is selected from hydrogen and halo; or a suitable pharmaceutical salt or solvate thereof.

8. The method of claim 7, wherein the cancer is a myeloid neoplasm.

9. The method of claim 7, wherein the cancer is selected from the group consisting of acute myeloid leukemia (AML), myelodysplastic syndrome (MDS), myeloproliferative neoplasm (MPN), chronic myelomonocytic leukemia (CMML), and chronic myeloid leukemia (CML).

10. The method of claim 7, wherein the subject has a mutation in the ASXL1 gene.

11. The method of claim 7, wherein the subject has a mutation in the ASXL1 gene that results in a truncated ASXL1 protein.

12. A method for treating cancer in a subject in need thereof, the method comprising administering to the subject a therapeutic amount of a therapeutic agent that inhibits the biological activity of the BAP1 histone H2A deubiquitinase (DUB) complex (BAP1 complex), wherein the therapeutic agent comprises a compound of formula

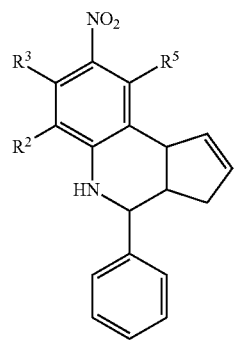

wherein:
R² is selected from hydrogen and halo;
R³ is selected from hydrogen and halo; and
R⁵ is selected from hydrogen and halo or a suitable pharmaceutical salt or solvate thereof.

13. The method of claim 12, wherein the cancer is a myeloid neoplasm.

14. The method of claim 12, wherein the cancer is selected from the group consisting of acute myeloid leukemia (AML), myelodysplastic syndrome (MDS), myeloproliferative neoplasm (MPN), chronic myelomonocytic leukemia (CMML), and chronic myeloid leukemia (CML).

15. The method of claim 12, wherein the subject has a mutation in the ASXL1 gene.

16. The method of claim 12, wherein the subject has a mutation in the ASXL1 gene that results in a truncated ASXL1 protein.

* * * * *